(12) United States Patent
Nonaka et al.

(10) Patent No.: US 9,128,081 B2
(45) Date of Patent: *Sep. 8, 2015

(54) TDP-43-STORING CELL MODEL

(71) Applicant: TOKYO METROPOLITAN INSTITUTE OF MEDICAL SCIENCE, Tokyo (JP)

(72) Inventors: Takashi Nonaka, Tokyo (JP); Tetsuaki Arai, Chiba (JP); Haruhiko Akiyama, Tokyo (JP); Masato Hasegawa, Tokyo (JP); Makiko Yamashita, Tokyo (JP)

(73) Assignee: Tokyo Metropolitan Institute of Medical Science, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/096,943

(22) Filed: Dec. 4, 2013

(65) Prior Publication Data

US 2014/0099660 A1    Apr. 10, 2014

Related U.S. Application Data

(63) Continuation of application No. 12/936,585, filed as application No. PCT/JP2009/054826 on Mar. 6, 2009, now Pat. No. 8,715,643.

(30) Foreign Application Priority Data

Apr. 9, 2008 (JP) .................................. 2008-101899

(51) Int. Cl.
*G01N 33/50* (2006.01)
*C07K 14/47* (2006.01)

(52) U.S. Cl.
CPC ........ *G01N 33/5058* (2013.01); *C07K 14/4711* (2013.01); *G01N 33/5014* (2013.01)

(58) Field of Classification Search
CPC .................................................. C07K 14/4711
USPC .............. 424/93.2, 93.21; 435/6.1, 6.13, 6.16
See application file for complete search history.

(56) References Cited

U.S. PATENT DOCUMENTS

| | | | |
|---|---|---|---|
| 5,688,511 A | 11/1997 | Gaynor et al. | |
| 6,187,785 B1 | 2/2001 | Zefirov et al. | |
| 6,953,794 B2 | 10/2005 | Wischik et al. | |
| 7,745,391 B2 | 6/2010 | Mintz et al. | |
| 8,715,643 B2 * | 5/2014 | Nonaka et al. | 424/93.21 |

FOREIGN PATENT DOCUMENTS

| | | |
|---|---|---|
| GB | 2 335 192 A | 9/1999 |
| JP | 11-502925 A | 3/1999 |
| JP | H11-285382 A | 10/1999 |
| WO | WO 96/30766 A1 | 10/1996 |

OTHER PUBLICATIONS

Arai T. et al., "TDP-43 is a component of ubiquitin-positive tau-negative inclusions in frontotemporal lobar degeneration and amyotrophic lateral sclerosis", Biochem. Bipchem. Biophys. Res. Commun., 2006, vol. 351, No. 3, p. 602-611.
Ayala et al., "Human, *Drosophila*, and *C. elegans* TDP43: Nucleic Acid Binding Properties and Splicing Regulatory Function," J. Mol. Biol. (2005), vol. 348, pp. 575-588.
Buratti E et al., Nuclear factor TDP-43 and SR proteins promote in vitro and in vivo CFTR exon 9 skipping, EMBO J., 2001, vol. 20(7), p. 1774-1784.
Buratti E. et al.TDP-43 Binds Heterogeneous Nuclear Ribonucleoprotein A/B through its C-terminal Tail, J. Boil. Chem., Nov. 11, 2005, vol. 280, No. 45, p. 37572-37584.
Deng HX et al., "Amyotrophic latral sclerosis and structural defects in Cu, Zn superoxide dismutase", 1993, Science, vol. 261, p. 1047-1051.
European Search Report issued Oct. 21, 2011, in European Patent Application No. 09730344.0.
Forman et al., "TDP-43: a novel neurodegenerative proteinopathy," Current Opinion in Neurobiology (2007), vol. 17, pp. 548-555.
Geser F et al., "Evidence of multisystem disorder in whole-brain map of pathological TDP-43 in amyotrophic lateral scierosis", 2008, Arch. Neurol., vol. 65, p. 636-641.
International Search Report dated May 26, 2009 in International Application No. PCT/JP2009/054826.
Mackenzie IR et al, "Pathological TDP-43 distinguishes sporadic amyotrophic lateral sclerosis from amyotrophic lateral sclerosis with SOD1 mutations", 2007, Ann. Neurol., vol. 61, p. 427-434.
Neuman, M., "TDP-43 proteinopathies: a new class of proteinopathies," Future Neurol. (2007), vol. 2, No. 5, pp. 549-557.
Neumann M. et al.,"Ubiquitinated TDT-43 in Frontotemporal Lobar Degeneration and Amyotrophic Lateral Sclerosis", Science, Oct. 6, 2006, vol. 314, No. 5796, p. 130-133.
Nishihira Y et al, "Sporadic amyotrophic lateral clerosis: two pathological patterns shown by analysis of distribution of TDP-43-immunoreactive neuronal and glialcytoplasmic inclusions", 2008, Acta. Neuropathol., vol. 116, p. 169-182.
Nonaka T. et al., "Phosphorylated and ubiquitinated TDP-43 pathological inclusions in ALS and FTLD-U are recapitulated in SH-SY5Y cells", FEBS Lett, Jan. 2009, vol. 583, No. 2, p. 394-400.
Ou et al., "Cloning and Characterization of a Novel Cellular Protein TDP-43, that Blinds to Human Immunodeficiency Virus Type 1 TAR DNA Sequence Motifs," Journal of Virology (Jun. 1995), vol. 69, No. 6, pp. 3584-3596.
Rosen DR et al., "Mutations in Cu/Zn superoxide dismutase gene are associated with familial amyotrophic lateral sclerosis", 1993, Nature, vol. 362, p. 59-62.

(Continued)

*Primary Examiner* — Janice Li
(74) *Attorney, Agent, or Firm* — Birch, Stewart, Kolasch & Birch, LLP

(57) ABSTRACT

Disclosed is a transformed cell (a cell model) which can form a cytoplasmic inclusion body derived from TAR DNA-binding protein of 43 kDa (TDP-43) that is found in the brain of a patient suffering from a neurodegenerative disease such as FTLD and ALS. The transformed cell is characterized by having, introduced therein, a promoter capable of functioning in a host cell and a mutant TDP-43 gene.

14 Claims, 24 Drawing Sheets
(17 of 24 Drawing Sheet(s) Filed in Color)

(56) References Cited

OTHER PUBLICATIONS

Sreedharan et al., "TDP-43 Mutations in Familial and Sporadic Amyotophic Lateral Scierosis," Science (Mar. 2008) vol. 319, pp. 1668-1672.

Tan CF et al, "TDP-43 immunoreactivity in neuronal inclusions in familial amyotrophic lateral sclerosis with or without SOD1 gene mutation", 2007, Acta. Neuropathol., vol. 113, p. 535-542.

Wang et al., "Structural diversity and functional implications of the eukaryotic TDP gene family," Genomics (2004), vol. 83, pp. 130-139.

Winton et al., "Disturbance of Nuclear and Cytoplasmic TAR DNA-binding Protein (TDP-43) Induces Disease-like Redistribution, Sequestration, and Aggregate Formulation," J. Biol Chem. (May 2008), vol. 283, No. 19, pp. 13302-13309.

* cited by examiner

Fig. 1
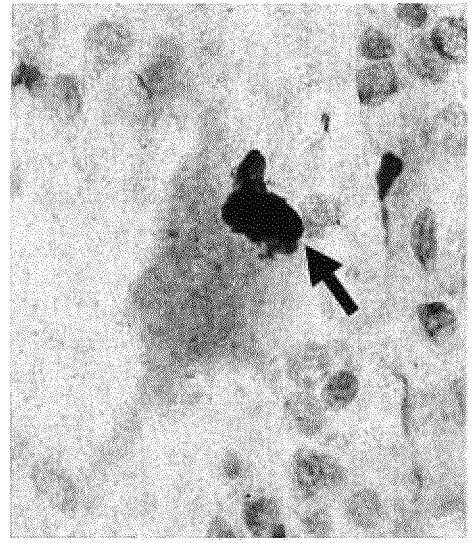
In nucleus (arrow) and cytoplasm
(Diameter 5-10 μm)
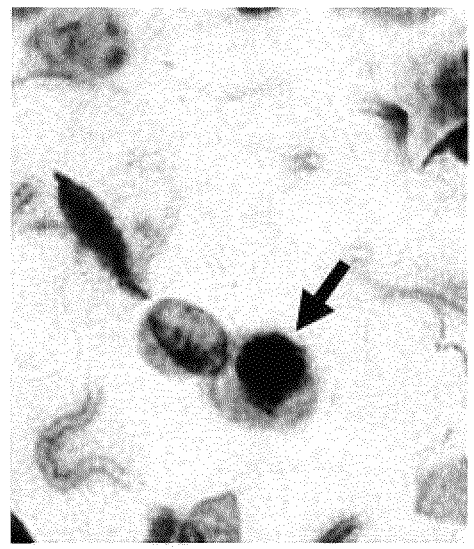
In cytoplasm (arrow)
(Diameter 10-20 μm)
Phosphorylated and ubiquitinated TDP-43 as
primary component of intracellular inclusion

Fig.2

Amino acid sequence of wild-type TDP-43
(SEQ ID NO:2)

1
MSEYIRVTEDENDEPIEIPSEDDGTVLLSTVTAQFPGACGLRYRNPVSQCMRGVRLVEGI

LHAPDAGWGNLVYVVNYPKDNKRKMDETDASSAVKVKRAVQKTSDLIVLGLPWKTTEQDL
              NLS1(78-84)

KEYFSTFGEVLMVQVKKDLKTGHSKGFGFVRFTEYETQVKVMSQRHMIDGRWCDCKLPNS

KQSQDEPLRSRKVFVGRCTEDMTEDELREFFSQYGDVMDVFIPKPFRAFAFVTFADDQIA
       NLS2(187-192)

QSLCGEDLIIKGISVHISNAEPKHNSNRQLERSGRFGGNPGGFGNQGGFGNSRGGGAGLG

NNQGSNMGGGMNFGAFSINPAMMAAAQAALQSSWGMMGMLASQQNQSGPSGNNQNQGNMQ

414
REPNQAFGSGNNSYSGSNSGAAIGWGSASNAGSGSGFNGGFGSSMDSKSSGWGM

Fig. 11 Expression of GFP-TDP 162-414

CFTR exon 9 skipping assay for various GFP-fused bodies

TDP-43-STORING CELL MODEL

CROSS-REFERENCE TO RELATED APPLICATIONS

This application is a continuation application of U.S. application Ser. No. 12/936,585 filed on Oct. 6, 2010, which is the National Phase of International Application No. PCT/JP2009/054826 filed on Mar. 6, 2009, which claims priority to Japanese Patent Application No. 2008-101899 filed on Apr. 9, 2008, all of which are hereby expressly incorporated by reference into the present application.

TECHNICAL FIELD

The present invention relates to a transformed cell, namely a TDP-43-accumulating cell model that forms an inclusion (aggregate) originating from TAR DNA-binding protein of 43 kDa (TDP-43) in the cell (in cytoplasm or nucleus).

BACKGROUND ART

In many neurodegenerative diseases including Alzheimer's disease and Parkinson's disease, abnormal protein structures that accumulate in the nerve cells are found in the patients' brains, and formation of these abnormal structures is considered to be closely related to the onset of the diseases. In the cases of neurodegenerative diseases such as frontotemporal lobar degeneration (FTLD) and amyotrophic lateral sclerosis (ALS), ubiquitin-positive inclusions emerge in the nerve cells of the patient's brain (FIG. 1). Since the emerging sites of the inclusions are found to correspond to the sites with loss of nerve cells, emergence of these intracellular inclusions is considered to cause nerve cell death and eventually lead to the onset of the diseases. In the recent research, the present inventors have identified a nuclear protein called TAR DNA-binding protein of 43 kDa (TDP-43) as a primary component of the intracellular inclusions found in the FTLD or ALS patients' brain (Arai T et al., TDP-43 is a component of ubiquitin-positive tau-negative inclusions in frontotemporal lobar degeneration and amyotrophic lateral sclerosis, Biochem. Biophys. Res. Commun., 2006, vol. 351(3), p. 602-611; Neumann M et al., Ubiquitinated TDP-43 in frontotemporal lobar degeneration and amyotrophic lateral sclerosis, Science, 2006, vol. 314(5796), p. 130-133). TDP-43 is a protein that is localized in the nucleus and considered to be involved in transcriptional regulation and the like (Buratti E et al., Nuclear factor TDP-43 and SR proteins promote in vitro and in vivo CFTR exon 9 skipping, EMBO J., 2001, vol. 20(7), p. 1774-1784), but little is known about its actual functions.

Among ALS, i.e., intractable nerve diseases that progress very fast, about 5-10% are familial ALS and the resulting majorities are presumed to be sporadic ALS. Among familial ALS, approximately 20% are cases associated with genetic abnormality of superoxide dismutase 1 (SOD1) (Deng H X et al., Amyotrophic lateral sclerosis and structural defects in Cu, Zn superoxide dismutase, 1993, Science, vol. 261, p. 1047-1051; Rosen D R et al., Mutations in Cu/Zn superoxide dismutase gene are associated with familial amyotrophic lateral sclerosis, 1993, Nature, vol. 362, p. 59-62). While many reports have been made as to the association between SOD1 abnormality and the onset, it is also suggested that it has different neuropathological characteristics from sporadic ALS. Specifically, while TDP-43-positive inclusions are observed in the sporadic ALS patients' brains in almost all cases (Geser F et al., Evidence of multisystem disorder in whole-brain map of pathological TDP-43 in amyotrophic lateral sclerosis, 2008, Arch. Neurol., vol. 65, p. 636-641; Nishihira Y et al, Sporadic amyotrophic lateral sclerosis: two pathological patterns shown by analysis of distribution of TDP-43-immunoreactive neuronal and glial cytoplasmic inclusions, 2008, Acta. Neuropathol., vol. 116, p. 169-182), ubiquitin-positive inclusions found in familial ALS patients' brains with SOD1 mutation are not stained with anti-TDP-43 antibody (Mackenzie I R et al, Pathological TDP-43 distinguishes sporadic amyotrophic lateral sclerosis from amyotrophic lateral sclerosis with SOD1 mutations, 2007, Ann. Neurol., vol. 61, p. 427-434; Tan C F et al, TDP-43 immunoreactivity in neuronal inclusions in familial amyotrophic lateral sclerosis with or without SOD1 gene mutation, 2007, Acta. Neuropathol., vol. 113, p. 535-542). These facts suggest that familial ALS associated with SOD1 mutation has different onset mechanism from the rest of familial ALS and the predominant sporadic ALS. In light of the above-described discovery of the TDP-43 gene mutation in the ALS patients, TDP-43 abnormality appears to be the primary factor of the onset of majority of ALS, and its intracellular aggregation is closely related to the onset.

Thus, elucidation of how TDP-43 protein is accumulated in the cells by what kind of mechanism and how it exerts cytotoxicity, in other words, elucidation of the mechanism of intracellular TDP-43 inclusion formation and the neurodegenerative mechanism caused by the inclusions would be a huge contribution not only to the elucidation of the onset mechanisms of ALS and FTLD (elucidation of the cause of the diseases) but also to the development of a therapeutic drug and method for them.

DISCLOSURE OF THE INVENTION

Thus, an objective to be solved by the present invention is to provide a transformed cell that forms an intracellular inclusion (aggregate) originating from TAR DNA-binding protein of 43 kDa (TDP-43) in the brain of a patient suffering from a neurodegenerative disease such as FTLD or ALS. The present invention also has objectives of providing a method for screening a therapeutic drug for a neurodegenerative disease by using the transformed cell, and a method for assessing a side-effect of a therapeutic drug for a neurodegenerative disease. The present invention further has an objective of providing a pharmaceutical composition for treating and/or preventing a neurodegenerative disease.

In order to solve the above problems, the present inventors have gone through keen examination and worked on constructing a culture cell that can reproduce the intracellular TDP-43 inclusions found in the brain of a patient suffering from FTLD or ALS in the laboratory.

TDP-43 of the intracellular inclusions found in the patient's brain is accumulated in the nucleus or in the cytoplasm (FIG. 1). Accumulation of TDP-43, which is normally a nuclear protein, in the cytoplasm means that localization of TDP-43 is altered in the cell. Accordingly, the present inventors have identified the nuclear localization signal of TDP-43 to prepare a deficient mutant thereof (mutant TDP-43 protein) and the like. In addition, the present inventors have also focused on proteasome that has recently been suggested of its association with neurodegenerative diseases, and combined the expression of the mutant TDP-43 protein with a treatment of inhibiting proteasome activity and eventually succeeded in forming TDP-43 inclusions in the nucleus and the cytoplasm. Moreover, since not only full-length TDP-43 but also TDP-43 fragments are collected in surfactant-insoluble fractions, which are characteristic of TDP-43 accumulated in the patient's brain, the present inventors focused on these fragments and tried to express fusion proteins of respective TDP-43 fragments and green fluorescent protein (GFP). As a result, they succeeded in forming intracellular TDP-43 inclusions in some of the cells expressing the fusion proteins. Furthermore, the present inventors searched for a compound having an effect of suppressing the formation of the inclusion by using the above-described cell capable of forming an intracellular TDP-43 inclusion, and, in fact, found that certain low-molecular compounds have this effect. Hence, the present invention was achieved.

Thus, the present invention is as follows.

(1) A transformed cell having a promoter operable in a host cell and a mutant TDP-43 gene.

Examples of the mutant TDP-43 in the transformed cell of the present invention include those having an activity of forming an intracellular inclusion.

Examples of the mutant TDP-43 also include the following proteins (1a) to (1d) and (2a) to (2d).

(1a) A protein having an amino acid sequence obtained by deleting amino acids 78-84 from the amino acid sequence of wild-type TDP-43.

(1b) A protein having an amino acid sequence obtained by deleting amino acids 187-192 from the amino acid sequence of wild-type TDP-43.

(1c) A protein having an amino acid sequence obtained by deleting amino acids 78-84 and 187-192 from the amino acid sequence of wild-type TDP-43.

(1d) A protein that has an amino acid sequence having one or a few amino acids deleted from, substituted in or added to the amino acid sequence (1a), (1b) or (1c) and that has an activity of forming an intracellular inclusion.

(2a) A protein having an amino acid sequence including amino acids 162-414 of the amino acid sequence of wild-type TDP-43.

(2b) A protein having an amino acid sequence including amino acids 218-414 of the amino acid sequence of wild-type TDP-43.

(2c) A protein having an amino acid sequence including amino acids 1-161 of the amino acid sequence of wild-type TDP-43.

(2d) A protein that has an amino acid sequence having one or a few amino acids deleted from, substituted in or added to the amino acid sequence (2a), (2b) or (2c) and that has an activity of forming an intracellular inclusion.

Other examples of the mutant TDP-43 include those that have no CFTR exon 9 skipping activity.

An example of the transformed cell of the present invention includes a transformed mammal cell, specific examples being a central nervous system cell, a peripheral nervous system cell and a neuroblast.

(2) A method for screening a therapeutic drug for a neurodegenerative disease or an agent for suppressing formation of an intracellular inclusion of mutant TDP-43, the method comprising the steps of: causing the cell according to (1) above to make contact with a candidate substance to measure the cellular activity of the cell; and using the obtained measurement result as an indicator.

According to the screening method of the present invention, examples of cellular activities include proliferation capacity, viability as well as the rate, number and size of the intracellular mutant TDP-43 inclusion formed.

Moreover, according to the screening method of the present invention, examples of neurodegenerative diseases include frontotemporal lobar degeneration and amyotrophic lateral sclerosis, in particular, diseases associated with formation of intracellular TDP-43 inclusions (diseases associated with intracellular accumulation of TDP-43).

(3) A method for assessing a side-effect of a therapeutic drug for a neurodegenerative disease, the method comprising the steps of: causing the cell according to (1) above to make contact with the therapeutic drug for the neurodegenerative disease to measure the cellular activity of the cell: and using the obtained measurement result as an indicator.

According to the method of the present invention for assessing a side-effect, examples of cellular activities include neurite elongation capability, proliferation capacity and viability.

Furthermore, according to the method of the present invention for assessing a side-effect, examples of neurodegenerative diseases include frontotemporal lobar degeneration and amyotrophic lateral sclerosis, in particular, diseases associated with formation of intracellular TDP-43 inclusions (diseases associated with intracellular accumulation of TDP-43).

(4) A pharmaceutical composition for treating and/or preventing a neurodegenerative disease, comprising methylene blue and/or dimebon.

For a pharmaceutical composition of the present invention, examples of neurodegenerative diseases include frontotemporal lobar degeneration and amyotrophic lateral sclerosis, in particular, diseases associated with formation of intracellular TDP-43 inclusions (diseases associated with intracellular accumulation of TDP-43).

BRIEF DESCRIPTION OF THE DRAWINGS

The patent or application file contains at least one drawing executed in color. Copies of this patent or patent application publication with color drawing(s) will be provided by the USPTO upon request and payment of the necessary fee.

FIG. 1 shows pictures of intracellular TDP-43 inclusions found in FTLD or ALS patient's brain. The picture on the left shows an inclusion formed in the nucleus while the picture on the right shows an inclusion formed in the cytoplasm.

FIG. 2 shows the amino acid sequence of wild-type TDP-43 (SEQ ID NO:2). Amino acids corresponding to the nuclear localization signal sequence (NLS1) and the nuclear localization signal homologous sequence (NLS2) are underlined. Herein, all of the "amino acid residue numbers" recited in the examples represent the positions of the amino acid residues and amino acid sequence regions beginning from the N-terminal of the amino acid sequence shown in FIG. 2 (or SEQ ID NO:2). Moreover, a nucleotide sequence coding for a certain amino acid sequence may be identified by referring to the nucleotide sequence represented by SEQ ID NO:1 (shown along with the amino acid sequence).

BEST MODES FOR CARRYING OUT THE INVENTION

Figure 3:
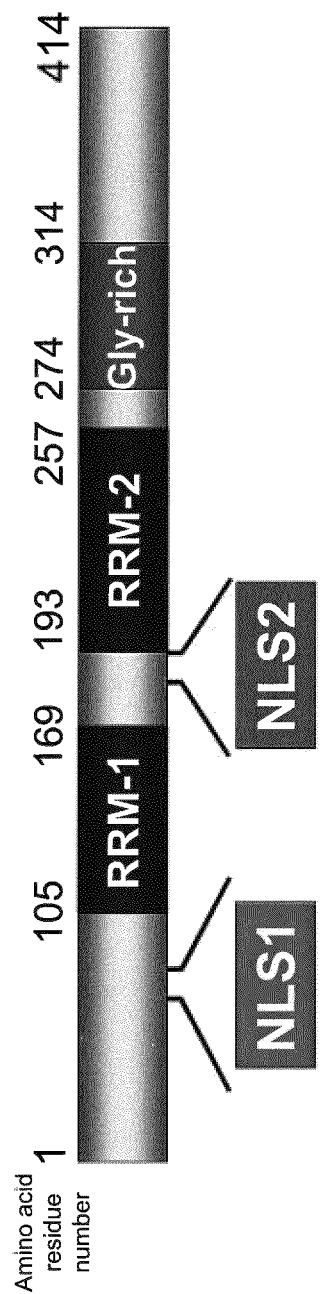
FIG. 3 is a schematic view showing a method for identifying TDP-43 nuclear localization signal (NLS).

Hereinafter, the present invention will be described in detail. The scope of the present invention should not be limited by these descriptions, and may appropriately be modified and carried out apart from the following examples without departing from the spirit of the invention. The present specification incorporates the entire specification of Japanese Patent Application No. 2008-101899 to which the present application claims priority. In addition, all of the prior art documents and laid-open publications, patent publication and other patent documents cited herein are incorporated herein by reference.

1. SUMMARY OF THE PRESENT INVENTION

In many neurodegenerative diseases such as Alzheimer's disease, ubiquitin-positive protein inclusions are formed in the nerve cells. As to neurodegenerative diseases such as frontotemporal lobar degeneration (FTLD) or amyotrophic lateral sclerosis (ALS), the primary component of the ubiquitin-positive inclusions observed specifically in the patient's brain has not been found previously, but current researches identified a certain intranuclear protein called TAR DNA-binding protein of 43 kDa (TDP-43) as the primary component of the above-mentioned inclusions (Arai T et al., TDP-43 is a component of ubiquitin-positive tau-negative inclusions in frontotemporal lobar degeneration and amyotrophic lateral sclerosis, Biochem. Biophys. Res. Commun., 2006, vol. 351 (3), p. 602-611; Neumann M et al., Ubiquitinated TDP-43 in frontotemporal lobar degeneration and amyotrophic lateral sclerosis, Science, 2006, vol. 314(5796), p. 130-133). TDP-43 is one kind of heterogeneous nuclear ribonucleoproteins (hnRNP) and considered to be a protein that is localized in the nucleus and that binds to RNA or other hnRNP and get involved in processes such as RNA stabilization, selective splicing, transcriptional regulation and the like (Buratti E et al., Nuclear factor TDP-43 and SR proteins promote in vitro and in vivo CFTR exon 9 skipping, EMBO J., 2001, vol. 20(7), p. 1774-1784). However, questions as to what kind of mechanism is involved in accumulation of TDP-43 in the nerve cells, as to whether or not the accumulated TDP-43 has cellular toxicity, and as to what kind of mechanism induces cell death have totally been unclear.

The present inventors considered that a TDP-43-accumulating cell model obtained by using a cultured cell or the like was necessary for elucidating these questions, and thus attempted to develop such a model system. As a result, fusion proteins containing respective mutants (mutant TDP-43 proteins) or fragments of TDP-43 protein were expressed in cells, where in some cases the cells were subjected to a proteasome inhibition treatment, to allow formation of TDP-43 inclusions in the cells, thereby succeeding in accumulating TDP-43.

Use of this model system allows screening of an agent or a gene that suppresses intracellular TDP-43 accumulation. The model system may also be utilized for preparing a transgenic animal, and thus appears to be very useful for the development of a novel therapeutic drug and method for FTLD or ALS.

2. TRANSFORMED CELL (CELL MODEL)

A transformed cell of the present invention is a cell into which a promoter operable in a host cell and a mutant TDP-43 gene are introduced (hereinafter, also referred to as a "mutant TDP-43-transformed cell"). The transformed cell of the present invention expresses a mutant TDP-43 which is a primary component of an intracellular (intracytoplasmic or intranuclear) inclusion, and thus is a useful cell model for neurodegenerative diseases such as FTLD and ALS.

(1) Summary of Method for Preparing Transformed Cell

Generally, in order to overexpress a foreign protein of interest (mutant TDP-43 according to the present invention) in an intended host cell, first, a recombinant vector needs to be constructed by integrating the gene of the protein of interest into an expression vector. In this case, a promoter operable in a host cell is preferably linked in advance to the gene to be integrated into the expression vector. Apart from the promoter, Kozak sequence, a terminator, an enhancer, a splicing signal, a poly-A addition signal, a selective marker and the like may also be linked to the gene. Here, elements (for example, a promoter) necessary for gene expression may be contained in the gene of the protein of interest from the beginning or if they are originally contained in the expression vector, those can be used, where the present invention is not particularly limited to either case.

As a method for integrating the gene of the protein of interest into an expression vector, various methods employing known gene recombination techniques such as a method using a restriction enzyme or a method using topoisomerase may be employed. Moreover, the expression vector is not particularly limited, and a suitable vector such as plasmid DNA, bacteriophage DNA, retrotransposon DNA, a retrovirus vector, artificial chromosomal DNA or the like may appropriately be selected according to the host cell used.

Next, the constructed recombinant vector is introduced into a host cell to obtain a transformant, which is cultured for expressing the protein of interest. Here, the term "transformation" used with the present invention refers to introduction of a foreign gene into a host cell. Specifically, the term covers both meanings where plasmid DNA or the like is introduced (transformed) into a host cell to introduce the foreign gene, and where a host cell is infected (transduced) with any of various viruses and phages to introduce the foreign gene.

The host cell is not particularly limited as long as it is capable of expressing the protein of interest after introduction of the recombinant vector, and for example, animal cells derived from various mammals such as human, mouse and rat, or according to circumstances, a yeast cell or the like may appropriately be selected and used. Examples of such animal cells used include a human fibroblast cell, a CHO cell, a monkey COS-7 cell, Vero, a mouse L cell, rat GH3, a human FL cell, a neuroblast, a central nervous system cell and a peripheral nervous system cell. According to the present invention, nerve cells such as a neuroblast, a central nervous system cell and a peripheral nervous system cell are particularly favorable. Meanwhile, preferable examples of yeasts include, but not limited to, *Saccharomyces cerevisiae* and *Schizosaccharomyces pombe*.

A method for obtaining a transformed cell, that is, a method for introducing a recombinant vector into a host cell is not particularly limited, and may appropriately be selected considering the combination of the types of the host cell and the expression vector. For example, preferable methods include a lipofection method, an electroporation method, a heat-shock method, a PEG method, a calcium phosphate method, a DEAE dextran method, and a method in which various viruses such as DNA and RNA viruses are used for infection.

In the resulting transformed cell, the codon type of the gene contained in the recombinant vector is not limited and may be the same with or different from the codon type of the host cell actually used.

The above-described summary of the method for preparing a transformed cell may also be applied to the preparation of a transformed cell of the present invention (mutant TDP-43-transformed cell).

(2) Mutant TDP-43-Transformed Cell

In the transformed cell of the present invention, the expression mode of a mutant TDP-43, i.e., a protein of interest, is not particularly limited and it may be stably expressed or transiently expressed in the host cell. Here, the term "stable expression" as used with the present invention refers to homeostatic expression based on the gene integrated into the chromosome of the host cell (an intrachromosomal gene), whereas the term "transient expression" refers to non-homeostatic expression based on the gene that is not integrated into the chromosome of the host cell (an extrachromosomal gene such as a plasmid).

In the transformed cell of the present invention, the host cell is preferably but not limited to a mammal cell. The mammal cell, without limitation, may be either a human-derived cell or a non-human-derived cell. Preferable examples of non-human animals include mammals such as a mouse, a rat, a guinea pig, a rabbit, a hare, a pig, a dog, a cat, a monkey, a sheep, a bovine and a horse, among which, rodents (order Rodentia) such as a mouse, a rat and a guinea pig are more preferable, and a mouse and a rat are particularly preferable. Furthermore, although the cell type of the animal cell is not limited, a neuroblast, a central nervous system cell, a peripheral nervous system cell or the like is particularly preferable.

In order to introduce a gene of a protein of interest (a mutant TDP-43 gene) into the host cell, a recombinant vector containing this gene is usually used as described above. In this case, if stable expression is desirable in the host cell, a known expression vector that is capable of recombination with chromosomal DNA (a stable expression vector) is preferably used whereas, if transient expression is desirable, a known expression vector that is capable of autonomous replication in the cell without going through recombination with chromosomal DNA (transient expression vector) is preferably used. A vector used for stable expression or transient expression may appropriately be a vector that has both functions of the stable expression vector and the transient expression vector. A stable expression vector for an animal cell may be a known vector such as pCEP4 vector or pTarget vector, and any of various known vectors may be used for a yeast cell. Moreover, a transient expression vector used for an animal cell may be a known vector such as pcDNA3.1 vector, pcDNA3(+) vector, pcDNA3(−) vector, pEGFP-C1 vector (an expression vector for GFP (specifically, EGFP)-fused protein), pCEP4 vector or pTarget vector, while a transient expression vector used for a yeast cell may be any of various known vectors.

As the above-mentioned various expression vectors, a vector containing a promoter operable in a host cell may appropriately be selected from known vectors to control the expression of the gene of the protein of interest in the host cell with this promoter. A preferable expression vector allows introduction of a mutant TDP-43 gene under the control of the promoter operable in the host cell. Here, the phrase "under the control of the promoter" means that the promoter functions such that the mutant TDP-43 gene is expressed in the host cell, in other words, the promoter is operably linked to the gene.

Specifically, examples of promoters operable in a central nervous system cell include, but not limited to, Thy-1 promoter (brain-specific), Neuron-Specific Enolase promoter (brain-specific), Tα1 promoter (brain-specific), promoters for central nerve cells such as a prion promoter (brain-specific), and known promoters for various cells that may exist in the central nervous system such as a glial cell. The promoter operable in a central nervous system cell may have both of the function as a promoter for a central nerve cell and the function as a promoter for various cells that may exist in the central nervous system. In addition, examples of promoters operable in a peripheral nervous system cell include, but not limited to, promoters known for peripheral nerve cells, and promoters known for various cells that may exist in the peripheral nervous system. While the promoters known for central nerve cells listed above may similarly be used as the promoters known for peripheral nerve cells, the promoters known for various cells that may exist in the central nervous system may similarly be used as the promoters known for various cells that may exist in the peripheral nervous system. A promoter operable in a peripheral nervous system cell may have both functions as a promoter for peripheral nerve cells and as a promoter for various cells that may exist in the peripheral nervous system. Furthermore, examples of promoters operable in a neuroblast include known promoters such as a CMV promoter.

A mutant TDP-43 gene inserted into an expression vector may, for example, be prepared as described below.

Specifically, first, a wild-type TDP-43 gene fragment is obtained from a human cDNA gene library by a method such as PCR. This gene fragment is used to screen for wild-type TDP-43 gene. If necessary, wild-type TDP-43 gene may be linked with DNA coding for an epitope tag or the like. The screened wild-type TDP-43 gene may be inserted into an appropriate plasmid vector by a recombinant DNA technique. Alternatively, instead of the above-described screening, a commercially available plasmid vector in which wild-type TDP-43 gene has already been inserted may be used.

The nucleotide sequence information of wild-type human TDP-43 gene (SEQ ID NO:1) may readily be obtained from known database, and, for example, disclosed as "Accession number: NM_007375" in GenBank database provided by the National Center for Biotechnology Information (NCBI) (website: http://www.ncbi.nlm.nih.gov). In SEQ ID NO:1, since the coding region (CDS) of wild-type human TDP-43 is 135-1379, this coding region can be used instead of the full-length sequence represented by SEQ ID NO:1.

Next, the nucleotide sequence of wild-type TDP-43 gene is modified to obtain a mutant TDP-43 gene coding for a mutant TDP-43. Here, the term a "mutant TDP-43" as used with the present invention refers to a protein having an activity of forming an intracellular inclusion. The phrase "an activity of forming an intracellular inclusion" refers to an activity of the mutant TDP-43 to aggregate by themselves, that is, to aggregate with each other as primary components to form an inclusion in a cell (in a cytoplasm or in a nucleus) (for example, the rate, number and size of intracellularly formed inclusions). This activity may be applicable as long as it gives a higher degree of mutant TDP-43 aggregation as compared to that of wild-type TDP-43 which is originally unlikely to aggregate to form an inclusion.

Specifically, preferable examples of mutant TDP-43 according to the present invention include the following proteins of (1a)-(1d).

(1a) A protein having an amino acid sequence obtained by deleting amino acids 78-84 from the amino acid sequence of wild-type TDP-43 (SEQ ID NO:2; GenBank database "Accession number: NM_031214").

(1b) A protein having an amino acid sequence obtained by deleting amino acids 187-192 from the amino acid sequence of wild-type TDP-43 (SEQ ID NO:2).

(1c) A protein having an amino acid sequence obtained by deleting amino acids 78-84 and amino acids 187-192 from the amino acid sequence of wild-type TDP-43 (SEQ ID NO:2).

(1d) A protein that has an amino acid sequence having one or a few (preferably about 1-10, and more preferably about 1-5) amino acids deleted from, substituted in or added to the amino acid sequence (1a), (1b) or (1c) and that has an activity of forming an intracellular inclusion.

Preferable examples of mutant TDP-43 according to the present invention also specifically include the following proteins of (2a)-(2d).

(2a) A protein having an amino acid sequence including amino acids 162-414 of the amino acid sequence of wild-type TDP-43 (SEQ ID NO:2).

(2b) A protein having an amino acid sequence including amino acids 218-414 of the amino acid sequence of wild-type TDP-43 (SEQ ID NO:2).

(2c) A protein having an amino acid sequence including amino acids 1-161 of the amino acid sequence of wild-type TDP-43 (SEQ ID NO:2).

(2d) A protein that has an amino acid sequence having one or a few (preferably about 1-10, and more preferably about 1-5) amino acids deleted from, substituted in or added to the amino acid sequence (2a), (2b) or (2c) and that has an activity of forming an intracellular inclusion.

Each of the proteins of (2a)-(2d) above may be defined as a protein that contains a wild-type TDP-43 fragment, but they are not limited in that each of them may be a protein that consist of this fragment only or may be a fusion protein with other protein (for example, a reporter protein such as GFP). A gene coding for such a fusion protein may readily be constructed by those skilled in the art based on known nucleotide sequence information and gene recombination technique.

Preferably, the "mutant TDP-43" used with the present invention does not have an activity of skipping exon 9 of cystic fibrosis transmembrane conductance regulator (CFTR) gene (SEQ ID NO:16; GenBank Accession number: NM_000492), a gene responsible for cystic fibrosis. Conventionally, an activity of skipping CFTR exon 9 has been reported as a function of wild-type TDP-43 (Buratti E et al., EMBO J., 2001 (ibid.)). Since a mutant TDP-43 of the present invention, in particular any of the proteins of (1a)-(1d) and (2a)-(2d) above, does not have such a skipping activity, there appears to be high association between formation of intracellular TDP-43 inclusions and deterioration of TDP-43 function. In the nucleotide sequence of CFTR gene (NM_000492) represented by SEQ ID NO:16, the exon 10 region corresponds to the exon 9 region in "Buratti E et al., EMBO J., 2001 (ibid.)". Thus, "exon 9 skipping activity" according to the specification of the present application is used, for convenience sake, in the same meaning as the notation (name) used in "Buratti E et al., EMBO J., 2001 (ibid.)", and thus when used based on the nucleotide sequence represented by SEQ ID NO:16, it substantially refers to an "exon 10 skipping activity". In this regard, the same applies to the entire specification, claims and drawings of the present application. The above-mentioned exon 10 is a nucleotide sequence consisting of nucleotides 1342-1524 of the nucleotide sequence represented by SEQ ID NO:16.

A gene coding for the above-described mutant TDP-43 (a mutant TDP-43 gene) may be prepared according to site-directed mutagenesis, for example, described in "Molecular Cloning, A Laboratory Manual 2nd ed., Cold Spring Harbor Laboratory Press (1989), Current Protocols in Molecular Biology, John Wiley and Sons (1987-1997)" or the like. Specifically, the gene may be prepared by using a mutagenesis kit utilizing a site-directed mutagenesis by a known technique such as Kunkel method or Gapped duplex method, where preferable examples of such kits include QuickChange™ Site-Directed Mutagenesis Kit (Stratagene), GeneTailor™ Site-Directed Mutagenesis System (Invitrogen), and TaKaRa Site-Directed Mutagenesis System (Mutan-K, Mutan-Super Express Km, etc.: Takara Bio).

A mutant TDP-43 gene may also be prepared by performing PCR as described in the examples below under suitable conditions by using DNA containing a nucleotide sequence encoding wild-type TDP-43 as a template and by designing primers for amplifying the gene. A DNA polymerase used for PCR is not limited to but preferably a highly accurate DNA polymerase and, for example, Pwo DNA polymerase (Roche Diagnostics), Pfu DNA polymerase (Promega), Platinum Pfx DNA polymerase (Invitrogen), KOD DNA polymerase (Toyobo), KOD-plus-polymerase (Toyobo) and the like. The reaction conditions for PCR may appropriately be determined according to the optimal temperature of the DNA polymerase used, the length and the types of DNA to be synthesized and the like. For example, in terms of cycle conditions, total of 20-200 cycles of: "90-98° C. for 5-30 seconds (denaturing/dissociation); 50-65° C. for 5-30 seconds (annealing); and 65-80° C. for 30-1,200 seconds (synthesis/elongation)" is preferable.

Furthermore, according to the present invention, a gene may be used that hybridizes with a nucleotide sequence complementary to the nucleotide sequence of the mutant TDP-43 gene obtained as described above or a nucleotide sequence of a coding region thereof under stringent conditions, and that codes for a protein having an activity of forming an intracellular inclusion. Examples of "stringent conditions" include a salt concentration of 100-900 mM, preferably 100-300 mM, and a temperature of 50-70° C., preferably 55-65° C. upon washing in the hybridization process. For detailed procedure of the hybridization method, reference may be made to "Molecular Cloning, A Laboratory Manual 2nd ed." (Cold Spring Harbor Laboratory Press (1989), "Current Protocols in Molecular Biology" (John Wiley and Sons (1987-1997)) or the like. Examples of the DNA to be hybridized include DNA containing a nucleotide sequence having at least 50% or higher, preferably 70%, more preferably 80%, and still more preferably 90% (e.g., 95% or higher or even 99%) identity with the complementary sequence thereof.

A transformed cell of the present invention is characterized by expressing a mutant TDP-43 where selection of the clone to be expressed, and detection and quantification of expression of the protein of interest may be carried out by a known method such as a Western blot method.

A transformed cell of the present invention is capable of forming an intracellular (intracytoplasmic or intranuclear) inclusion simply by expressing a mutant TDP-43, but in some cases, a cell expressing a mutant TDP-43 is also comprised whose formation of an inclusion may be recognized only after treatment with a proteasome inhibitor. Examples of the proteasome inhibitor used with the present invention include, but not limited to, MG132, lactacystin, TEAL and MG115.

A transformed cell of the present invention preferably contains inclusions similar to the intracellular (intracytoplasmic or intranuclear) inclusions found in the brain of a human patient suffering from a neurodegenerative disease such as FTLD or ALS, and thus it is extremely useful as a cell model for developing a therapeutic drug or a therapeutic method for a neurodegenerative disease.

3. METHOD FOR SCREENING THERAPEUTIC DRUG OR THE LIKE FOR NEURODEGENERATIVE DISEASE

The present invention can provide a method for screening a therapeutic drug for a neurodegenerative disease by using the transformed cell described in item 2. above, and the therapeutic drug for the neurodegenerative disease obtained by this method. Specifically, the screening method comprises the steps of: causing the transformed cell of the present invention to make contact with a candidate substance to determine the cellular activity of the cell; and screening a therapeutic drug for a neurodegenerative disease by using the obtained measurement result as an indicator. According to this screening method, examples of the neurodegenerative diseases include, but not limited to, frontotemporal lobar degeneration, amyotrophic lateral sclerosis, Alzheimer's disease, Parkinson's disease, Huntington's chorea and prion disease, and in particular, preferable examples include diseases associated with formation of an intracellular TDP-43 inclusion (diseases associated with intracellular TDP-43 accumulation).

Here, the cellular activities of the transformed cell of the present invention are not limited and examples include various activities involved in the functions, properties or the like of the transformed cell. A known method may be employed for measuring such various activities. In the above-described screening method, a preferable cellular activity to be measured is, for example, neurite elongation capability, viability, proliferation capacity, and the rate, number and size of intracellular mutant TDP-43 inclusions (activity of forming intracellular mutant TDP-43 inclusions).

For example, in the case where the transformed cell of the present invention is derived from a nerve cell such as a cranial nerve cell or a neuroblast, if the transformed cell that has been caused to make contact with a candidate substance is assessed to have a higher elongation rate (elongation speed) than that of a cell that did not make contact with the candidate substance based on the result of determining neurite elongation capability, the candidate substance may be selected as a therapeutic drug for a neurodegenerative disease.

Furthermore, if a transformed cell of the present invention that has been caused to make contact with a candidate substance is assessed to have a higher proliferation rate (proliferation speed) than that of a cell that did not make contact with the candidate substance based on the result of determining the proliferation capacity, the candidate substance may be selected as a therapeutic drug for a neurodegenerative disease. Similarly, if a transformed cell of the present invention that has been caused to make contact with a candidate substance is assessed to have a longer lifetime or higher viability than those of a cell that did not make contact with the candidate substance based on the result of determining the survival capacity, the candidate substance may be selected as a therapeutic drug for a neurodegenerative disease.

In addition, when a transformed cell of the present invention that has been caused to make contact with a candidate substance is assessed to have lower formation rate than that of a cell that did not make contact with the candidate substance based on the result of determining a formation rate (with reference to the number of cells) of intracellular inclusions whose primary component is a mutant TDP-43, the candidate substance may be selected as a therapeutic drug for a neurodegenerative disease. Similarly, when a transformed cell of the present invention that has been caused to make contact with a candidate substance is assessed to have less number of intracellular inclusions formed per cell than that of a cell that did not make contact with the candidate substance based on the result of determining the number of intracellular inclusions formed per cell, the candidate substance may be selected as a therapeutic drug for a neurodegenerative disease. Likewise, when a transformed cell of the present invention that has been caused to make contact with a candidate substance is assessed to have a smaller size as compared to a cell that did not make contact with the candidate substance from the beginning or unlikely to increase its size based on the measurement of the size of the intracellular inclusions, the candidate substance may be selected as a therapeutic drug for a neurodegenerative disease.

On the other hand, the present invention can also provide a method for screening an agent for suppressing formation of an intracellular mutant TDP-43 inclusion by using the transformed cell described in item 2. above, as well as an agent for suppressing formation of an intracellular mutant TDP-43 inclusion obtained by this method. Specifically, the screening method comprises the steps of causing the transformed cell of the present invention to make contact with a candidate substance to determine the activity of forming an inclusion (substantially, the activity of suppressing this formation) in the cell; and screening an agent for suppressing formation of an intracellular mutant TDP-43 inclusion by using the obtained measurement result as an indicator. According to this screening method, the activity of the mutant TDP-43 to form the intracellular inclusion is preferably determined based on the rate, number and size of the intracellular inclusions.

When a transformed cell of the present invention that has been caused to make contact with a candidate substance is assessed to have lower formation rate than that of a cell that did not make contact with the candidate substance based on the result of determining a formation rate (with reference to the number of cells) of the intracellular inclusions whose primary component is a mutant TDP-43, the candidate substance may be selected as an agent for suppressing inclusion formation. Similarly, when a transformed cell of the present invention that has been caused to make contact with a candidate substance is assessed to have less number of intracellular inclusions formed per cell than that of a cell that did not make contact with the candidate substance based on the result of determining the number of intracellular inclusions formed per cell, the candidate substance may be selected as an agent for suppressing inclusion formation. Likewise, when a transformed cell of the present invention that has been caused to make contact with a candidate substance is assessed to have a smaller size at the first place or unlikely to increase its size as compared to a cell that did not make contact with the candidate substance based on the measurement of the size of the intracellular inclusions, the candidate substance may be selected as an agent for suppressing inclusion formation.

4. METHOD FOR ASSESSING SIDE-EFFECT

The present invention can provide a method for assessing a side-effect of a therapeutic drug for a neurodegenerative disease by using the transformed cell described in item 2. above. Specifically, this assessing method comprises the steps of: causing the transformed cell of the present invention to make contact with a therapeutic drug for a neurodegenerative disease to determine a cellular activity of the cell; and assessing a side-effect of the therapeutic drug for a neurodegenerative disease by using the obtained measurement result as an indicator. According to this assessing method, examples of the neurodegenerative diseases include frontotemporal lobar degeneration, amyotrophic lateral sclerosis, Alzheimer's disease, Parkinson's disease, Huntington's chorea and prion disease, and in particular, preferable examples include diseases associated with formation of intracellular TDP-43 inclusions (diseases associated with intracellular TDP-43 accumulation).

Here, the cellular activities of the transformed cell of the present invention are not limited and examples include various activities involved in the functions, properties or the like of the transformed cell. A known method may be employed for determining such various activities. In the above-described assessing method, a preferable cellular activity to be determined is, for example, neurite elongation capability, proliferation capacity and viability.

For example, in the case where the transformed cell of the present invention is derived from any of various nerve cells such as a cranial nerve cell or a neuroblast, when the transformed cell that has been caused to make contact with a therapeutic drug for a neurodegenerative disease is assessed to have an equivalent or higher elongation rate (elongation speed) as compared to that of a cell that did not make contact with the therapeutic drug based on the result of determining neurite elongation capability, the therapeutic drug may be judged to have no side-effect.

Furthermore, if a transformed cell of the present invention that has been caused to make contact with a therapeutic drug for a neurodegenerative disease is assessed to have an equivalent or higher proliferation rate (proliferation speed) as compared to that of a cell that did not make contact with the therapeutic drug based on the result of determining the proliferation capacity, the therapeutic drug may be judged to have no side-effect. Similarly, if a transformed cell of the present invention that has been caused to make contact with a therapeutic drug for a neurodegenerative disease is assessed to have an equivalent or longer lifetime or higher viability as compared to those of a cell that did not make contact with the therapeutic drug based on the result of determining the survival capacity, the therapeutic drug may be judged to have no side-effect.

5. PHARMACEUTICAL COMPOSITION FOR TREATMENT AND PROPHYLAXIS

As described above, a pharmaceutical composition of the present invention for treating and/or preventing a neurodegenerative disease is a pharmaceutical composition characterized by comprising a low-molecular compound such as methylene blue and/or dimebon as an active element. Since methylene blue and dimebon can effectively suppress formation of intracellular TDP-43 inclusions against a neurodegenerative disease such as frontotemporal lobar degeneration or amyotrophic lateral sclerosis, in particular a neurodegenerative disease associated with formation of intracellular TDP-43 inclusions, they are useful for treating and preventing the disease.

The present invention comprises a method for treating and/or preventing a neurodegenerative disease by administering methylene blue and/or dimebon to a test subject (a patient suffering from or at risk of a neurodegenerative disease or a healthy person). The present invention also comprises use of methylene blue and/or dimebon for producing an agent for treating and/or preventing a neurodegenerative disease, and further provides a kit for treating and/or preventing a neurodegenerative disease comprising methylene blue and/or dimebon.

For a pharmaceutical composition or the like of the present invention, other than methylene blue and dimebon, a low-molecular compound such as exifone, gossypetin or congo red may also be used as an active element having an effect of suppressing formation of intracellular TDP-43 inclusions.

(1) Proportion of Active Element

The proportion of methylene blue and dimebon as an active element in the pharmaceutical composition of the present invention is not particularly limited. For example, in the case of a pharmaceutical composition for treating a neurodegenerative disease (a therapeutic drug for a neurodegenerative disease), methylene blue is preferably 0.01-30 wt %, more preferably 0.05-20 wt % and still more preferably 0.1-10 wt %, whereas dimebon is preferably 0.01-30 wt %, more preferably 0.05-20 wt % and still more preferably 0.1-10 wt %. In addition, but without limitation, either one of methylene blue and dimebon may be used (single-agent treatment) or both may be used in combination (combination treatment) in the pharmaceutical composition of the present invention. When methylene blue and dimebon are used in combination, the total proportion of these active elements in the pharmaceutical composition of the present invention is preferably 0.01-30 wt %, more preferably 0.05-20 wt % and still more preferably 0.1-10 wt %.

(2) Other Elements

The pharmaceutical composition of the present invention may also contain, besides methylene blue and dimebon as an active element, other components without limitation as long as the effect of the present invention is not remarkably lowered. For example, it may contain those generally used in the course of producing an agent as described below.

(3) Usage and Dose

The pharmaceutical composition of the present invention may, for example, be administered into a body through known usage such as parenteral or oral usage without limitation but preferably through parenteral usage.

A formulation used for these usages (a parenteral agent, an oral agent or the like) may be prepared by a conventional technique by appropriately selecting and using an excipient, a filler, a bulking agent, a binder, a wetting agent, a disintegrant, a lubricant, a surfactant, a dispersant, a buffer, a preservative, a solubilizing adjuvant, an antiseptic agent, a flavoring agent, a soothing agent, a stabilizing agent, a tonicity agent or the like generally-used for agent production.

In general, a dose of a therapeutic or prophylactic pharmaceutical composition of the present invention may appropriately be set within a wide range according to age and weight of the administration target (patient), type and progress of the disease, administration route, number of administration (daily), administration period and the like in consideration of the proportion of the active element in the formulation.

Hereinafter, use of the pharmaceutical composition of the present invention as a parenteral or oral agent will be described more precisely.

When used as a parenteral agent, the form thereof is generally not limited, and may be any of, for example, intravenous injection (including infusion), intramuscular injection, intraperitoneal injection, subcutaneous injection, suppository and the like. For various injections, for example, it may be provided in a unit-dose ampoule or a multi-dose vial, or as lyophilized powder that is redissolved in a solution upon use. This parenteral agent may also contain various known excipients or additives besides the above-described active element according to various forms as long as the effect of the active element is not remarkably lowered. For example, for various injections, examples of such excipients or additives include water, glycerol, propylene glycol and aliphatic polyalcohol such as polyethylene glycol.

A dosage (daily) of a parenteral agent is not limited and for various injections, it is generally such that preferably 0.1-50 mg, more preferably 0.5-20 mg and still more preferably 1-10 mg of the above-described active element is given per weight (kg) of an application target (patient).

When used as an oral agent, it is generally not limited by its form, and may be any of, for example, a tablet, a capsule, granulated powder, powder, a pill, a lozenge, a liquid medication, a suspension agent, an emulsifier, syrup and the like, or a dried product that is redissolved upon use. This oral agent may also contain various known excipients or additives besides the above-described active element according to various forms as long as the effect of the active element is not remarkably lowered. Examples of such excipients or additives include a binder (syrup, gum arabic, gelatin, sorbitol, tragacanth, polyvinylpyrrolidone, etc.), a filler (lactose, sugar, cornstarch, potato starch, calcium phosphate, sorbitol, glycine, etc.), a lubricant (magnesium stearate, talc, polyethylene glycol, silica, etc.), a disintegrant (various starches, etc.) and a wetting agent (sodium lauryl sulfate, etc.).

A dosage (daily) of an oral agent is generally such that preferably 0.1-100 mg, more preferably 0.5-50 mg and still more preferably 1-10 mg of the above-described active element is given per weight (kg) of an application target (test subject; patient). A proportion of the active element in an oral agent is not limited and may appropriately be selected in view of daily number of administration.

Hereinafter, the present invention will be described in more details by means of examples, although the present invention should not be limited thereto.

Example 1

(1) Materials and Methods

Construction of Various Plasmid Vectors

A vector (pRc-CMV-TDP-43) having human TDP-43 gene (SEQ ID NO:1) inserted between NotI and ApaI sites downstream from the CMV promoter of pRc-CMV vector (see Buratti et al., EMBO J., 2001 (ibid.)) was used as a template to amplify the coding region of human TDP-43 gene by PCR. PCR was carried out with the following primer set and reaction solution composition under the following reaction conditions.

<Primer Set>

```
F primer:
                                    (SEQ ID NO: 3)
5'-CGGGATCC ATGTCTGAATATATTCGGGT-3'

R primer:
                                    (SEQ ID NO: 4)
5'-GCTCTAGA CTACATTCCCCAGCCAGAAG-3'
```

<Reaction Solution Composition>

| | |
|---|---|
| Template DNA (pRc-CMV-TDP-43; 100 μg/μl): | 1 μL |
| TaqDNA polymerase: | 1 unit |
| F primer (20 μM): | 1 μL |
| R primer (20 μM): | 1 μL |
| dNTP (2.5 mM each): | 5 μL |
| 10 × Buffer: | 5 μL |
| Sterile water: | Optimal amount (about 36 μL) |
| Total: | 50 μL |

<Reaction Conditions>

Total of 30 cycles of: "denaturing/dissociation at 95° C. for 30 seconds; annealing at 50° C. for 30 seconds; and synthesis/elongation at 72° C. for 120 seconds".

The amplified fragment obtained by the above-described PCR was inserted between BamHI and XbaI sites of MCS of pcDNA3 (+) vector (Invitrogen) to prepare pcDNA3-TDP43 WT vector.

Subsequently, using pcDNA3-TDP43 WT as a template and QuickChange Site-directed Mutagenesis Kit (Stratagene), plasmid vectors having a nucleotide sequence coding for a mutant TDP-43 that is deficient in nuclear localization signal (NLS1, amino acid residue numbers: 78-84, see FIG. 2), a nucleotide sequence coding for a mutant that is deficient in the nuclear localization signal homologous sequence (NLS2, amino acid residue numbers: 187-192, see FIG. 2) or a nucleotide sequence coding for both deficient mutants were prepared. The name and summary of each vector are listed below.

pcDNA3-TDP43 WT:
  that encodes wild-type TDP-43 (amino acid residue numbers: 1-414 (full-length)).
pcDNA3-TDP43-ΔNLS1:
  that encodes NLS1-deficient mutant (deficient in amino acid residue numbers: 78-84).
pcDNA3-TDP43-ΔNLS2:
  that encodes NLS2-deficient mutant (deficient in amino acid residue numbers: 187-192).
pcDNA3-TDP43-ΔNLS 1 &2:
  that encodes both NLS1- and NLS2-deficient mutants (deficient in amino acid residue numbers: 74-84 and 187-192).

Furthermore, plasmid vectors having nucleotide sequences coding for a fusion protein of wild-type TDP-43 or a part thereof and GFP were prepared. Specifically, first, pcDNA3-TDP43 WT was used as a template to amplify the entire or a desired part of the nucleotide sequence coding for wild-type TDP-43 by PCR. PCR was carried out using either one of the following primer sets and reaction solution composition under the following reaction conditions.

<Primer Sets>

For amplification of the nucleotide sequence coding for wild-type TDP-43 (amino acid residue numbers: 1-414)

F primer:
                                          (SEQ ID NO: 5)
5'-CCGCTCGAGCT ATGTCTGAATATATTCGGGTAACCGAA-3'

R primer:
                                          (SEQ ID NO: 6)
5'-CGGGATCC CTACATTCCCCAGCCAGAAG-3'

For amplification of a nucleotide sequence coding for a part of TDP-43 (amino acid residue numbers: 162-414)

F primer:
                                          (SEQ ID NO: 7)
5'-CCGCTCGAGCT ATGTCACAGCGACATATGA-3'

R primer:
                                          (SEQ ID NO: 6)
5'-CGGGATCC CTACATTCCCCAGCCAGAAG-3'

For amplification of a nucleotide sequence coding for a part of TDP-43 (amino acid residue numbers: 218-414)

F primer:
                                          (SEQ ID NO: 8)
5'-CCGCTCGAGCT ATGGATGTCTTCATCCCCA-3'

R primer:
                                          (SEQ ID NO: 6)
5'-CGGGATCC CTACATTCCCCAGCCAGAAG-3'

For amplification of a nucleotide sequence coding for a part of TDP-43 (amino acid residue numbers: 274-414)

F primer:
                                          (SEQ ID NO: 9)
5'-CCGCTCGAGCT GGAAGATTTGGTGGTAATCCA-3'

R primer:
                                          (SEQ ID NO: 6)
5'-CGGGATCC CTACATTCCCCAGCCAGAAG-3'

For amplification of a nucleotide sequence coding for a part of TDP-43 (amino acid residue numbers: 315-414)

F primer:
                                          (SEQ ID NO: 10)
5'-CCGCTCGAGCT GCGTTCAGCATTAATCCAGCCAT-3'

R primer:
                                          (SEQ ID NO: 6)
5'-CGGGATCC CTACATTCCCCAGCCAGAAG-3'

For amplification of a nucleotide sequence coding for a part of TDP-43 (amino acid residue numbers: 1-161)

F primer:
                                          (SEQ ID NO: 11)
5'-CCGCTCGAGCT ATGTCTGAATATATTCGGGTAACCGAA-3'

R primer:
                                          (SEQ ID NO: 12)
5'-CGGGATCC CTATACTTTCACTTGTGTTT-3'

For amplification of a nucleotide sequence coding for a part of TDP-43 (amino acid residue numbers: 1-217)

F primer:
                                          (SEQ ID NO: 11)
5'-CCGCTCGAGCT ATGTCTGAATATATTCGGGTAACCGAA-3'

R primer:
                                          (SEQ ID NO: 13)
5'-CGGGATCC CTACACATCCCCGTACTGAG-3'

For amplification of a nucleotide sequence coding for a part of TDP-43 (amino acid residue numbers: 1-273)

```
F primer:
                                        (SEQ ID NO: 11)
5'-CCGCTCGAGCT ATGTCTGAATATATTCGGGTAACCGAA-3'

R primer:
                                        (SEQ ID NO: 14)
5'-CGGGATCC CTAACTTCTTTCTAACTGTCTATTGCT-3'
```

For amplification of a nucleotide sequence coding for a part of TDP-43 (amino acid residue numbers: 1-314)

```
F primer:
                                        (SEQ ID NO: 11)
5'-CCGCTCGAGCT ATGTCTGAATATATTCGGGTAACCGAA-3'

R primer:
                                        (SEQ ID NO: 15)
5'-CGGGATCC CTAACCAAAGTTCATCCCACCACCCAT-3'
```

<Reaction Solution Composition>

| | |
|---|---|
| Template DNA (pcDNA3-TDP43 WT; 100 μg/μl): | 1 μL |
| TaqDNA polymerase: | 1 unit |
| F primer (20 μM): | 1 μL |
| R primer (20 μM): | 1 μL |
| dNTP (2.5 mM each): | 5 μL |
| 10 × Buffer: | 5 μL |
| Sterile water: | Optimal amount (about 36 μL) |
| Total: | 50 μL |

<Reaction Conditions>

Total of 30 cycles of: "denaturing/dissociation at 95° C. for 30 seconds; annealing at 55° C. for 30 seconds; and synthesis/elongation at 72° C. for 120 seconds".

Each of the amplified fragments obtained by the above-described PCR was inserted between BamHI and XhoI sites of MCS of pEGFP-C1 (Clontech; GenBank Accession number: U55763) to prepare plasmid vectors having nucleotide sequences coding for GFP-fused proteins. The name and summary of each vector are listed below.

GFP-TDP-43 WT:
  that encodes a fusion protein of GFP and wild-type TDP-43 (amino acid residue numbers: 1-414 (full-length)).
GFP-TDP 162-414:
  that encodes a fusion protein of GFP and a part of TDP-43 (amino acid residue numbers: 162-414).
GFP-TDP 218-414:
  that encodes a fusion protein of GFP and a part of TDP-43 (amino acid residue numbers: 218-414).
GFP-TDP 274-414:
  that encodes a fusion protein of GFP and a part of TDP-43 (amino acid residue numbers: 274-414).
GFP-TDP 315-414:
  that encodes a fusion protein of GFP and a part of TDP-43 (amino acid residue numbers: 315-414).
GFP-TDP 1-161:
  that encodes a fusion protein of GFP and a part of TDP-43 (amino acid residue numbers: 1-161).
GFP-TDP 1-217:
  that encodes a fusion protein of GFP and a part of TDP-43 (amino acid residue numbers: 1-217).
GFP-TDP 1-273:
  that encodes a fusion protein of GFP and a part of TDP-43 (amino acid residue numbers: 1-273).
GFP-TDP 1-314:
  that encodes a fusion protein of GFP and a part of TDP-43 (amino acid residue numbers: 1-314).

In order to analyze the function of TDP-43, a plasmid vector coding for a region including exon 9 of cystic fibrosis transmembrane conductance regulator (CFTR), i.e., a gene responsible for cystic fibrosis, and abutting introns thereof was prepared. Specifically, a nucleotide sequence region comprising total of 670 nucleotides beginning from nucleotide 221 on the upstream side of exon 10 (corresponding to exon 9 in "Buratti E et al., EMBO J., 2001 (ibid.)") in the nucleotide sequence (SEQ ID NO:16) of CFTR gene (GenBank Accession number: NM_000492) to nucleotide 266 on the downstream side of exon 10 (nucleotides 1130-1790 of the nucleotide sequence represented by SEQ ID NO:16) was amplified from chromosomal DNA derived from a healthy human by PCR. PCR was carried out using the following primer set and reaction solution composition under the following reaction conditions.

<Primer Set>

```
F primer:
                                        (SEQ ID NO: 17)
5'-CGGAATTC ACTTGATAATGGGCAAATATC-3'

R primer:
                                        (SEQ ID NO: 18)
5'-CCCTCGAG CTCGCCATGTGCAAGATACAG-3'
```

<Reaction Solution Composition>

| | |
|---|---|
| Template DNA (healthy human-derived chromosomal DNA; 100 μg/μl): | 1 μL |
| TaqDNA polymerase: | 1 unit |
| F primer (20 μM): | 1 μL |
| R primer (20 μM): | 1 μL |
| dNTP (2.5 mM each): | 5 μL |
| 10 × Buffer: | 5 μL |
| Sterile water: | Optimal amount (about 36 μL) |
| Total: | 50 μL |

<Reaction Conditions>

Total of 35 cycles of: "denaturing/dissociation at 95° C. for 30 seconds; annealing at 60° C. for 30 seconds; and synthesis/elongation at 72° C. for 120 seconds".

The amplified fragment obtained by the above-described PCR was inserted between EcoRI and XhoI sites of MCS of pSPL3 vector (GIBCO BRL; GenBank Accession number: U19867) to prepare pSPL3-CFTRex9 vector.

Cultivation of SH-SY5Y Cell and Integration of Plasmid Vector

Neuroblast SH-SY5Y was cultured in an incubator using DMEM/F12 medium containing 10% fetal bovine serum under conditions of 37° C. and 5% $CO_2$.

Each of the above-described various plasmid vectors (pcDNA3 or pEGFP system, 1 μg) was integrated into SH-SY5Y cell using FuGENE6 transfection reagent (Roche Diagnostics). FuGENE6 at 3-fold volume of the total plasmid amount was mixed with the plasmid, left to stand at room temperature for 15 minutes, and then mixed with the cell solution. The resultant was cultured for 2-3 days, and used for preparation of cell lysates or immunohistological staining.

Observation with Confocal Laser Microscope

SH-SY5Y cells cultured on glass covers were mixed with each of the various expression vectors (1 μg) and added in the presence of FuGENE6. After two days of cultivation, cell immobilization or protease inhibitor treatment was carried out. In the protease inhibitor treatment, a final concentration of 20 μM of MG132 (proteasome inhibitor) or carbobenzoxy-leucyl-leucinal (zLL: calpain inhibitor) was added to the cell, and cultured at 37° C. for 6 hours. Thereafter, the cell was immobilized in a 4% paraformaldehyde solution. The immobilized cell was treated with 0.2% Triton X-100, then blocked with 5% bovine serum albumin solution, and caused to react with a primary antibody at 37° C. for an hour. After washing with 50 mM Tris-HCl containing 0.05% Tween 20 and 150 mM NaCl (pH 7.5) (TBS-T), the cell was caused to react with a fluorescence-labeled secondary antibody at 37° C. for an hour. After washing with TBS-T, the cell was caused to react with TO-PRO-3 (Invitrogen, 3,000-fold diluted) at 37° C. for an hour for nuclear staining. The resultant was sealed on a glass slide, and then analyzed with a confocal laser microscope (Carl Zeiss).

The primary antibody and the fluorescence-labeled secondary antibody used were as follows.

Primary antibody:
anti-TARDBP (ProteinTech, 1:1000 dilution);
anti-pS409/410 (antibody (antibody that specifically binds to TDP-43 aggregates) obtained by using, as an antigen, a peptide in which Ser residues at positions 409 and 410 of TDP-43 are both phosphorylated, 1:500 dilution);
anti-ubiquitin (MAB1510, CHEMICON, 1:500 dilution)
Fluorescence-labeled secondary antibody:
FITC-labeled anti-rabbit IgG (anti-rabbit immunoglobulin, FITC-labeled, Product number: F9887, Sigma, 1:500 dilution);
rhodamine-labeled anti-mouse IgG (anti-mouse immunoglobulin, TRITC-labeled, Product number: T2402, Sigma, 1:500 dilution)

Among the above-mentioned primary antibodies, anti-pS409/410 antibody was prepared as follows.

(i) Preparation of Antigen

As an antigen, a peptide having a sequence in which the amino acids 405-414 of the amino acid sequence of human TDP-43 (SEQ ID NO:2) are added with cysteine at the N-terminal, and the serine residues are phosphorylated (CMDSKS(PO$_3$H$_2$)S(PO$_3$H$_2$)GWGM (SEQ ID NO:19)) was synthesized by a solid-phase process (Sigma-Genosys or ThermoQuest). Here, S(PO$_3$H$_2$) of this peptide represents a phosphorylated serine. In addition, a non-phosphorylated peptide (MDSKSSGWGM (SEQ ID NO:20); amino acid residue numbers 405-414 of the amino acid sequence represented by SEQ ID NO:2) was also synthesized for preparing columns and for use as a control.

(ii) Immunization

The synthesized peptide was conjugated with thyroglobulin or KLH according to a conventional method to be used as an antigen. 1 ml of 1 mg/ml antigen peptide saline solution containing the antigen peptide and 1 ml of complete Freund's adjuvant (Difco) was mixed together, emulsified by ultrasonic treatment, and used for immunization at multiple sites on the back of a rabbit (New Zealand white, weight 2.5 kg, female). Two weeks after the initial immunization, 0.5 ml of 1 mg/ml antigen peptide saline solution and 1 ml of incomplete Freund's adjuvant were mixed together, emulsified by ultrasonic treatment and used for booster. A week after the immunization, blood was collected, which was left to stand at room temperature for an hour and at 4° C. overnight, and subjected to centrifugation treatment at 5000×g for 10 minutes to obtain an antiserum.

(iii) Purification of Antibody

In order to purify the antibody, a column was prepared by reacting about 2 ml of formyl-cellulofine (Seikagaku Corporation) or Toyopearl AF Tresyl 650M (Tosoh Corporation) with about 2 mg of the nonphosphorylated synthetic peptide. 2 ml of antiserum was circulated in this column for 10-20 hours, and antibody that did not adsorb to the column was used as anti-phosphorylated TDP-43 antibody (anti-pS409/410).

Exon Skipping Assay

In order to examine the functions of various TDP-43 mutants, skipping assay for exon 9 of cystic fibrosis transmembrane conductance regulator (CFTR), i.e., a gene responsible for cystic fibrosis, was conducted. Cos7 cells seeded on a 6-well plate were mixed with 0.5 μg of pSPL3-CFTRex9 and 1 μg of an expression vector for various TPD-43 and added in the presence of FuGENE6. Subsequently, the resultant was directly subjected to two days of cultivation, and the cells were collected to prepare a sample according to the instruction attached to Exon Trapping System (GIBCO BRL), which was analyzed by electrophoresis using 1.3% agarose gel.

Suppression of Formation of Intracellular Inclusions by Addition of Low-Molecular Compound The cell used was human neuroblast cell line SH-SY5Y, while pEGFP-TDP 162-414 (GFP-TDP 162-414) and pcDNA3-TDP delta NLS1&2 (TDP delta NLS1&2) which gave more significant formation of intracellular inclusions among various TDP-43 mutants were used to search for an inhibitor for the above-described inclusion formation.

Gene transfection into SH-SY5Y cell was carried out according to the method described in "Cultivation of SH-SY5Y cell and integration of plasmid vector" above, where 1 μg of each of the various plasmids was transfected into the cell with three-fold volume of a transfection reagent (FuGENE6: 3 μl).

Treatment with a candidate inhibitor took place two hours after gene transfection. As candidate inhibitors, methylene blue and dimebon were examined. Methylene blue was dissolved in DMSO, and added to culture solutions to final concentrations of 0 μM, 0.05 μM and 0.1 μM, thereby initiating the treatment. Meanwhile, dimebon was dissolved in sterile water, and added to culture solutions to final concentrations of 0 μM, 20 μM and 60 μM, thereby initiating the treatment. The concentrations of methylene blue were determined to take the above concentrations by considering the concentration conditions that have no damage on cell proliferation. On the other hand, the concentrations of dimebon were determined by referring to a publication (Jun Wu et al., Molecular Neurodegeneration, 2008, vol. 3, p. 15), and the preparation method (suspension in sterile water) was carried out according to the instruction provided by the reagent supplier.

Three days after the addition of the candidate inhibitors, conditions of the cells were observed according to the method described in "Observation with confocal laser microscope" above. The cells three days after the candidate inhibitor treatment were immobilized with 4% paraformaldehyde, subjected to treatment for membrane permeation with 0.2% TritonX-100, blocked with 5% bovine serum albumin solution, and allowed to react with a primary antibody at 37° C. for an hour. After washing with 50 mM Tris-HCl containing 0.05% Tween 20 and 150 mM NaCl (pH 7.5) (TBS-T), the cell was caused to react with a fluorescence-labeled secondary antibody at 37° C. for an hour. After washing with TBS-T, the cell was caused to react with TO-PRO-3 (Invitrogen, 3,000-fold diluted) at 37° C. for an hour for nuclear staining. The resultant was sealed on a glass slide, and then analyzed with a confocal laser microscope (Carl Zeiss). The primary antibody and the fluorescence-labeled secondary antibody used in this case were as follows.

For pEGFP-TDP 162-414 (GFP-TDP 162-414)
Primary Antibody:
anti-pS409/410 (antibody (prepared by the present inventors, 1:500 dilution) that specifically binds to TDP-43 aggregates and that is obtained by using a peptide in which amino acid residues Ser 409 and 410 of TDP-43 are both phosphorylated as an antigen);
Fluorescence-Labeled Secondary Antibody:
Alexa-568-labeled anti-mouse IgG (1:500 dilution)
Observed Image with Confocal Laser Microscope:
TDP and phosphorylated TDP were confirmed in green (vector-derived GFP) and red, respectively.

For pcDNA3-TDP delta NLS1&2 (TDP delta NLS1&2)
Primary Antibody:
anti-pS409/410 (antibody (prepared by the present inventors, 1:500 dilution) that specifically binds to TDP-43 aggregates and that is obtained by using a peptide in which amino acid residues Ser 409 and 410 of TDP-43 are both phosphorylated as an antigen);
anti-ubiquitin (MAB1510, CHEMICON, 1:500 dilution)
Fluorescence-Labeled Secondary Antibody:
Fluorescein isothiocyanate (FITC)-labeled anti-rabbit IgG (Sigma, 1:500 dilution)
Alexa-568-labeled anti-mouse IgG (1:500 dilution)
Observed Image with Confocal Laser Microscope:
Phosphorylated TDP and ubiquitin were confirmed in green and red, respectively.

Figure 19:
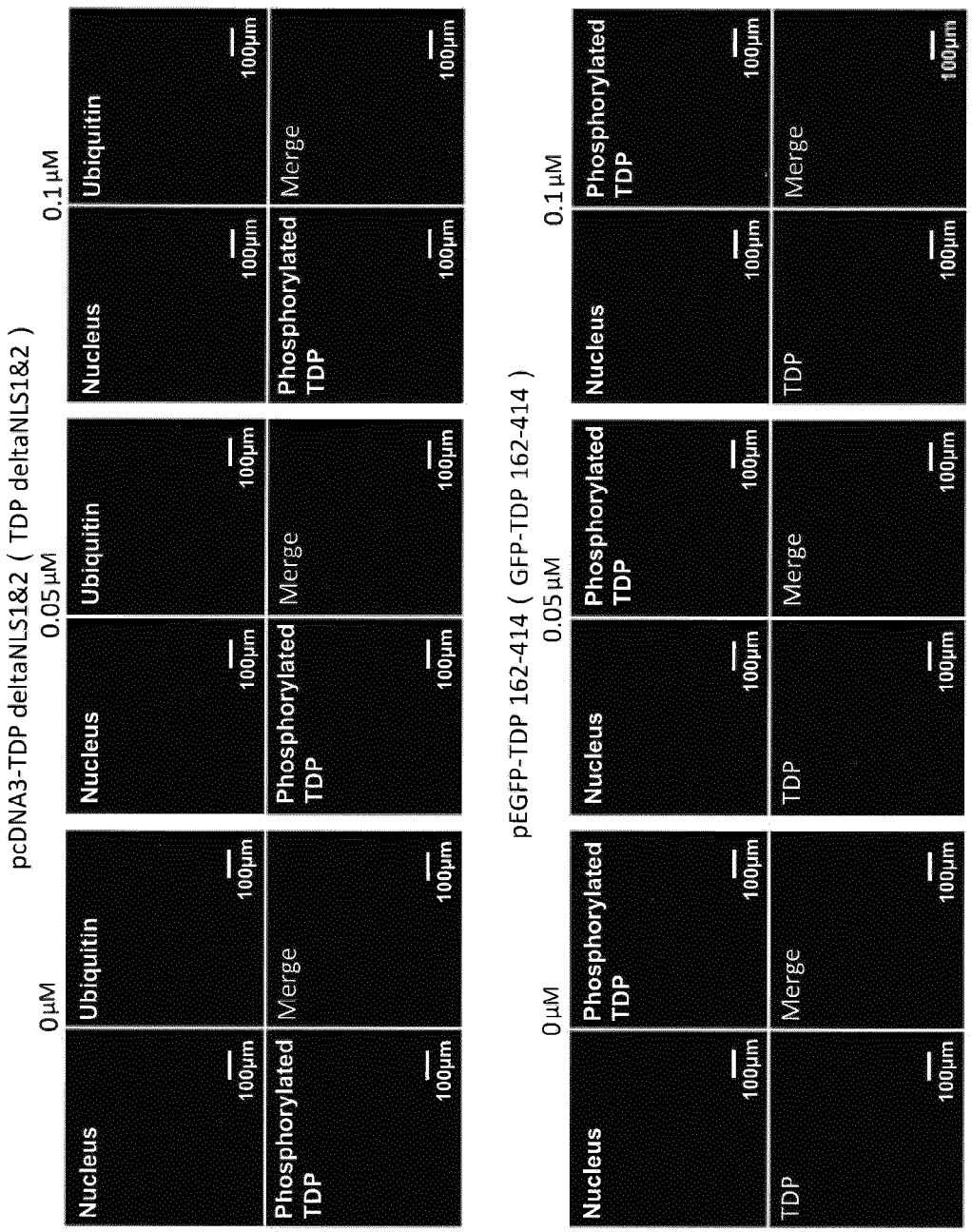
FIG. 19 shows the results from observing an effect of a low-molecular compound (methylene blue) to suppress formation of an intracellular TDP-43 inclusion with a confocal laser microscope. The upper sets of pictures are the results for TDP-43 delta NLS1&2 while the three sets of pictures below are the results for GFP-TDP 162-414.
Figure 21:
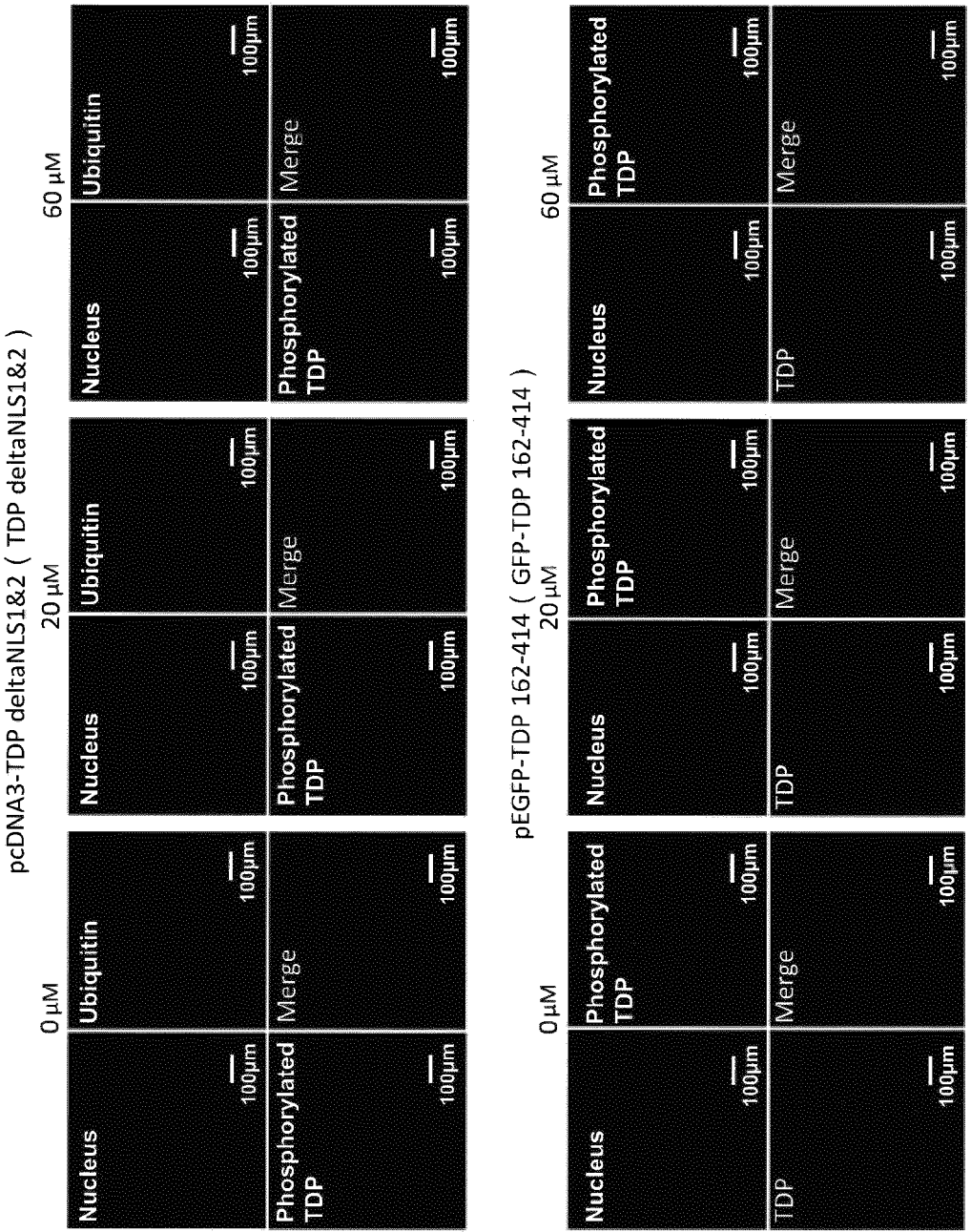
FIG. 21 shows the results from observing an effect of a low-molecular compound (dimebon) to suppress formation of an intracellular TDP-43 inclusion with a confocal laser microscope.

For microscopical visualization with a confocal laser microscope, laser output (green) was set such that only intracellular inclusions can be detected (FIGS. 19 and 21).

Figure 20:
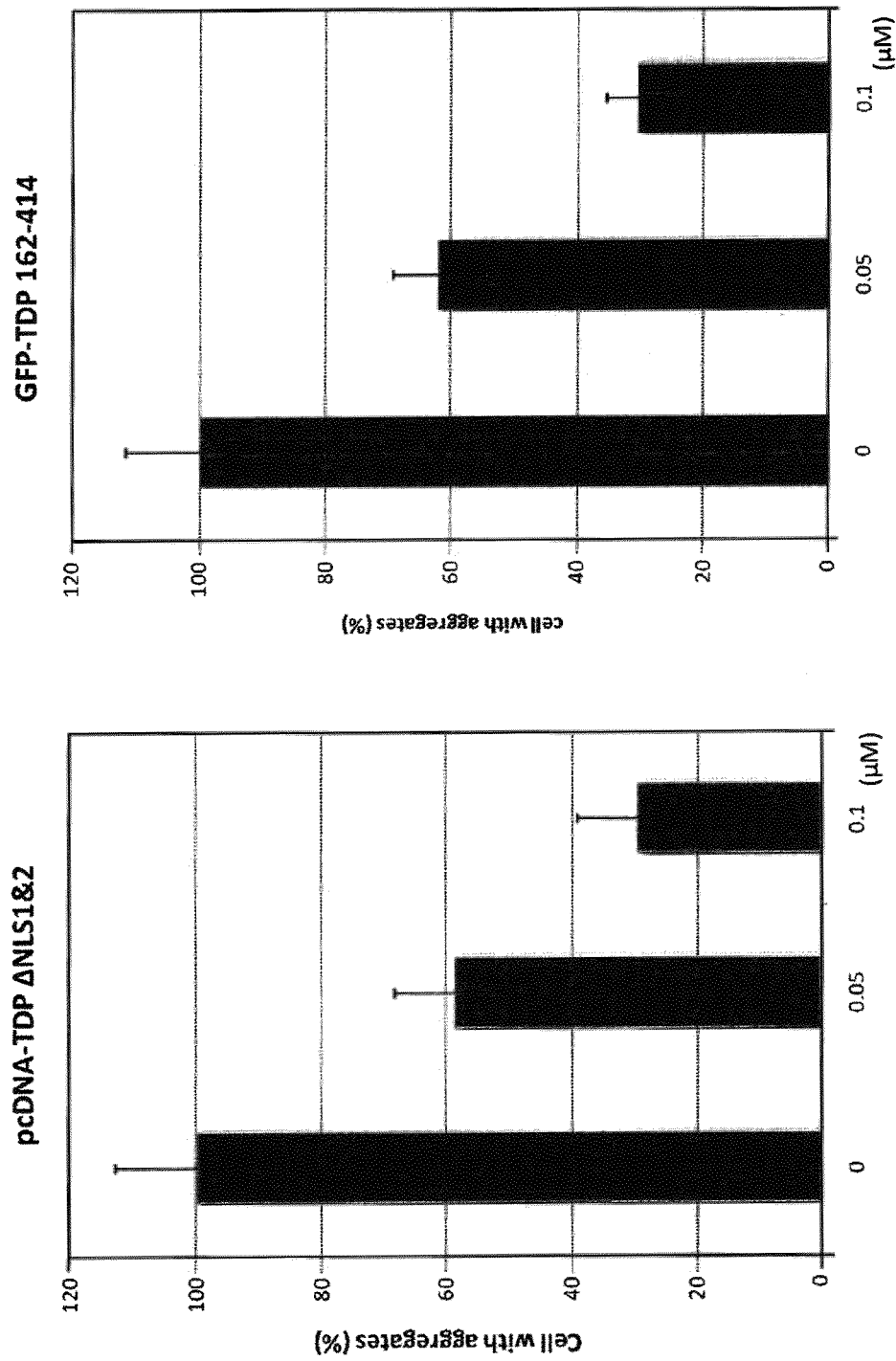
FIG. 20 shows the results from quantitating the percentage of the cells forming inclusions with respect to an effect of a low-molecular compound (methylene blue) to suppress formation of an intracellular TDP-43 inclusion. The left graph represents the results for TDP-43 delta NLS1&2 while the right graph represents the results for GFP-TDP 162-414. The horizontal and vertical axes in the graphs represent the concentrations of methylene blue and the percentage of cells forming intracellular TDP-43 inclusions, respectively.
Figure 22:
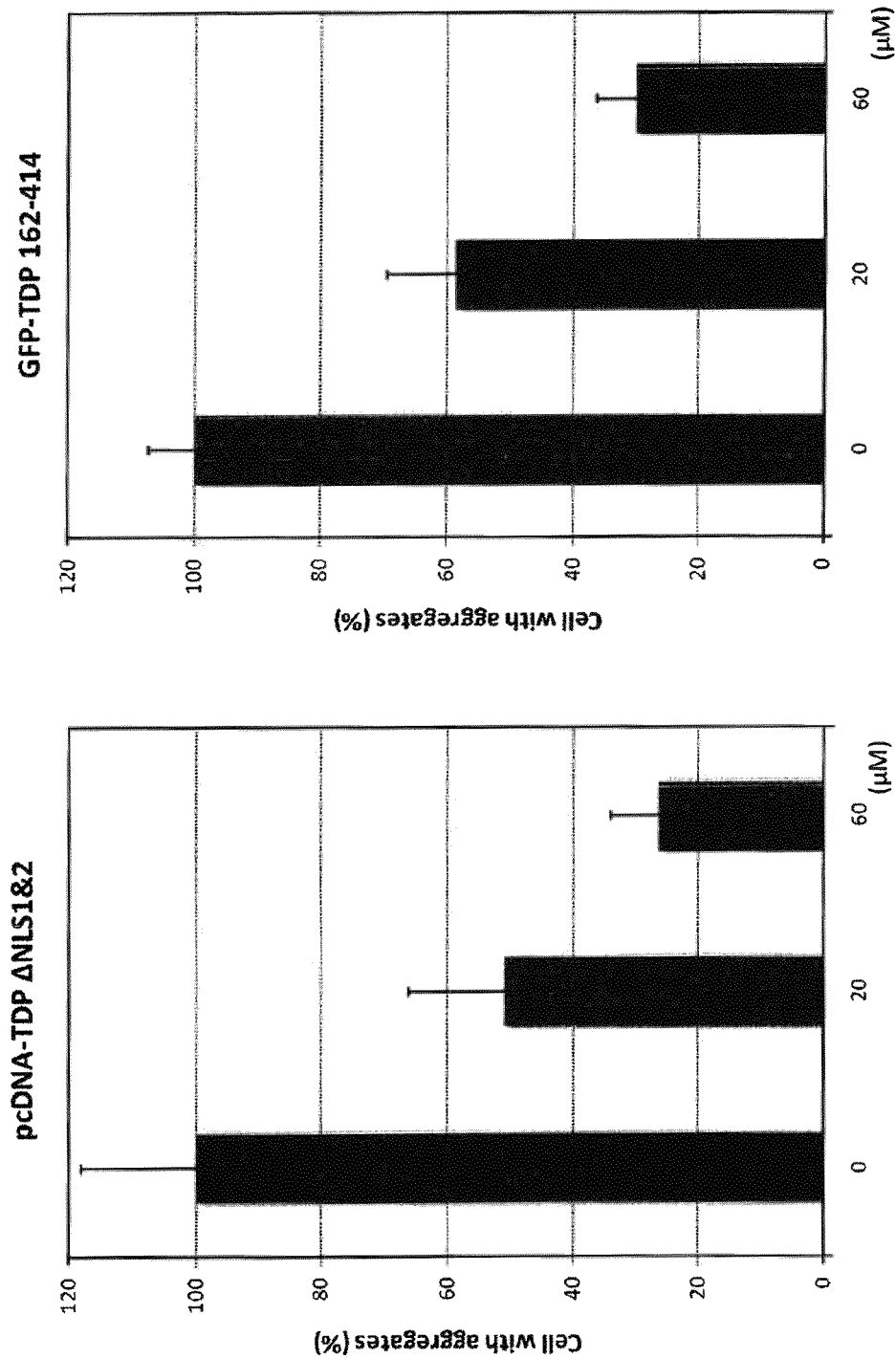
FIG. 22 shows the results from quantitating the percentage of the cells forming inclusions with respect to an effect of a low-molecular compound (dimebon) to suppress formation of an intracellular TDP-43 inclusion. The left graph represents the results for TDP-43 delta NLS1&2 while the right graph represents the results for GFP-TDP 162-414. The horizontal and vertical axes in the graphs represent the concentrations of dimebon and the percentage of cells forming intracellular TDP-43 inclusions, respectively.

For pcDNA3-TDP delta NLS1&2 (TDP delta NLS1&2), intensity of phosphorylated TDP (green) and intensity of TO-PRO-3 (blue) indicating the number of cells, and for pEGFP-TDP 162-414 (GFP-TDP 162-414), intensity of TDP (green) and intensity of TO-PRO-3 (blue) indicating the number of cells were each calculated using LSM5 Pascal v 4.0 software (Carl Zeiss) to determine the percentage of the number of cells with inclusion formation (green) to the number of entire cells (blue) (cells with aggregates (%)), and the results were represented by graphs. The results are shown in FIGS. 20 and 22 (single-agent treatment with methylene blue or dimebon), and FIGS. 23 and 24 (combination treatment with methylene blue and dimebon).

(2) Results and Discussion

Identification of Nuclear Localization Signal (NLS)

Figure 4:
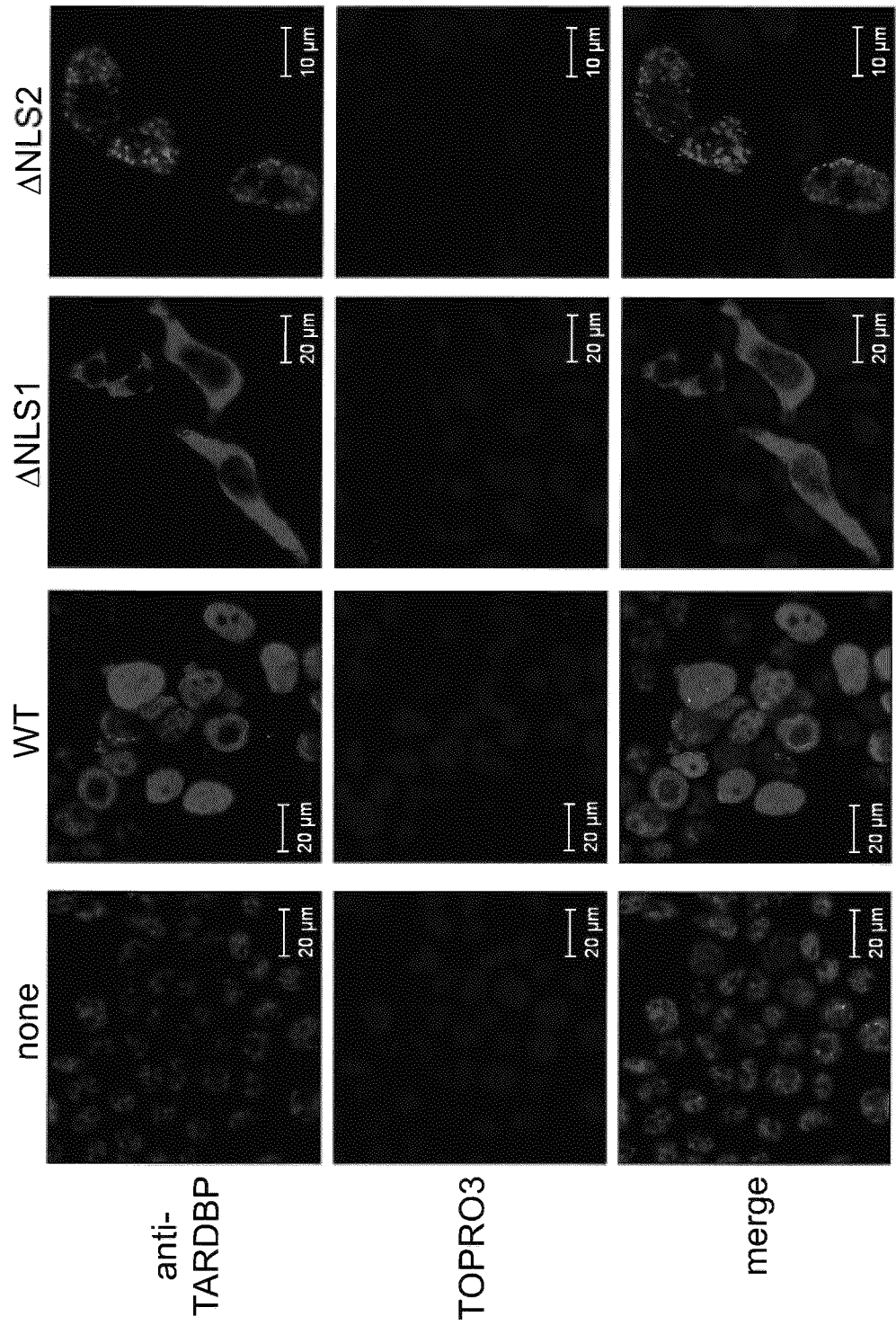
FIG. 4 shows the results from observing cells expressing various TDP-43 with a confocal laser microscope.

NLS of TDP-43 was identified. NLS is generally known as a sequence having a few continuous residues of basic amino acids (FIG. 3). A sequence present in T antigen of SV40 (PKKKRKV: SEQ ID NO:21) is the most known NLS, based on which a NLS sequence was searched from the amino acid sequence of TDP-43 (FIG. 2). As a result, candidate sequences were found at two sites (FIG. 2: NLS1 and NLS2). In order to identify NLS, mutants (ΔNLS1 and ΔNLS2) deficient in respective NLS candidate sequences (NLS1: residues 78-84, NLS2: residues 187-192) were prepared, which were transiently expressed in SH-SY5Y cells along with the wild-type for observation with a confocal laser microscope (FIG. 3). As a result, as shown in FIG. 4, while expression of the wild-type was found in the nuclear, expression of ΔNLS1 was not found in the nuclear but in the cytoplasm. Moreover, expression of ΔNLS2 was found in the nuclear but unlike the case of the wild-type, it was detected as a granular structure in the nucleus. From these facts, the amino acid sequence of NLS1 (FIG. 2) was found to be the nuclear localization signal. However, it was also found that intracellular inclusions were not formed by simply expressing any of the mutants including the wild-type by itself. In addition, it was also found that with a commercially available antibody (anti-TARDBP), not only the foreign TDP-43 brought about with a plasmid, but also endogenous TDP-43 originally present in the cell was also stained well (indicated as "none" in FIG. 4: transfection of pcDNA3 (+) vector itself).

Emergence of Intranuclear Inclusions

Next, wild-type TDP-43 and various deficient mutants were expressed in SH-SY5Y cells, and the expressed cells were treated with MG132 as a proteasome inhibitor for observation with a confocal laser microscope. The various plasmids were transfected into SH-SY5Y cells, incubated at 37° C. for 48 hours, added with 20 μM of MG132, and further incubated at 37° C. for 6 hours. The cells were immobilized and then stained with a commercially available TDP-43 polyclonal antibody (anti-TARDBP). As can be appreciated from FIG. 5, cells expressing wild-type TDP-43 and NLS1-deficient mutant did not show significant difference from MG132-free cases (FIG. 5: upper panels), but in NLS2-deficient mutant-expressing cell, inclusions were found in the nucleus by MG132 treatment. When treatment was also performed with calpain inhibitor, i.e., zLL, that has similar structure to that of MG132, no particular change was found in the expression pattern (data not shown).

Figure 6:
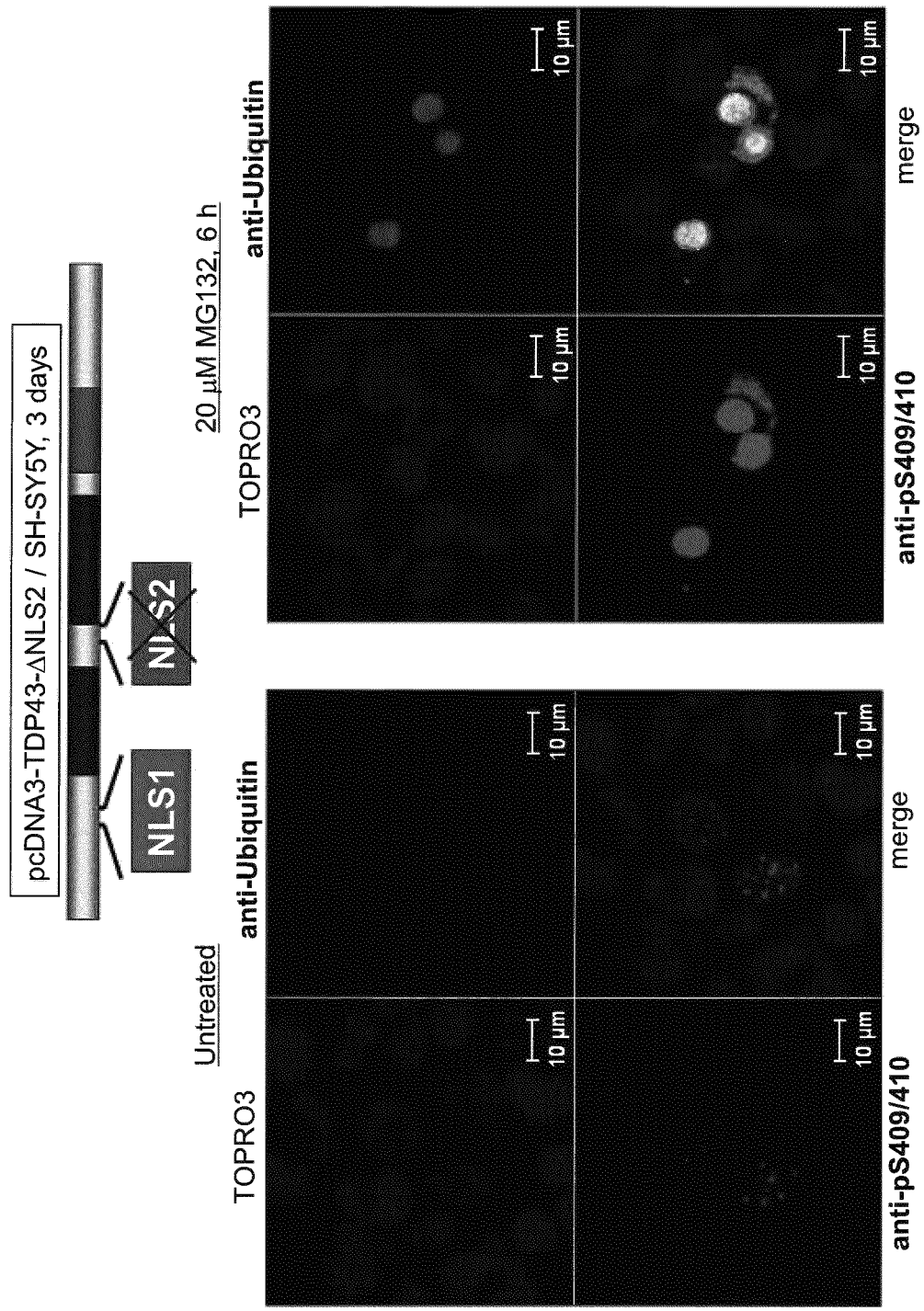
FIG. 6 shows the effects of the presence and absence of a treatment with a proteasome inhibitor (MG132) on ΔNLS1-expressing cells. The pictures are stained images obtained with anti-phosphorylated TDP-43 antibody (anti-pS409/410) and anti-ubiquitin antibody (anti-ubiquitin).

For the purpose of examining whether or not these intranuclear inclusions have the same properties as those of the intranuclear inclusions found in FTLD or ALS patient's brain, staining was performed with the above-described phosphorylated TDP-43-specific antibody. (anti-pS409/410) and anti-ubiquitin antibody (anti-ubiquitin) for observation with a confocal laser microscope. As a result, an intranuclear granular structure positive to anti-pS409/410 antibody was detected in the non-MG132-treated sample while no staining was found with anti-ubiquitin (FIG. 6: left panels). From these results, it was again confirmed that anti-pS409/410, i.e., phosphorylated TDP-43-specific antibody, does not detect endogenous TDP-43 present in normal cells at all. On the other hand, emergence of intranuclear inclusions positive to both anti-pS409/410 and anti-ubiquitin whose diameter was about 10 μm was confirmed in the MG132-treated sample (FIG. 6: right panels). From this result, it was found that, similar to intranuclear inclusions found in the FTLD or ALS patient's brain (FIG. 1: left panel), MG132-treated intranuclear inclusions that emerge in the NLS2-deficient mutant-expressing cells were phosphorylated and ubiquitinated, and their sizes were generally the same.

Emergence of Cytoplasmic Inclusions

Figure 5:
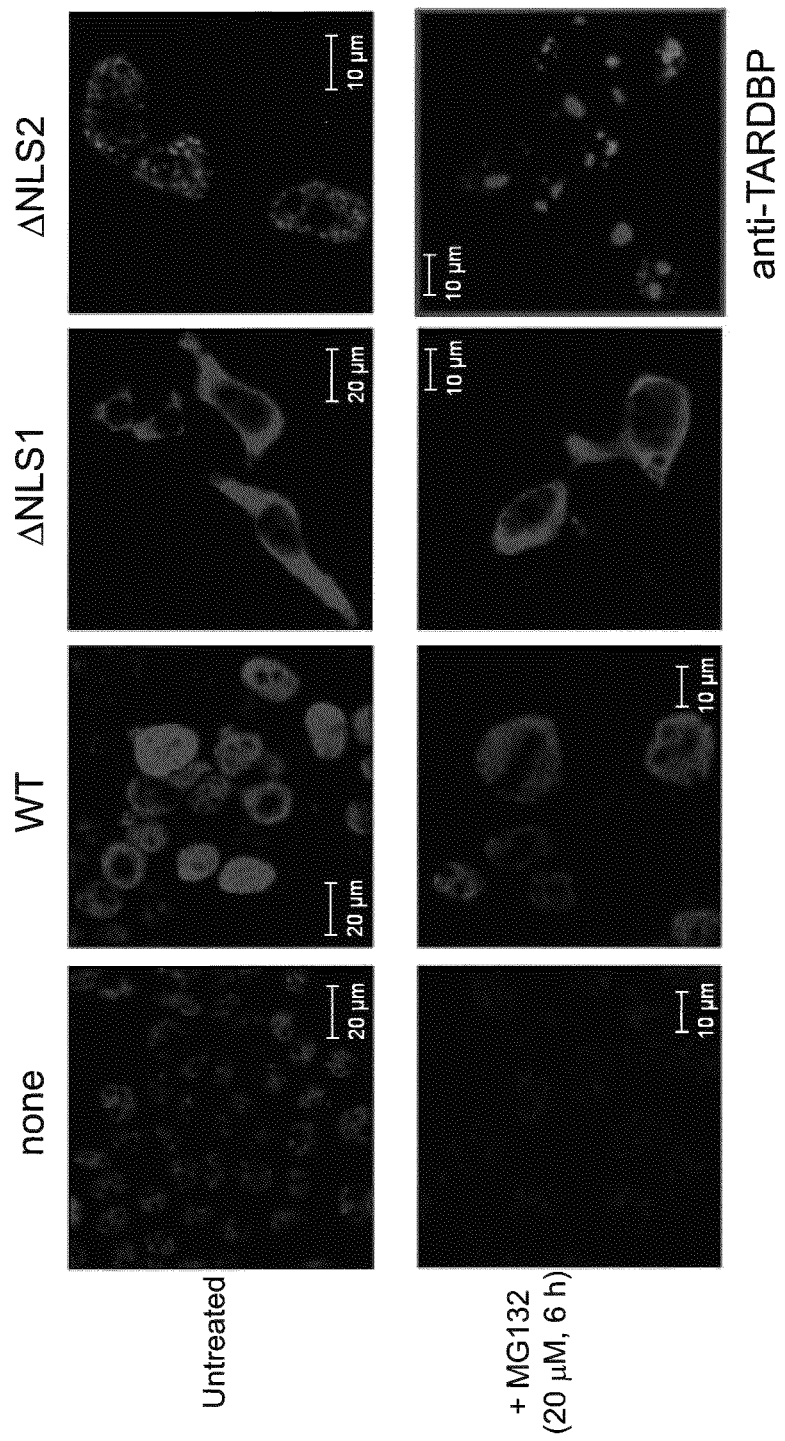
FIG. 5 shows the effects of the presence and absence of a treatment with a proteasome inhibitor (MG132) on various TDP-43-expressing cells. The pictures are stained images obtained with a commercially available antibody (anti-TARDBP).
Figure 7:
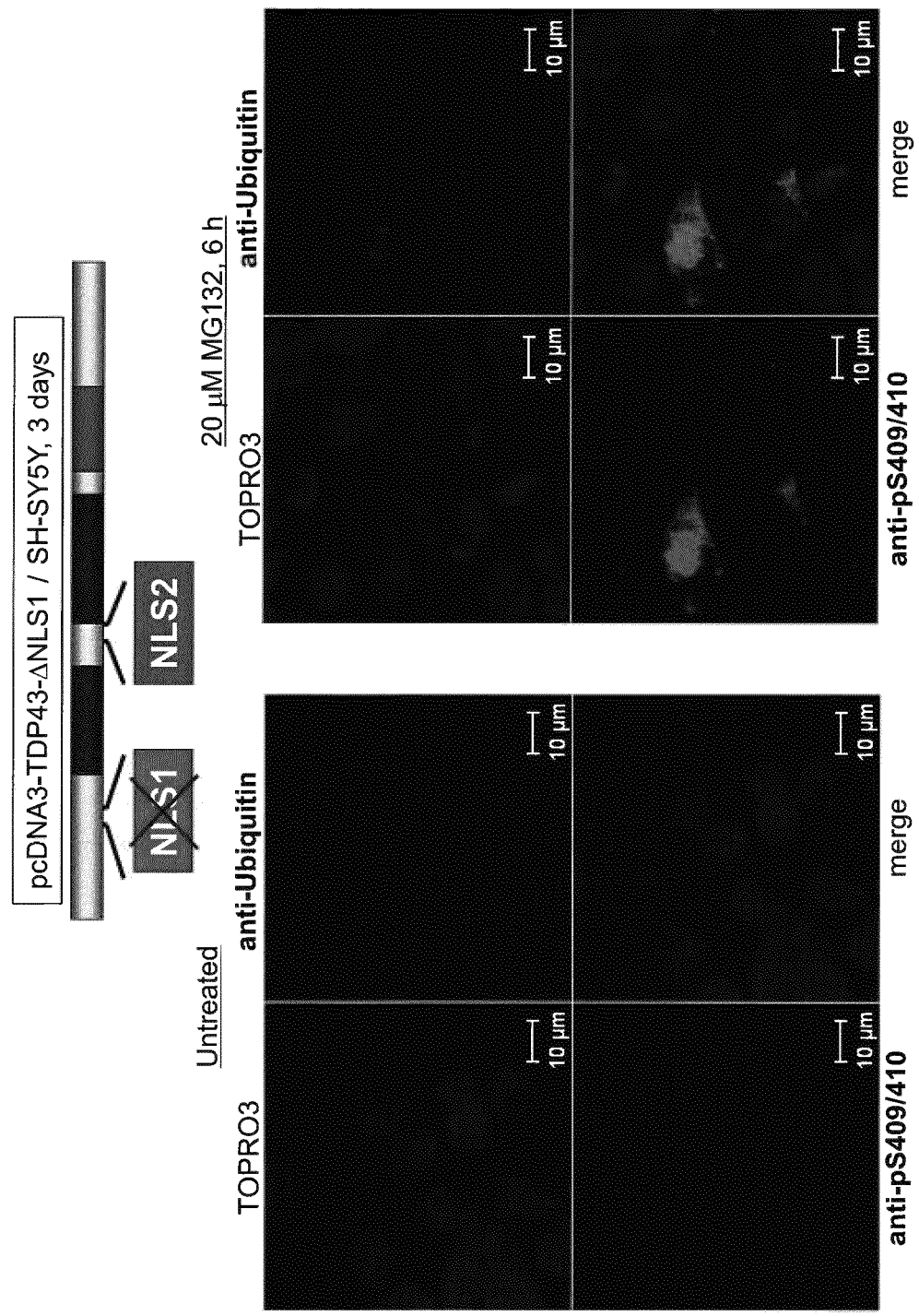
FIG. 7 shows the effects of the presence and absence of a treatment with a proteasome inhibitor (MG132) on ΔNLS2-expressing cells. The pictures are stained images obtained with anti-phosphorylated TDP-43 antibody (anti-pS409/410) and anti-ubiquitin antibody (anti-ubiquitin).

When SH-SY5Y cells expressing NLS1-deficient mutants that had been removed of nuclear localization signal were treated with MG132, and stained with a commercially available TDP-43 antibody (anti-TARDBP), cytoplasmic inclusions were not observed as can be appreciated from FIG. 5 (ΔNLS1). Therefore, the cells were next stained with phosphorylated TDP-43 antibody (anti-pS409/410) and observed with a confocal laser microscope. As a result, although cytoplasmic inclusions were not found with anti-TARDBP even after MG132 treatment (FIG. 5: ΔNLS1), anti-pS409/410-positive cytoplasmic inclusions were observed by anti-pS409/410 staining (FIG. 7: right panels). Similar to the intranuclear inclusions in FIG. 6, these cytoplasmic inclusions were also, although very weak, anti-ubiquitin positive. The diameter of the cytoplasmic inclusions was about 10 μm. Meanwhile, calpain inhibitor zLL was used for treatment in a similar manner, but no intracellular inclusion was observed and exactly the same result as the non treatment case was obtained (data not shown).

Figure 8:
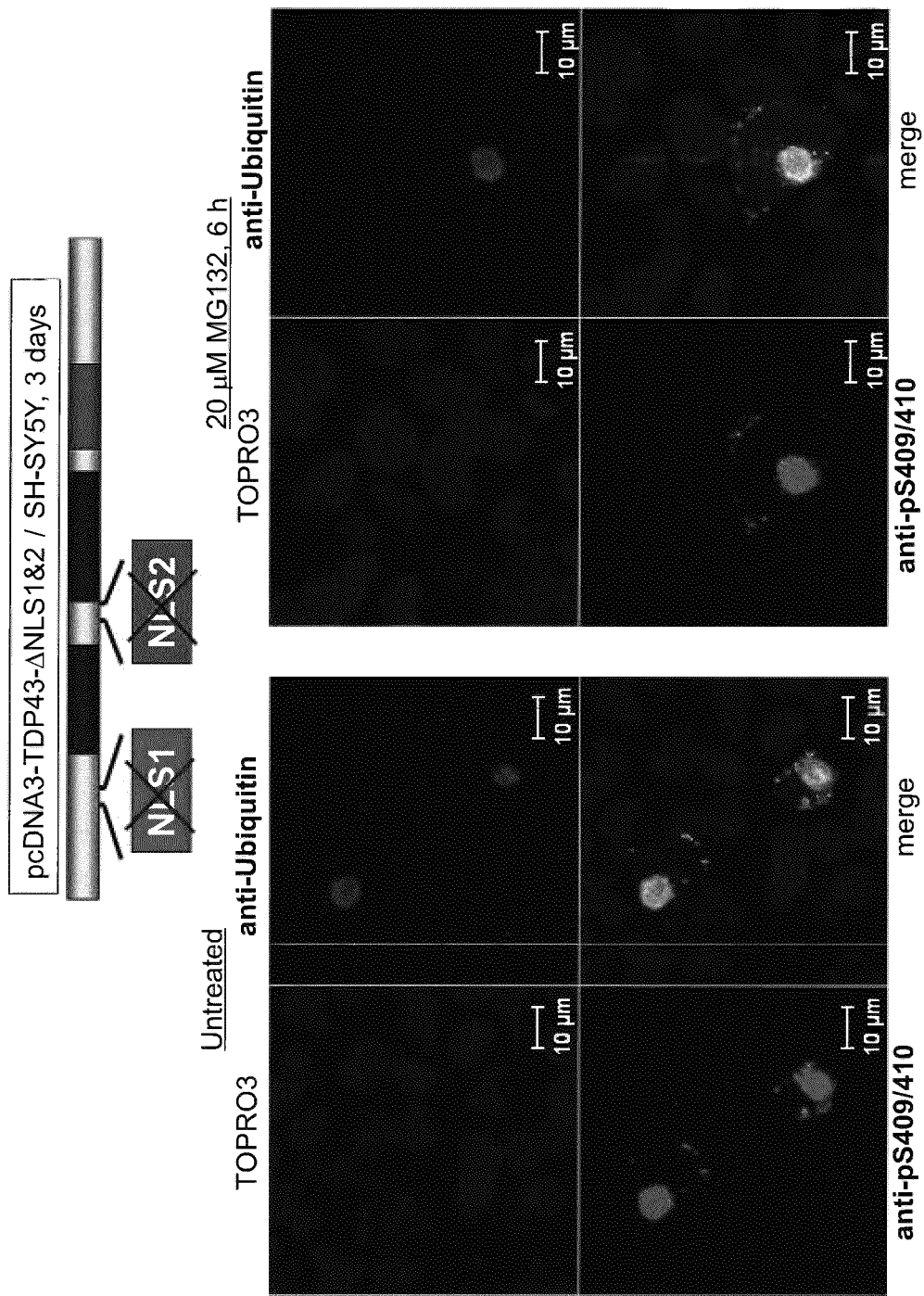
FIG. 8 shows the effects of the presence and absence of a treatment with a proteasome inhibitor (MG132) on ΔNLS1&2-expressing cells. The pictures are stained images obtained with anti-phosphorylated TDP-43 antibody (anti-pS409/410) and anti-ubiquitin antibody (anti-ubiquitin).

Furthermore, SH-SY5Y cells expressing a mutant deficient in both NLS1 and NLS2 sequences (ΔNLS1&2) was immunostained with anti-pS409/410 and anti-ubiquitin for observation with a confocal laser microscope. As a result, as shown in FIG. 8, anti-pS409/410- and anti-ubiquitin antibody-positive cytoplasmic inclusions were found in the cytoplasm of ΔNLS1&2-expressing cells without MG132 treatment, in other words, by plasmid expression only. The diameter of these cytoplasmic inclusions was about 10 μm.

Expression of GFP-Fused Protein

Figure 9:
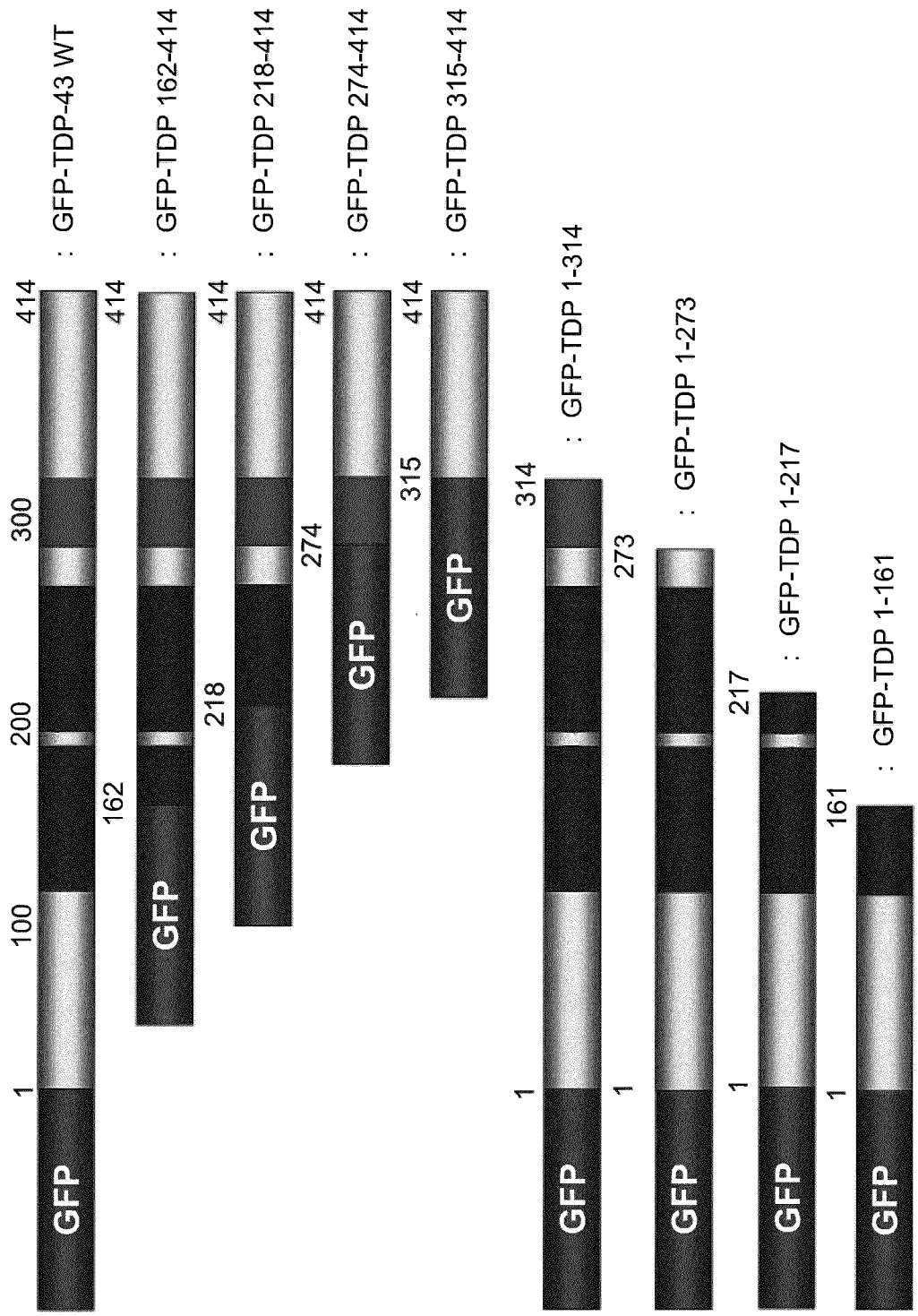
FIG. 9 is a schematic view of GFP-fused wild-type TDP-43 and various GFP-fused TDP-43 fragments.
Figure 10:
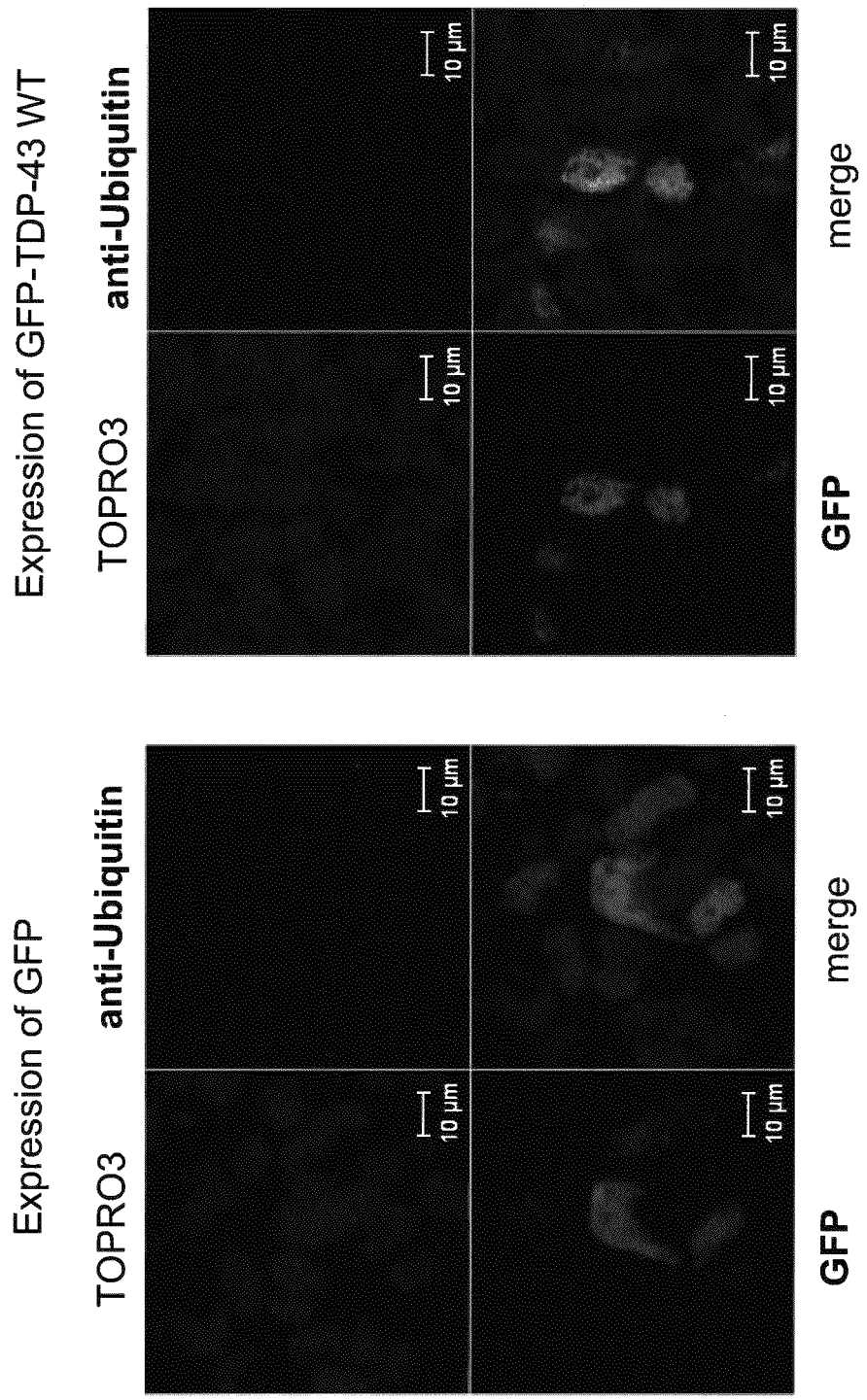
FIG. 10 shows the results from observation of GFP-expressing cells and GFP-TDP-43 WT-expressing cells with a confocal laser microscope. The pictures are stained images obtained with GFP fluorescence and anti-ubiquitin.
Figure 11:
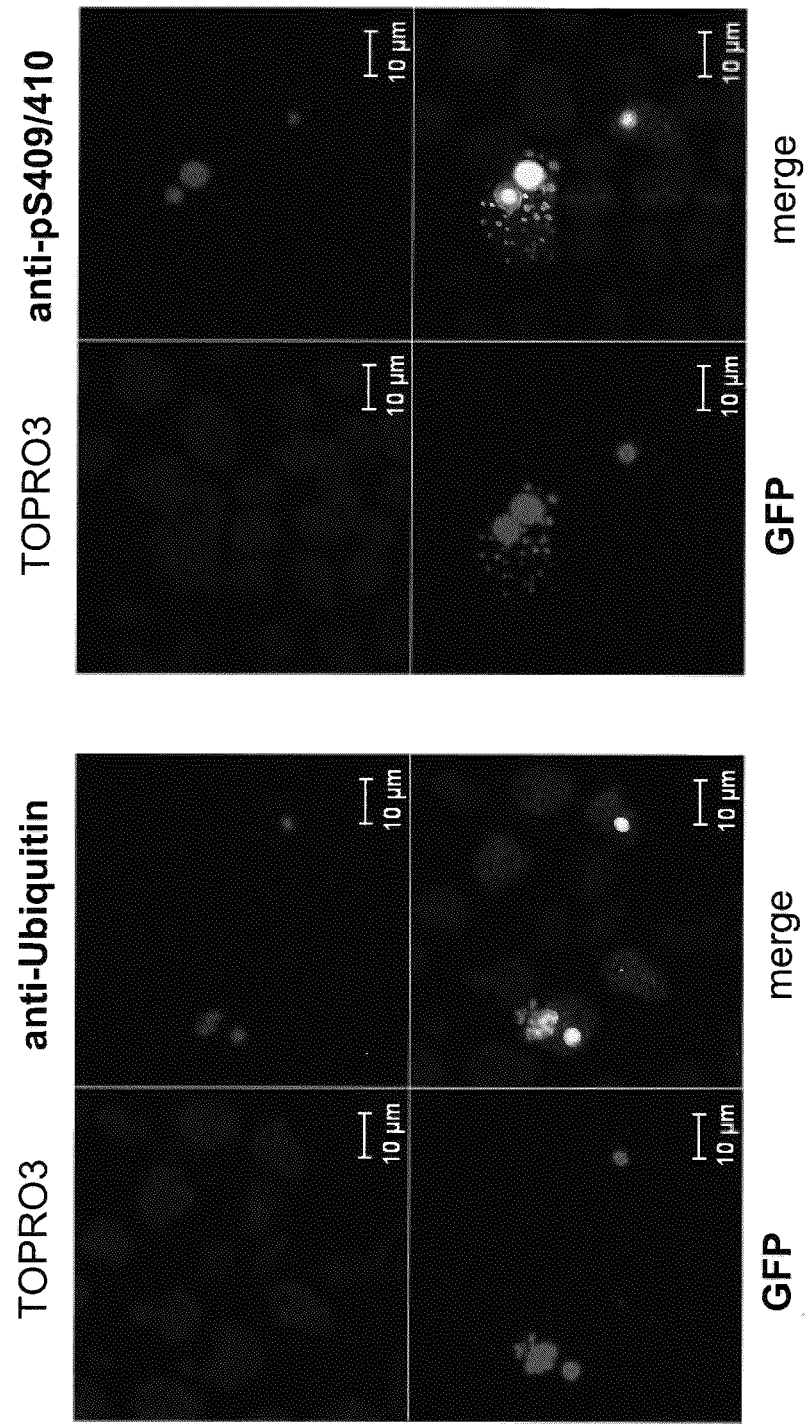
FIG. 11 shows the results from observation of GFP-TDP 162-414-expressing cells with a confocal laser microscope. The pictures are stained images obtained with GFP fluorescence and anti-pS409/410 or anti-ubiquitin.

When the present inventors performed immunoblotting with a commercially available polyclonal antibody (anti-TARDBP) on a surfactant-insoluble fraction prepared from FTLD patient's brain, a band was found near 20-35 kDa, which cannot be seen at all in the same fraction prepared from normal control brain (Arai T et al., Res. Commun., 2006, vol. 351(3), p. 602-611 (ibid.); Neumann M et al., Science, 2006, vol. 314(5796), p. 130-133 (ibid.)). This indicates that not only full-length TDP-43 but also a partial fragment of TDP-43 is also highly insoluble and accumulated in the patient's brain. Based on this fact, expression plasmids for various TDP-43 fragments were prepared and transfected into SH-SY5Y cells to express these fragments. First, according to a conventional process, a C-terminal fragment of residues 162-414 of TDP-43 was introduced into a pcDNA3 (+) vector (pcDNA3-TDP ΔN161), and transfected into the cell with FuGENE6. After incubation at 37° C. for 2 days, the cells were collected and subjected to immunoblotting analysis with anti-TARDBP antibody, but no expression was found at all (data not shown). Therefore, as the next step, when a fusion protein having a GFP tag fused to the N-terminal of a fragment of residues 162-414 of TDP-43 (GFP-TDP 162-414) was expressed in the cell, expression was observed (FIG. 11). Accordingly, plasmids coding for proteins having wild-type TDP-43 or any of the various TDP-43 fragments fused to the C-terminal of GFP were prepared (FIG. 9), which were expressed in SH-SY5Y cells and stained with anti-pS409/410 or anti-ubiquitin antibody for observation with a confocal laser microscope.

Figure 12:
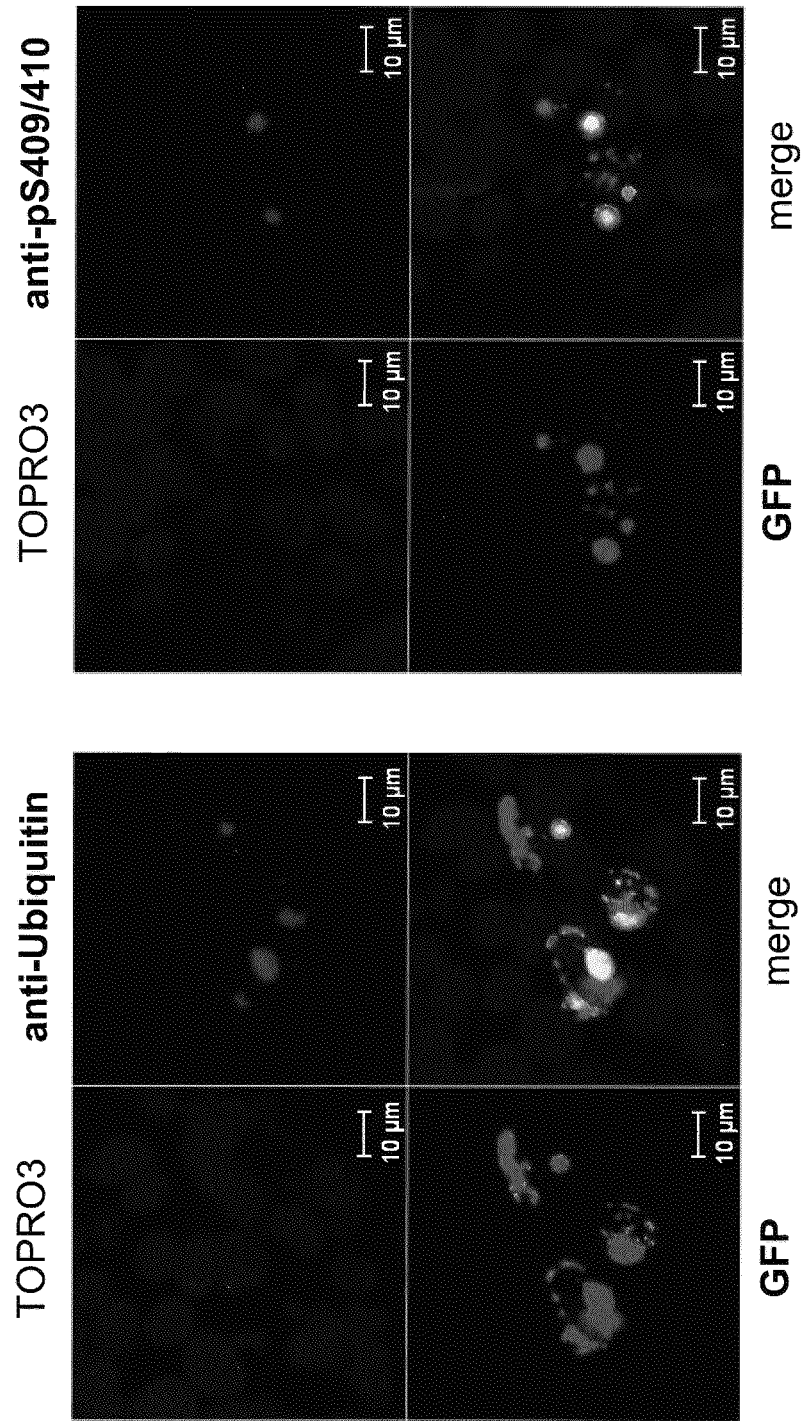
FIG. 12 shows the results from observation of GFP-TDP 218-414-expressing cells with a confocal laser microscope. The pictures are stained images obtained with GFP fluorescence and anti-pS409/410 or anti-ubiquitin.
Figure 13:
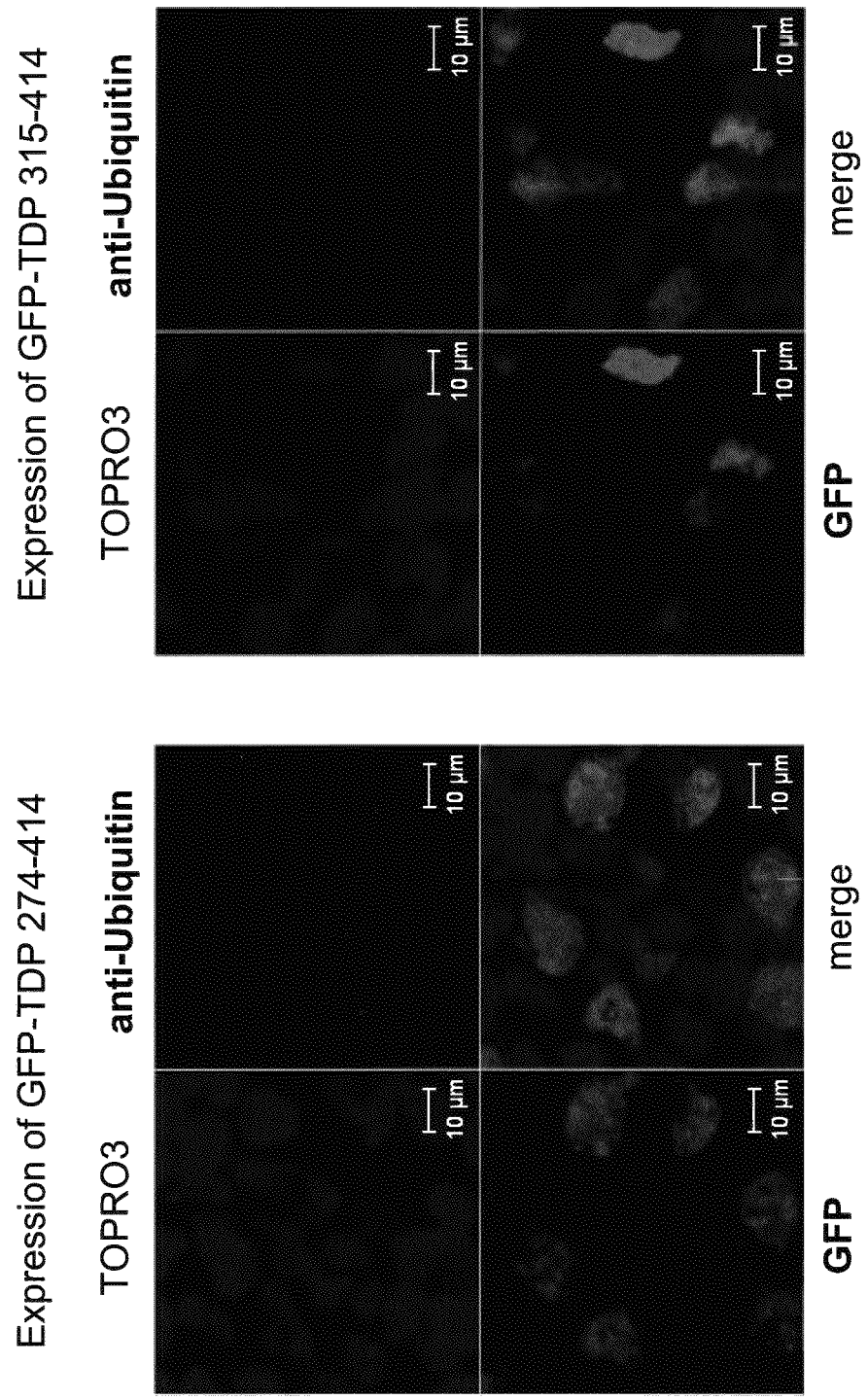
FIG. 13 shows the results from observation of GFP-TDP 274-414- and GFP-TDP 315-414-expressing cells with a confocal laser microscope. The pictures are stained images obtained with GFP fluorescence and anti-ubiquitin.

The results are shown in FIGS. 10-15. First, when only GFP was expressed (FIG. 10: left panels), typical GFP expression patterns were confirmed in the nucleus and cytoplasm. Next, when GFP-TDP WT was expressed (FIG. 10: right panels), the expression was observed only in the nucleus. Accordingly, there was no change in the expression pattern of GFP-fused TDP-43 due to man-caused influence by GFP tag binding. When GFP-TDP 162-414 that had been removed of the 161 residues at the N-terminal of TDP-43 was expressed (FIG. 11), intracellular inclusions positive to anti-pS409/410 and anti-ubiquitin antibodies emerged. These inclusions were also found when GFP-TDP 218-414 was expressed (FIG. 12). However, the intracellular inclusion was not observed at all in cells expressing GFP-TDP 274-414 or 315-414 that had been removed of the N-terminal residues (FIG. 13). Therefore, when GFP-TDP 162-414 and GFP-TDP 218-414 mutants were expressed in the cell, abnormal structures typical in patient's brain and similar to intracellular inclusions consisting of phosphorylated and ubiquitinated TDP were found to emerge.

Figure 14:
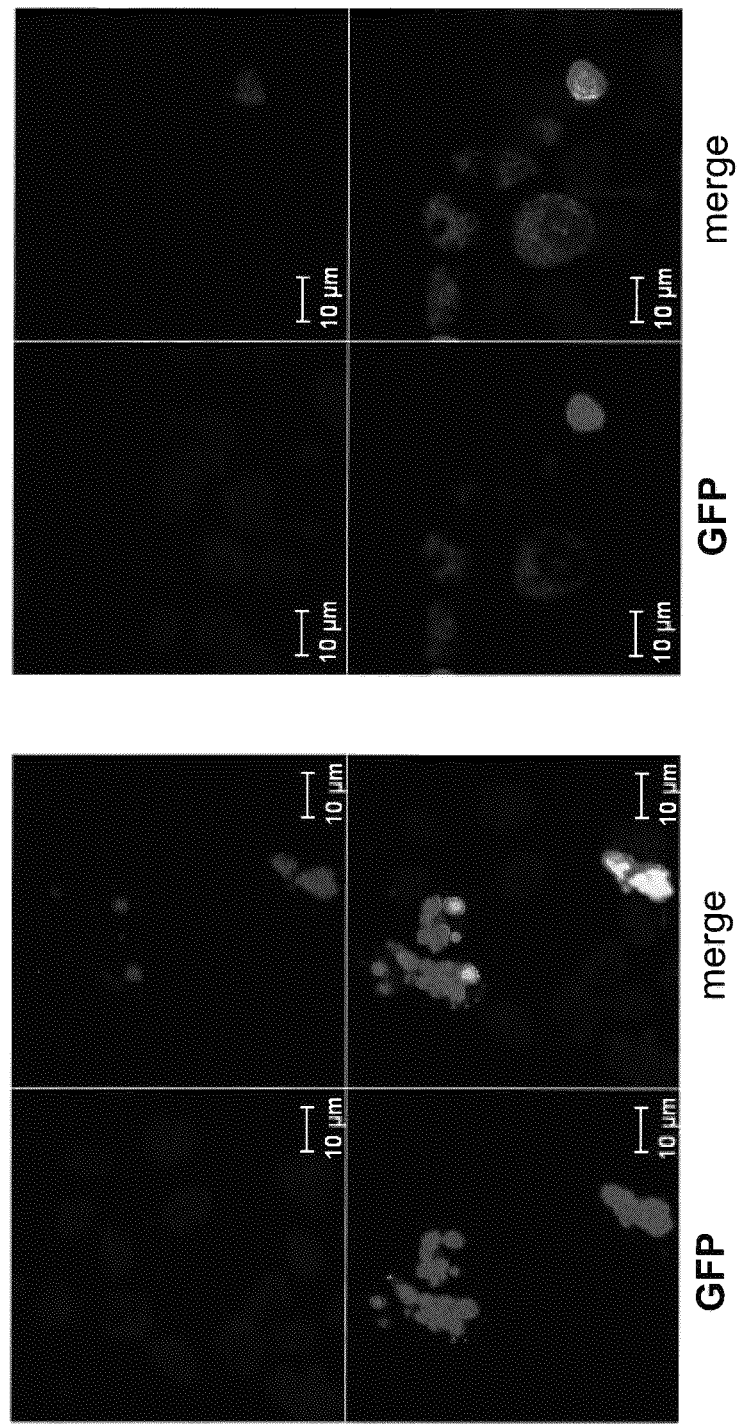
FIG. 14 shows the results from observation of GFP-TDP 1-161- and GFP-TDP 1-217-expressing cells with a confocal laser microscope. The pictures are stained images obtained with GFP fluorescence and anti-ubiquitin.
Figure 15:
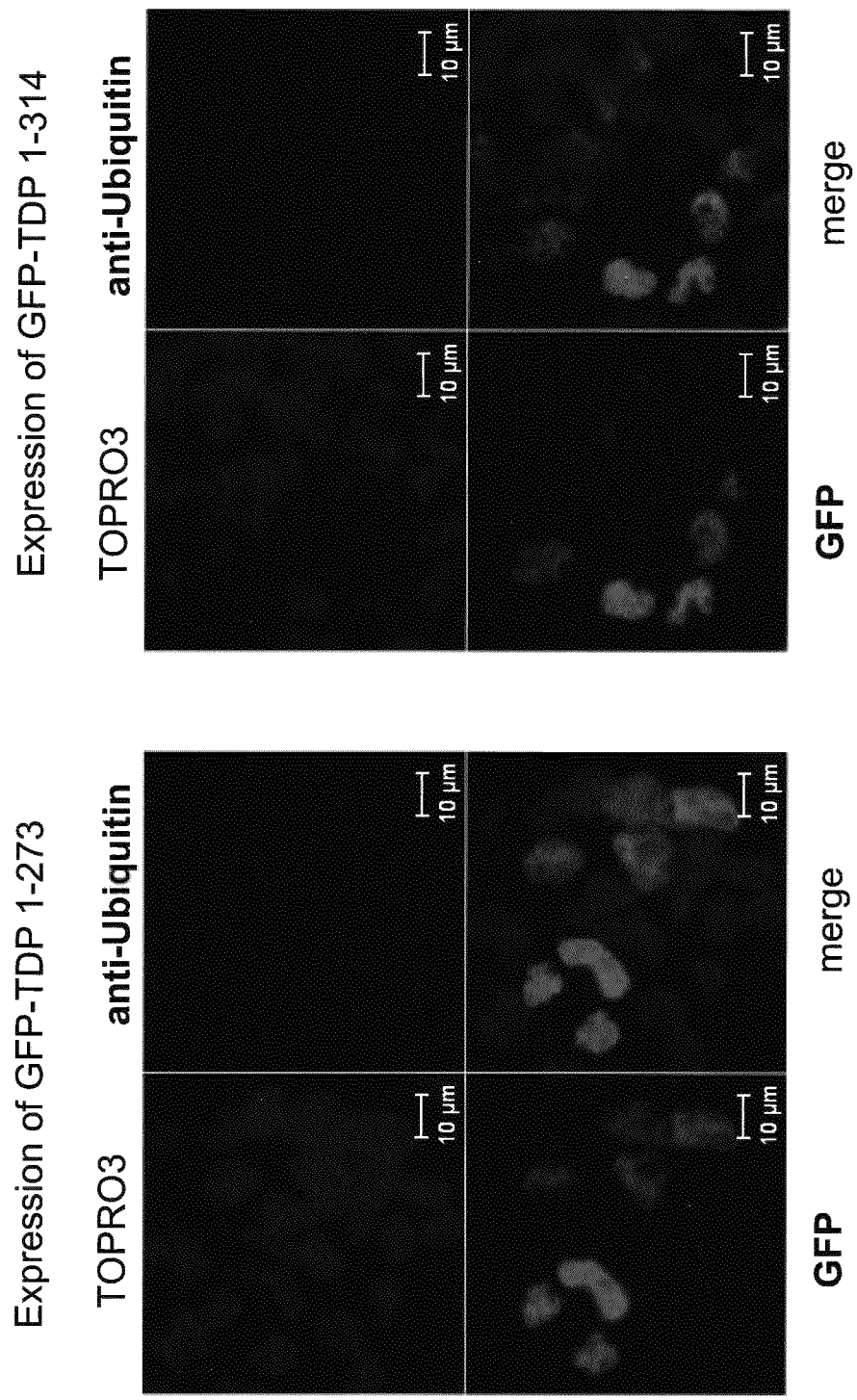
FIG. 15 shows the results from observation of GFP-TDP 1-273- and GFP-TDP 1-314-expressing cells with a confocal laser microscope. The pictures are stained images obtained with GFP fluorescence and anti-ubiquitin.

Similarly, mutants obtained by removing the C-terminal residues were prepared and transiently expressed in the cells. As a result, anti-pS409/410 and anti-ubiquitin-positive intracellular inclusions were significantly observed only when GFP-TDP 1-161 obtained by removing residues following residue 162 was expressed. Intracellular inclusions were not particularly observed when other N-terminal fragments were expressed (FIGS. 14 and 15). For the analysis of the cases of mutants obtained by removing the C-terminal residues, anti-phosphorylated TDP-43 antibody (anti-pS409/410) was not used since there was no phosphorylated site (Ser at positions 409 and 410) in these mutants.

From the above results, the present inventors succeeded in reproducing abnormal intracellular inclusions typically observed in patient's brain in the cultured cell by expressing various TDP-43 mutants or GFP-fused TDP-43 proteins in the cell, or in some cases, by combining with proteasome inhibition treatment.

CFTR Exon 9 Skipping Assay

In order to examine whether the TDP-43 mutants or the GFP-fused proteins in which the above-described intracellular inclusions had emerged were functionally different from wild-type TDP-43, CFTR exon 9 skipping assay was performed with TDP-43.

As a function of TDP-43, an activity of skipping CFTR exon 9 has been reported (Buratti E et al., EMBO J., 2001 (ibid.)). Specifically, a disease called congenital absence of the vas deferens, i.e., one type of cystic fibrosis, is known to occur by functional abnormality of immature CFTR due to the lack of CFTR exon 9 (Buratti E et al., EMBO J., 2001 (ibid.)). Involvement of TDP-43 has been reported in this lack of exon 9, where TDP-43 binds to a repeat sequence of certain bases (TG and T) present in an intron upstream of CFTR exon 9, which results in exon 9 skipping. The present inventors focused on such an activity of TDP-43 to skip CFTR exon 9 and compared the wild-type and various mutants using this activity as an indicator.

Figure 16:
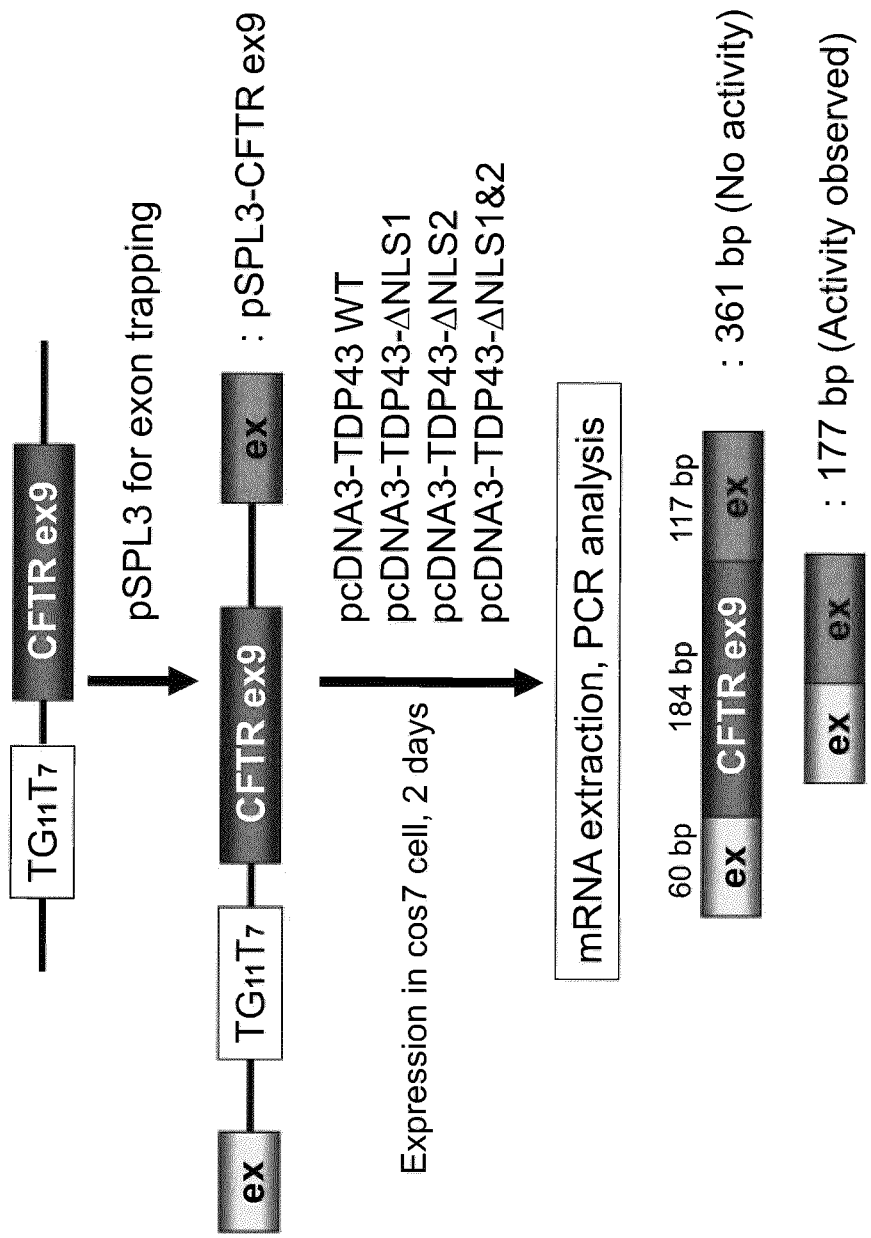
FIG. 16 is a schematic view showing a method of CFTR exon 9 skipping assay.

A brief scheme is shown in FIG. 16. As described above, a region including the intron upstream of CFTR exon 9 was cloned from a normal healthy person and inserted into a pSPL3 vector to prepare a pSPL3-CFTR ex9 vector. This was expressed in cos7 cell with the various TDP-43 mutants or GFP-fused body, and mRNA was prepared from the expressing cell for PCR analysis.

Figure 17:
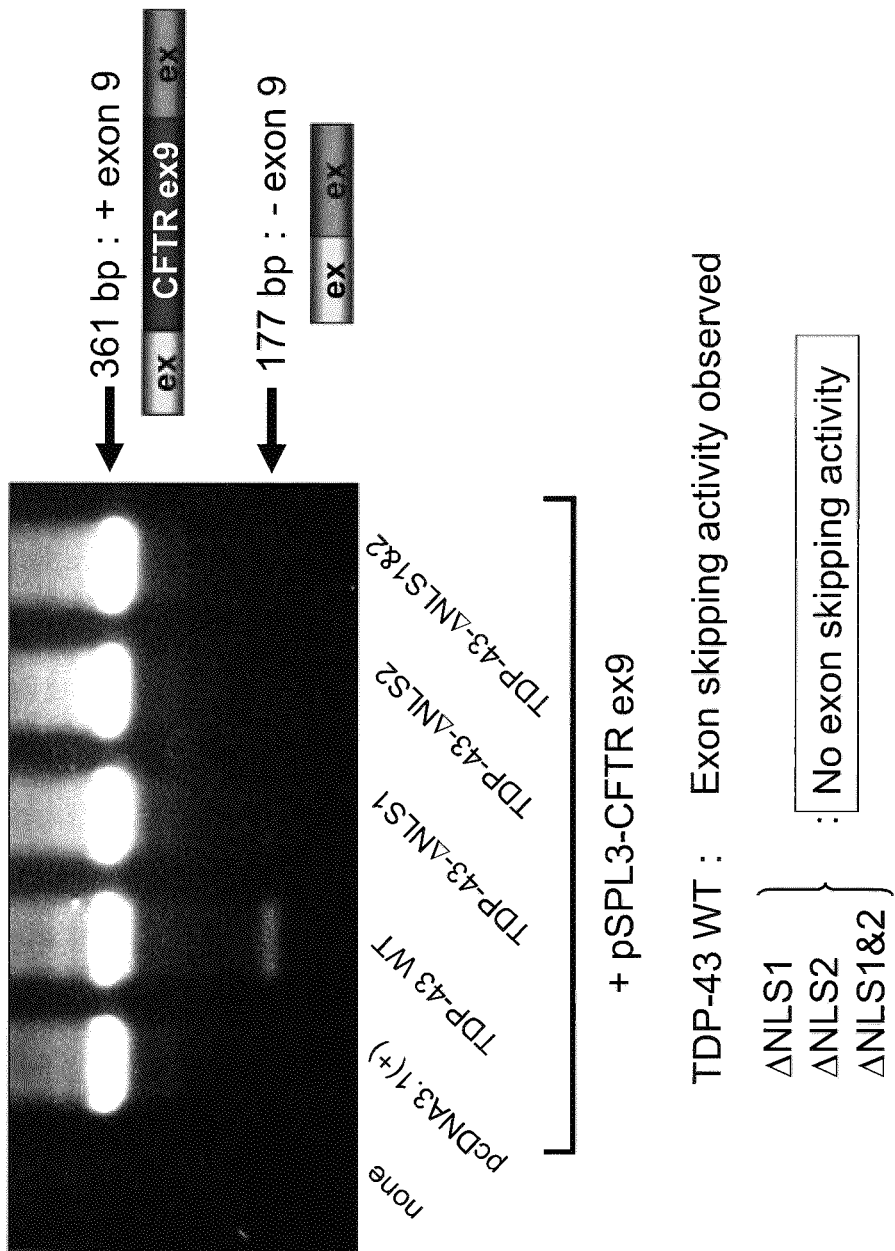
FIG. 17 shows the results from CFTR exon 9 skipping assay.
Figure 18:
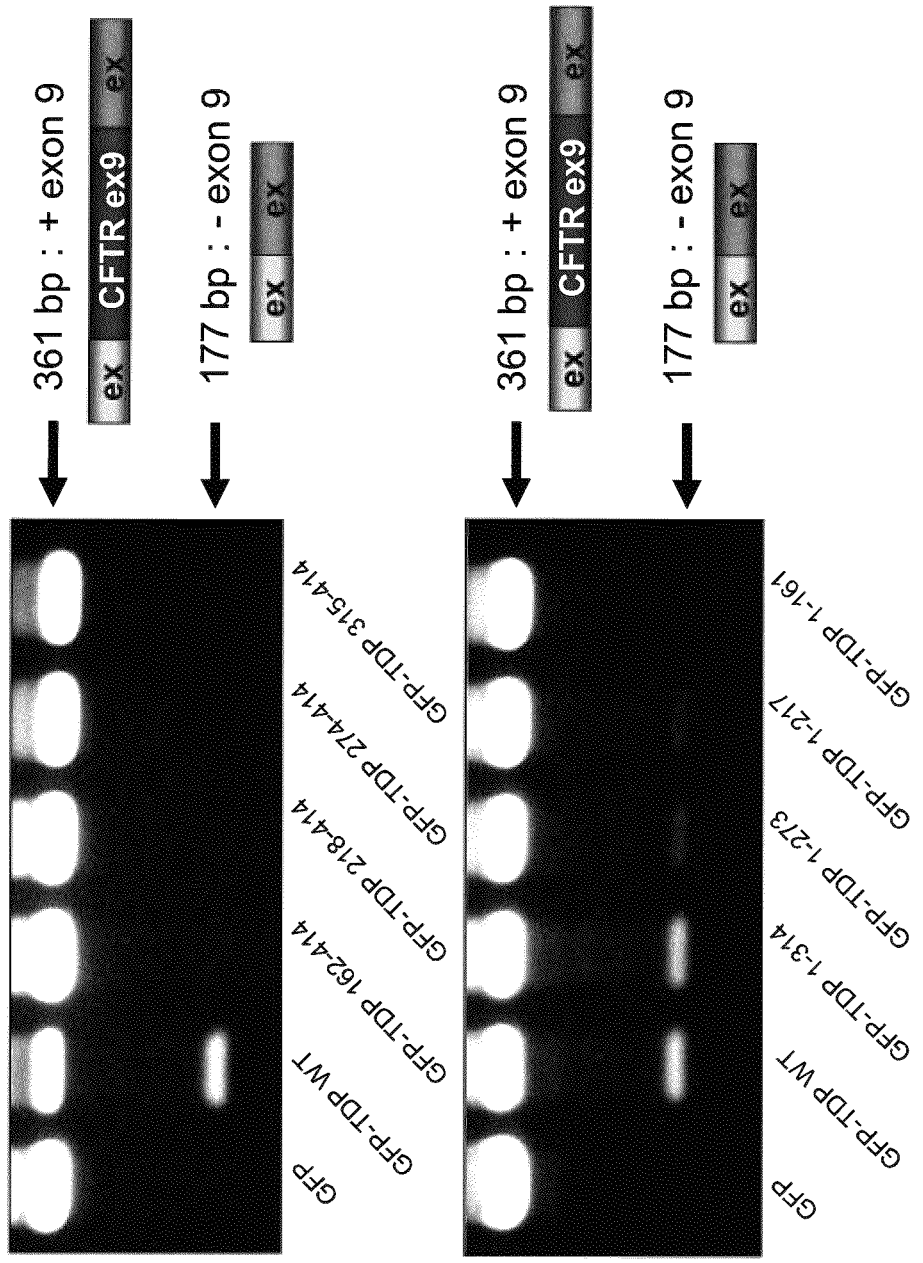
FIG. 18 shows the results from CFTR exon 9 skipping assay.

A band was detected at 117 bp when exon 9 was skipped in the expressing cell whereas a band was detected at 361 bp when exon 9 was not skipped (FIG. 16). Samples of the expressing cells were subjected to PCR analysis and agarose gel electrophoresis. As a result, unlike expression of wild-type TDP-43, exon 9 skipping band was not detected at all when a NLS1-deficient mutant, a NLS2-deficient mutant and a NLS1&2-deficient mutant were expressed (FIG. 17). Specifically, CFTR exon 9 skipping activity was found to be absent in the three types of mutants observed with formation of intracellular inclusions. Similarly, when a GFP-fused protein and pSPL3-CFTR ex9 were coexpressed, CFTR exon 9 skipping activity was not observed in the three types of mutants observed with intracellular inclusions, i.e., GFP-TDP 162-414, GFP-TDP 218-414 and GFP-TDP 1-161 (FIG. 18). Since CFTR exon 9 skipping activity was observed upon expression of a GFP-fused body of wild-type TDP-43 (GFP-TDP-43 WT) (FIG. 18), these results were not caused by a man-caused influence, i.e., GFP fusion.

According to the above results, among the deficient mutants of TDP-43 and GFP-fused body, mutants that formed intracellular inclusions had no CFTR exon 9 skipping activity, indicating association between the formation of intracellular inclusions by TDP-43 and deterioration in the function thereof. This result makes great contributions to elucidation of the mechanism of formation of intracellular inclusions by TDP-43, and considered to lead to FTLD or ALS onset mechanism and development of a therapeutic drug thereof.

Figure 23:
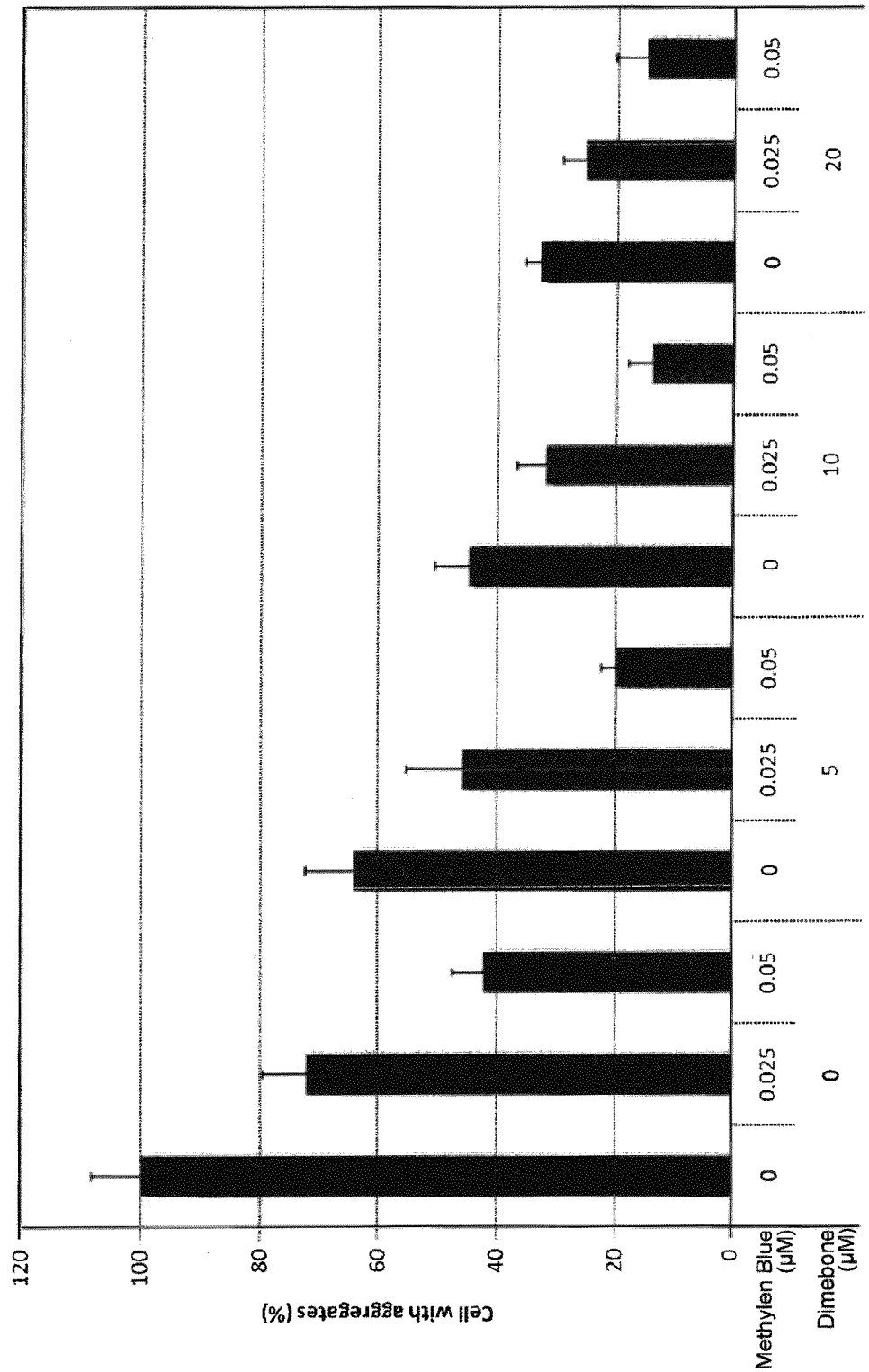
FIG. 23 shows the results from quantitating the percentage of the cells forming intracellular TDP-43 inclusions with respect to an effect of suppressing TDP-43 delta NLS1&2 to form an intracellular TDP-43 inclusion using low-molecular compounds (methylene blue and dimebon). The horizontal and vertical axes in the graph represent the concentrations of methylene blue and dimebon and the percentage of cells forming intracellular TDP-43 inclusions, respectively.
Figure 24:
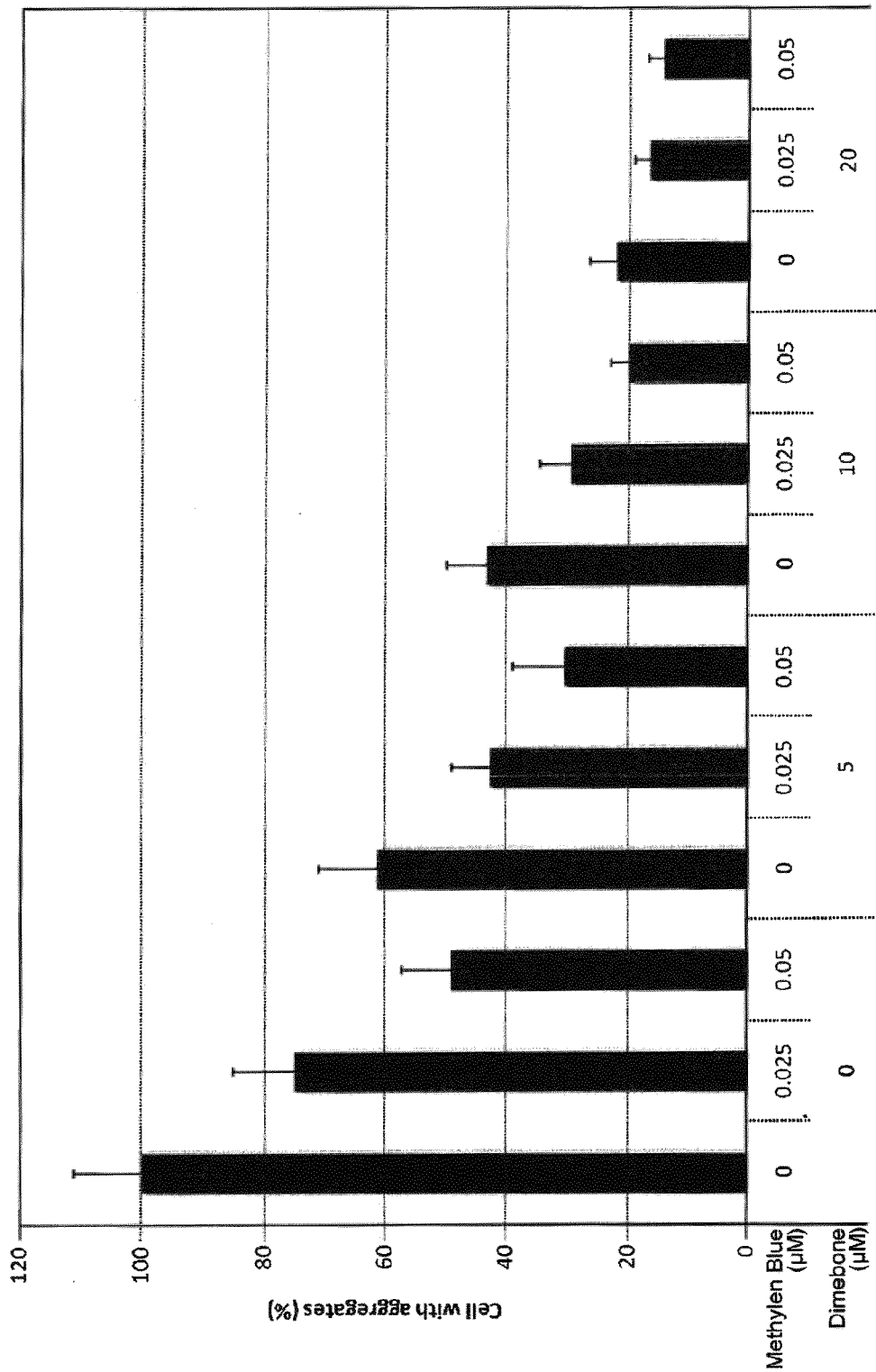
FIG. 24 shows the results from quantitating the percentage of the cells forming intracellular TDP-43 inclusions with respect to an effect of suppressing GFP-TDP 162-414 to form an intracellular TDP-43 inclusion using low-molecular compounds (methylene blue and dimebon). The horizontal and vertical axes in the graph represent the concentrations of methylene blue and dimebon and the percentage of cells forming intracellular TDP-43 inclusions, respectively.

Suppression of Formation of Intracellular Inclusions by TDP-43 with Low-Molecular Compounds pEGFP-TDP 162-414 (GFP-TDP 162-414) and pcDNA3-TDP delta NLS1&2 (TDP delta NLS1&2) that were found to form intracellular inclusions were used to search for a low-molecular compound that suppresses formation of the inclusions. As a result, inhibition effect of methylene blue was confirmed at a low concentration of 0.05 μM in both deficient mutants, which enhanced concentration-dependently (FIGS. 19 and 20). Meanwhile, inhibition effect of dimebon was also confirmed at 20 μM, which enhanced concentration-dependently (FIGS. 21 and 22). Furthermore, when methylene blue and dimebon were used in combination and added at the same time, the effect was further enhanced at low concentrations of 0.025 μM (methylene blue) and 5-10 μM (dimebon), confirming an inhibition effect of about 70-85% compared to the untreated case (FIGS. 23 and 24). Thus, methylene blue and dimebon were considered to be useful as an active element of a therapeutic drug for a neurodegenerative disease, in particular a neurodegenerative disease associated with formation of intracellular inclusions by TDP-43.

INDUSTRIAL APPLICABILITY

The present invention is capable of providing a transformed cell (a cell model) that forms an intracellular inclusion of TAR DNA-binding protein of 43 kDa (TDP-43) that is found in the brain of a patient suffering from a neurodegenerative disease such as FTLD or ALS. Moreover, the present invention is capable of providing a mutant TDP-43 protein or a TDP-43 protein fragment that becomes a primary component of such an intracellular TDP-43 inclusion.

An intracellular TDP-43 inclusion formed by the cell model provided by the present invention has very similar property to the inclusions found in the above-mentioned patient's brain, not only in terms of the size but also in that it is positive to anti-phosphorylated TDP-43 antibody and anti-ubiquitin antibody. A transformed cell of the present invention is very useful in that it can be used for screening a compound, gene or the like that suppresses intranuclear or intracytoplasmic accumulation of TDP-43, and for developing a novel therapeutic drug or the like for a neurodegenerative disease such as FTLD or ALS. In fact, it is extremely practical since compounds (methylene blue and dimebon) that suppress intracytoplasmic accumulation of TDP-43 (formation of intracellular inclusions by TDP-43) were found by the present inventors by the use of the transformed cell.

SEQUENCE LISTING: FREE TEXT

SEQ ID NO:3: Synthetic DNA
SEQ ID NO:4: Synthetic DNA
SEQ ID NO:5: Synthetic DNA
SEQ ID NO:6: Synthetic DNA
SEQ ID NO:7: Synthetic DNA
SEQ ID NO:8: Synthetic DNA
SEQ ID NO:9: Synthetic DNA
SEQ ID NO:10: Synthetic DNA
SEQ ID NO:11: Synthetic DNA
SEQ ID NO:12: Synthetic DNA
SEQ ID NO:13: Synthetic DNA
SEQ ID NO:14: Synthetic DNA
SEQ ID NO:15: Synthetic DNA
SEQ ID NO:17: Synthetic DNA
SEQ ID NO:18: Synthetic DNA
SEQ ID NO:19: Phosphorylated synthetic peptide
SEQ ID NO:19: Ser represents a phosphorylated serine residue (locations: 6, 7)
SEQ ID NO:20: Synthetic DNA

The invention claimed is:

1. A transformed cell having a mutant TDP-43 gene operably linked to a promoter introduced therein, wherein the mutant TDP-43 gene encodes any one of the following proteins (b) and (d):

(b) a protein having an amino acid sequence consisting of amino acids 218-414 of the amino acid sequence of wild-type TDP-43; and (d) a protein that has an amino acid sequence having one to ten amino acids deleted from, substituted in or added to the amino acid sequence (b) and that has an activity of forming an intracellular inclusion.

2. The cell according to claim 1, wherein the mutant TDP-43 has no CFTR exon 9 skipping activity.

3. The cell according to claim 1, which is a transformed mammal cell.

4. The cell according to claim 3, wherein the mammal cell is a central nervous system cell, a peripheral nervous system cell or a neuroblast.

5. A method for screening a therapeutic drug for a neurodegenerative disease, comprising the steps of: causing the cell according to claim 1 to make contact with a candidate substance to measure a cellular activity of the cell; and using the obtained measurement result as an indicator.

6. The method according to claim 5, wherein the cellular activity is at least one selected from the group consisting of proliferation capacity, viability, and the rate, number and size of an intracellular mutant TDP-43 inclusion formed.

7. The method according to claim 5 or 6, wherein the neurodegenerative disease is frontotemporal lobar degeneration or amyotrophic lateral sclerosis.

8. The method according to claim 5, wherein the neurodegenerative disease is associated with formation of an intracellular TDP-43 inclusion.

9. A method for screening an agent for suppressing formation of an intracellular mutant TDP-43 inclusion, comprising the steps of: causing the cell according to claim 1 to make contact with a candidate substance to measure a cellular activity of the cell; and using the obtained measurement result as an indicator.

10. The method according to claim 9, wherein the cellular activity is at least one selected from the group consisting of proliferation capacity, viability, and the rate, number and size of an intracellular mutant TDP-43 inclusion formed.

11. A method for assessing a side-effect of a therapeutic drug for a neurodegenerative disease, comprising the steps of: causing the cell according to claim 1 to make contact with the therapeutic drug for the neurodegenerative disease to measure a cellular activity of the cell: and using the obtained measurement result as an indicator.

12. The method according to claim 11, wherein the cellular activity is at least one selected from the group consisting of neurite elongation capability, proliferation capacity and viability.

13. The method according to claim 11 or 12, wherein the neurodegenerative disease is frontotemporal lobar degeneration or amyotrophic lateral sclerosis.

14. The method according to claim 11, wherein the neurodegenerative disease is associated with formation of an intracellular TDP-43 inclusion.

\* \* \* \* \*

SEQUENCE LISTING

```
<160> NUMBER OF SEQ ID NOS: 20

<210> SEQ ID NO 1
<211> LENGTH: 4236
<212> TYPE: DNA
<213> ORGANISM: Homo sapiens
<220> FEATURE:
<221> NAME/KEY: CDS
<222> LOCATION: (135)..(1379)

<400> SEQUENCE: 1
ggtgggcggg gggaggaggc ggccctagcg ccattttgtg ggagcgaagc ggtggctggg      60
ctgcgcttgg gtccgtcgct gcttcggtgt ccctgtcggg cttcccagca gcggcctagc     120
gggaaaagta aaag atg tct gaa tat att cgg gta acc gaa gat gag aac       170
             Met Ser Glu Tyr Ile Arg Val Thr Glu Asp Glu Asn
               1               5                  10 gat gag ccc att gaa ata cca tcg gaa gac gat ggg acg gtg ctg ctc       218
Asp Glu Pro Ile Glu Ile Pro Ser Glu Asp Asp Gly Thr Val Leu Leu
         15                  20                  25 tcc acg gtt aca gcc cag ttt cca ggg gcg tgt ggg ctt cgc tac agg       266
Ser Thr Val Thr Ala Gln Phe Pro Gly Ala Cys Gly Leu Arg Tyr Arg
     30                  35                  40 aat cca gtg tct cag tgt atg aga ggt gtc cgg ctg gta gaa gga att       314
Asn Pro Val Ser Gln Cys Met Arg Gly Val Arg Leu Val Glu Gly Ile
 45                  50                  55                  60 ctg cat gcc cca gat gct ggc tgg gga aat ctg gtg tat gtt gtc aac       362
Leu His Ala Pro Asp Ala Gly Trp Gly Asn Leu Val Tyr Val Val Asn
```

```
                         65                  70                  75
tat cca aaa gat aac aaa aga aaa atg gat gag aca gat gct tca tca       410
Tyr Pro Lys Asp Asn Lys Arg Lys Met Asp Glu Thr Asp Ala Ser Ser
         80                  85                  90 gca gtg aaa gtg aaa aga gca gtc cag aaa aca tcc gat tta ata gtg       458
Ala Val Lys Val Lys Arg Ala Val Gln Lys Thr Ser Asp Leu Ile Val
         95                 100                 105 ttg ggt ctc cca tgg aaa aca acc gaa cag gac ctg aaa gag tat ttt       506
Leu Gly Leu Pro Trp Lys Thr Thr Glu Gln Asp Leu Lys Glu Tyr Phe
    110                 115                 120 agt acc ttt gga gaa gtt ctt atg gtg cag gtc aag aaa gat ctt aag       554
Ser Thr Phe Gly Glu Val Leu Met Val Gln Val Lys Lys Asp Leu Lys
125                 130                 135                 140 act ggt cat tca aag ggg ttt ggc ttt gtt cgt ttt acg gaa tat gaa       602
Thr Gly His Ser Lys Gly Phe Gly Phe Val Arg Phe Thr Glu Tyr Glu
        145                 150                 155 aca caa gtg aaa gta atg tca cag cga cat atg ata gat gga cga tgg       650
Thr Gln Val Lys Val Met Ser Gln Arg His Met Ile Asp Gly Arg Trp
        160                 165                 170 tgt gac tgc aaa ctt cct aat tct aag caa agc caa gat gag cct ttg       698
Cys Asp Cys Lys Leu Pro Asn Ser Lys Gln Ser Gln Asp Glu Pro Leu
        175                 180                 185 aga agc aga aaa gtg ttt gtg ggg cgc tgt aca gag gac atg act gag       746
Arg Ser Arg Lys Val Phe Val Gly Arg Cys Thr Glu Asp Met Thr Glu
    190                 195                 200 gat gag ctg cgg gag ttc ttc tct cag tac ggg gat gtg atg gat gtc       794
Asp Glu Leu Arg Glu Phe Phe Ser Gln Tyr Gly Asp Val Met Asp Val
205                 210                 215                 220 ttc atc ccc aag cca ttc agg gcc ttt gcc ttt gtt aca ttt gca gat       842
Phe Ile Pro Lys Pro Phe Arg Ala Phe Ala Phe Val Thr Phe Ala Asp
                225                 230                 235 gat cag att gcg cag tct ctt tgt gga gag gac ttg atc att aaa gga       890
Asp Gln Ile Ala Gln Ser Leu Cys Gly Glu Asp Leu Ile Ile Lys Gly
        240                 245                 250 atc agc gtt cat ata tcc aat gcc gaa cct aag cac aat agc aat aga       938
Ile Ser Val His Ile Ser Asn Ala Glu Pro Lys His Asn Ser Asn Arg
        255                 260                 265 cag tta gaa aga agt gga aga ttt ggt ggt aat cca ggt ggc ttt ggg       986
Gln Leu Glu Arg Ser Gly Arg Phe Gly Gly Asn Pro Gly Gly Phe Gly
    270                 275                 280 aat cag ggt gga ttt ggt aat agc aga ggg ggt gga gct ggt ttg gga      1034
Asn Gln Gly Gly Phe Gly Asn Ser Arg Gly Gly Gly Ala Gly Leu Gly
285                 290                 295                 300 aac aat caa ggt agt aat atg ggt ggt ggg atg aac ttt ggt gcg ttc      1082
Asn Asn Gln Gly Ser Asn Met Gly Gly Gly Met Asn Phe Gly Ala Phe
                305                 310                 315 agc att aat cca gcc atg atg gct gcc gcc cag gca gca cta cag agc      1130
Ser Ile Asn Pro Ala Met Met Ala Ala Ala Gln Ala Ala Leu Gln Ser
        320                 325                 330 agt tgg ggt atg atg ggc atg tta gcc agc cag cag aac cag tca ggc      1178
Ser Trp Gly Met Met Gly Met Leu Ala Ser Gln Gln Asn Gln Ser Gly
        335                 340                 345 cca tcg ggt aat aac caa aac caa ggc aac atg cag agg gag cca aac      1226
Pro Ser Gly Asn Asn Gln Asn Gln Gly Asn Met Gln Arg Glu Pro Asn
    350                 355                 360 cag gcc ttc ggt tct gga aat aac tct tat agt ggc tct aat tct ggt      1274
Gln Ala Phe Gly Ser Gly Asn Asn Ser Tyr Ser Gly Ser Asn Ser Gly
365                 370                 375                 380 gca gca att ggt tgg gga tca gca tcc aat gca ggg tcg ggc agt ggt      1322
```

| | | |
|---|---|---|
| Ala Ala Ile Gly Trp Gly Ser Ala Ser Asn Ala Gly Ser Gly Ser Gly<br>              385                    390                    395 | | |
| ttt aat gga ggc ttt ggc tca agc atg gat tct aag tct tct ggc tgg<br>Phe Asn Gly Gly Phe Gly Ser Ser Met Asp Ser Lys Ser Ser Gly Trp<br>              400                    405                    410 | 1370 | |
| gga atg tag acagtggggt tgtggttggt tggtatagaa tggtgggaat<br>Gly Met | 1419 | |
| tcaatttttt ctaaactcat ggtaagtata ttgtaaaata catatgtact aagaattttc | 1479 | |
| aaaattggtt tgttcagtgt ggagtatatt cagcagtatt tttgacattt ttctttagaa | 1539 | |
| aaaggaagag ctaaaggaat tttataagtt ttgttacatg aaaggttgaa atattgagtg | 1599 | |
| gttgaaagtg aactgctgtt tgcctgattg gtaaaccaac acactacaat tgatatcaaa | 1659 | |
| aggtttctcc tgtaatattt tatccctgga cttgtcaagt gaattctttg catgttcaaa | 1719 | |
| acggaaacca ttgattagaa ctacattctt taccccttgt tttaatttga accccaccat | 1779 | |
| atggattttt ttccttaaga aaatctcctt ttaggagatc atggtgtcac agtgtttggt | 1839 | |
| tcttttgttt tgtttttttaa cacttgtctc ccctcataca caaaagtaca atatgaagcc | 1899 | |
| ttcatttaat ctctgcagtt catctcattt caaatgttta tggaagaagc acttcattga | 1959 | |
| aagtagtgct gtaaatattc tgccatagga atactgtcta catgctttct cattcaagaa | 2019 | |
| ttcgtcatca cgcatcacag gccgcgtctt tgacggtggg tgtcccattt ttatccgcta | 2079 | |
| ctctttattt catggagtcg tatcaacgct atgaacgcaa ggctgtgata tggaaccaga | 2139 | |
| aggctgtctg aacttttgaa accttgtgtg ggattgatgg tggtgccgag catgaaagg | 2199 | |
| ctagtatgag cgagaaaagg agagagcgcg tgcagagact tggtggtgca taatggatat | 2259 | |
| ttttttaactt ggcgagatgt gtctctcaat cctgtggctt tggtgagaga gtgtgcagag | 2319 | |
| agcaatgata gcaaataatg tacgaatgtt ttttgcattc aaaggacatc cacatctgtt | 2379 | |
| ggaagacttt taagtgagtt tttgttctta gataacccac attagatgaa tgtgttaagt | 2439 | |
| gaaatgatac ttgtactccc cctacccctt tgtcaactgc tgtgaatgct gtatggtgtg | 2499 | |
| tgttctcttc tgttactgat atgtaagtgt ggcaatgtga actgaagctg atgggctgag | 2559 | |
| aacatggact gagcttgtgg tgtgctttgc aggaggactt gaagcagagt tcaccagtga | 2619 | |
| gctcaggtgt ctcaaagaag ggtggaagtt ctaatgtctg ttagctaccc ataagaatgc | 2679 | |
| tgtttgctgc agttctgtgt cctgtgcttg atgcttttt ataagagttg tcattgttgg | 2739 | |
| aaattcttaa ataaaactga tttaaataat atgtgtcttt gttttgcagc cctgaatgca | 2799 | |
| aagaattcat agcagttaat tccccttttt tgacccttt gagatggaac tttcataaag | 2859 | |
| tttcttggca gtagtttatt ttgcttcaaa taaacttatt tgaaaagttg tctcaagtca | 2919 | |
| aatggattca tcacctgtca tgcattgaca cctgataccc agacttaatt ggtatttgtt | 2979 | |
| cttgcattgg ccaaagtgaa aattttttt tttcttttga aatctagttt tgaataagtc | 3039 | |
| tgggtgaccg cacctaaaat ggtaagcagt accctccggc ttttttcttag tgcctctgtg | 3099 | |
| catttgggtg atgttctatt tacatggcct gtgtaaatct ccattgggaa gtcatgcctt | 3159 | |
| ctaaaaagat tcttatttgg gggagtgggc aaaatgttga ttattttcta atgctttgta | 3219 | |
| gcaaagcata tcaattgaaa agggaatatc agcaccttcc tagtttggga tttgaaaagt | 3279 | |
| ggaattaatt gcagtaggga taaagtagaa gaaaccacaa attatcttgt gcctgaaatc | 3339 | |
| cattaagagg cctgatagct ttaagaatta gggtggggtt tctgtctgga agtgttaagt | 3399 | |
| ggaatgggct ttgtcctcca ggaggtgggg gaatgtggta acattgaata cagttgaata | 3459 | |
| aaatcgctta caaaactcac actctcacaa tgcattgtta agtatgtaaa agcaataaca | 3519 | |

```
ttgattctct gttgtacttt tttgtaacta attctgtgag agttgagctc attttctagt      3579
tggaagaatg tgatatttgt tgtgttggta gtttacctaa tgcccttacc taattagatt      3639
atgataaata ggtttgtcat tttgcaagtt acataaacat ttatcaatga agtcatcctt      3699
tagacttgta atcgccacat tgtttcatta ttcagtttcc tctgtaaagg gatcttgagt     3759
tgttttaatt tttttttct gcatctgaat ctgcatgatt tccaaaccct gtaccatctg      3819
aattttgcat tttagcactt gcactattac tcagcagcag taacatggta acacttaaaa     3879
tggtactcgg ggacctccaa agactaaact gacaagcctt caaggagccc aggggtaagt     3939
taacttgtca acggcatggt ttaatcccct ctttacactt gtgtaaattt cagttactgg     3999
tcatagaagg ctttcaatgt tgagtggcct tttattaaca tgtttatggt actgcataga     4059
tacgggtatt tattttaccc taagaagatt ttgaagttta aaagtactta aactatttgg     4119
caaagatttg ttttttaaaaa tctatttggt caatctaaat gcattcattc taaaaaattt    4179
tttgaaccag ataaataaaa ttttttttg acaccacaaa aaaaaaaaaa aaaaaaa        4236
```

<210> SEQ ID NO 2
<211> LENGTH: 414
<212> TYPE: PRT
<213> ORGANISM: Homo sapiens

<400> SEQUENCE: 2

```
Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

Gln Cys Met Arg Gly Val Arg Leu Val Glu Gly Ile Leu His Ala Pro
    50                  55                  60

Asp Ala Gly Trp Gly Asn Leu Val Tyr Val Val Asn Tyr Pro Lys Asp
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
        115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg
        195                 200                 205

Glu Phe Phe Ser Gln Tyr Gly Asp Val Met Asp Val Phe Ile Pro Lys
    210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
```

```
                      245                 250                 255
Ile Ser Asn Ala Glu Pro Lys His Asn Ser Asn Arg Gln Leu Glu Arg
            260                 265                 270

Ser Gly Arg Phe Gly Gly Asn Pro Gly Gly Phe Gly Asn Gln Gly Gly
        275                 280                 285

Phe Gly Asn Ser Arg Gly Gly Gly Ala Gly Leu Gly Asn Asn Gln Gly
    290                 295                 300

Ser Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
                325                 330                 335

Met Gly Met Leu Ala Ser Gln Gln Asn Gln Ser Gly Pro Ser Gly Asn
            340                 345                 350

Asn Gln Asn Gln Gly Asn Met Gln Arg Glu Pro Asn Gln Ala Phe Gly
        355                 360                 365

Ser Gly Asn Asn Ser Tyr Ser Gly Ser Asn Ser Gly Ala Ala Ile Gly
    370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
                405                 410

<210> SEQ ID NO 3
<211> LENGTH: 28
<212> TYPE: DNA
<213> ORGANISM: Artificial
<220> FEATURE:
<223> OTHER INFORMATION: synthetic DNA

<400> SEQUENCE: 3
cgggatccat gtctgaatat attcgggt                                      28

<210> SEQ ID NO 4
<211> LENGTH: 28
<212> TYPE: DNA
<213> ORGANISM: Artificial
<220> FEATURE:
<223> OTHER INFORMATION: synthetic DNA

<400> SEQUENCE: 4
gctctagact acattcccca gccagaag                                      28

<210> SEQ ID NO 5
<211> LENGTH: 38
<212> TYPE: DNA
<213> ORGANISM: Artificial
<220> FEATURE:
<223> OTHER INFORMATION: synthetic DNA

<400> SEQUENCE: 5
ccgctcgagc tatgtctgaa tatattcggg taaccgaa                           38

<210> SEQ ID NO 6
<211> LENGTH: 28
<212> TYPE: DNA
<213> ORGANISM: Artificial
<220> FEATURE:
<223> OTHER INFORMATION: synthetic DNA

<400> SEQUENCE: 6
cgggatccct acattcccca gccagaag                                      28
```

<210> SEQ ID NO 7
<211> LENGTH: 30
<212> TYPE: DNA
<213> ORGANISM: Artificial
<220> FEATURE:
<223> OTHER INFORMATION: synthetic DNA

<400> SEQUENCE: 7
ccgctcgagc tatgtcacag cgacatatga                    30

<210> SEQ ID NO 8
<211> LENGTH: 30
<212> TYPE: DNA
<213> ORGANISM: Artificial
<220> FEATURE:
<223> OTHER INFORMATION: synthetic DNA

<400> SEQUENCE: 8
ccgctcgagc tatggatgtc ttcatcccca                    30

<210> SEQ ID NO 9
<211> LENGTH: 32
<212> TYPE: DNA
<213> ORGANISM: Artificial
<220> FEATURE:
<223> OTHER INFORMATION: synthetic DNA

<400> SEQUENCE: 9
ccgctcgagc tggaagattt ggtggtaatc ca                 32

<210> SEQ ID NO 10
<211> LENGTH: 34
<212> TYPE: DNA
<213> ORGANISM: Artificial
<220> FEATURE:
<223> OTHER INFORMATION: synthetic DNA

<400> SEQUENCE: 10
ccgctcgagc tgcgttcagc attaatccag ccat               34

<210> SEQ ID NO 11
<211> LENGTH: 38
<212> TYPE: DNA
<213> ORGANISM: Artificial
<220> FEATURE:
<223> OTHER INFORMATION: synthetic DNA

<400> SEQUENCE: 11
ccgctcgagc tatgtctgaa tatattcggg taaccgaa           38

<210> SEQ ID NO 12
<211> LENGTH: 28
<212> TYPE: DNA
<213> ORGANISM: Artificial
<220> FEATURE:
<223> OTHER INFORMATION: synthetic DNA

<400> SEQUENCE: 12
cgggatccct atactttcac ttgtgttt                      28

<210> SEQ ID NO 13
<211> LENGTH: 28
<212> TYPE: DNA
<213> ORGANISM: Artificial
<220> FEATURE:

-continued

<223> OTHER INFORMATION: synthetic DNA

<400> SEQUENCE: 13
cgggatccct acacatcccc gtactgag                                28

<210> SEQ ID NO 14
<211> LENGTH: 35
<212> TYPE: DNA
<213> ORGANISM: Artificial
<220> FEATURE:
<223> OTHER INFORMATION: synthetic DNA

<400> SEQUENCE: 14
cgggatccct aacttctttc taactgtcta ttgct                        35

<210> SEQ ID NO 15
<211> LENGTH: 35
<212> TYPE: DNA
<213> ORGANISM: Artificial
<220> FEATURE:
<223> OTHER INFORMATION: synthetic DNA

<400> SEQUENCE: 15
cgggatccct aaccaaagtt catcccacca cccat                        35

<210> SEQ ID NO 16
<211> LENGTH: 6132
<212> TYPE: DNA
<213> ORGANISM: Homo sapiens
<220> FEATURE:
<221> NAME/KEY: CDS
<222> LOCATION: (133)..(4575)

<400> SEQUENCE: 16

```
aattggaagc aaatgacatc acagcaggtc agagaaaaag ggttgagcgg caggcaccca    60
gagtagtagg tctttggcat taggagcttg agcccgacg gccctagcag ggaccccagc   120
gcccgagaga cc atg cag agg tcg cct ctg gaa aag gcc agc gtt gtc tcc   171
              Met Gln Arg Ser Pro Leu Glu Lys Ala Ser Val Val Ser
              1               5                   10 aaa ctt ttt ttc agc tgg acc aga cca att ttg agg aaa gga tac aga    219
Lys Leu Phe Phe Ser Trp Thr Arg Pro Ile Leu Arg Lys Gly Tyr Arg
 15                  20                  25 cag cgc ctg gaa ttg tca gac ata tac caa atc cct tct gtt gat tct    267
Gln Arg Leu Glu Leu Ser Asp Ile Tyr Gln Ile Pro Ser Val Asp Ser
 30                  35                  40                  45 gct gac aat cta tct gaa aaa ttg gaa aga gaa tgg gat aga gag ctg    315
Ala Asp Asn Leu Ser Glu Lys Leu Glu Arg Glu Trp Asp Arg Glu Leu
                 50                  55                  60 gct tca aag aaa aat cct aaa ctc att aat gcc ctt cgg cga tgt ttt    363
Ala Ser Lys Lys Asn Pro Lys Leu Ile Asn Ala Leu Arg Arg Cys Phe
             65                  70                  75 ttc tgg aga ttt atg ttc tat gga atc ttt tta tat tta ggg gaa gtc    411
Phe Trp Arg Phe Met Phe Tyr Gly Ile Phe Leu Tyr Leu Gly Glu Val
         80                  85                  90 acc aaa gca gta cag cct ctc tta ctg gga aga atc ata gct tcc tat    459
Thr Lys Ala Val Gln Pro Leu Leu Leu Gly Arg Ile Ile Ala Ser Tyr
     95                  100                 105 gac ccg gat aac aag gag gaa cgc tct atc gcg att tat cta ggc ata    507
Asp Pro Asp Asn Lys Glu Glu Arg Ser Ile Ala Ile Tyr Leu Gly Ile
110                  115                 120                 125 ggc tta tgc ctt ctc ttt att gtg agg aca ctg ctc cta cac cca gcc    555
Gly Leu Cys Leu Leu Phe Ile Val Arg Thr Leu Leu Leu His Pro Ala
```

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 130 |     |     |     | 135 |     |     |     | 140 |     |     |     |     |      |
| att | ttt | ggc | ctt | cat | cac | att | gga | atg | cag | atg | aga | ata | gct | atg | ttt | 603  |
| Ile | Phe | Gly | Leu | His | His | Ile | Gly | Met | Gln | Met | Arg | Ile | Ala | Met | Phe |      |
|     |     |     | 145 |     |     |     | 150 |     |     |     | 155 |     |     |     |     |      |
| agt | ttg | att | tat | aag | aag | act | tta | aag | ctg | tca | agc | cgt | gtt | cta | gat | 651  |
| Ser | Leu | Ile | Tyr | Lys | Lys | Thr | Leu | Lys | Leu | Ser | Ser | Arg | Val | Leu | Asp |      |
|     |     | 160 |     |     |     |     | 165 |     |     |     |     | 170 |     |     |     |      |
| aaa | ata | agt | att | gga | caa | ctt | gtt | agt | ctc | ctt | tcc | aac | aac | ctg | aac | 699  |
| Lys | Ile | Ser | Ile | Gly | Gln | Leu | Val | Ser | Leu | Leu | Ser | Asn | Asn | Leu | Asn |      |
|     | 175 |     |     |     |     | 180 |     |     |     |     | 185 |     |     |     |     |      |
| aaa | ttt | gat | gaa | gga | ctt | gca | ttg | gca | cat | ttc | gtg | tgg | atc | gct | cct | 747  |
| Lys | Phe | Asp | Glu | Gly | Leu | Ala | Leu | Ala | His | Phe | Val | Trp | Ile | Ala | Pro |      |
| 190 |     |     |     |     | 195 |     |     |     |     | 200 |     |     |     |     | 205 |      |
| ttg | caa | gtg | gca | ctc | ctc | atg | ggg | cta | atc | tgg | gag | ttg | tta | cag | gcg | 795  |
| Leu | Gln | Val | Ala | Leu | Leu | Met | Gly | Leu | Ile | Trp | Glu | Leu | Leu | Gln | Ala |      |
|     |     |     |     | 210 |     |     |     |     | 215 |     |     |     |     | 220 |     |      |
| tct | gcc | ttc | tgt | gga | ctt | ggt | ttc | ctg | ata | gtc | ctt | gcc | ctt | ttt | cag | 843  |
| Ser | Ala | Phe | Cys | Gly | Leu | Gly | Phe | Leu | Ile | Val | Leu | Ala | Leu | Phe | Gln |      |
|     |     |     | 225 |     |     |     |     | 230 |     |     |     |     | 235 |     |     |      |
| gct | ggg | cta | ggg | aga | atg | atg | atg | aag | tac | aga | gat | cag | aga | gct | ggg | 891  |
| Ala | Gly | Leu | Gly | Arg | Met | Met | Met | Lys | Tyr | Arg | Asp | Gln | Arg | Ala | Gly |      |
|     |     | 240 |     |     |     |     | 245 |     |     |     |     | 250 |     |     |     |      |
| aag | atc | agt | gaa | aga | ctt | gtg | att | acc | tca | gaa | atg | att | gaa | aat | atc | 939  |
| Lys | Ile | Ser | Glu | Arg | Leu | Val | Ile | Thr | Ser | Glu | Met | Ile | Glu | Asn | Ile |      |
|     | 255 |     |     |     |     | 260 |     |     |     |     | 265 |     |     |     |     |      |
| caa | tct | gtt | aag | gca | tac | tgc | tgg | gaa | gaa | gca | atg | gaa | aaa | atg | att | 987  |
| Gln | Ser | Val | Lys | Ala | Tyr | Cys | Trp | Glu | Glu | Ala | Met | Glu | Lys | Met | Ile |      |
| 270 |     |     |     |     | 275 |     |     |     |     | 280 |     |     |     |     | 285 |      |
| gaa | aac | tta | aga | caa | aca | gaa | ctg | aaa | ctg | act | cgg | aag | gca | gcc | tat | 1035 |
| Glu | Asn | Leu | Arg | Gln | Thr | Glu | Leu | Lys | Leu | Thr | Arg | Lys | Ala | Ala | Tyr |      |
|     |     |     |     | 290 |     |     |     |     | 295 |     |     |     |     | 300 |     |      |
| gtg | aga | tac | ttc | aat | agc | tca | gcc | ttc | ttc | tca | ggg | ttc | ttt | gtg | | 1083 |
| Val | Arg | Tyr | Phe | Asn | Ser | Ser | Ala | Phe | Phe | Ser | Gly | Phe | Phe | Val |     |      |
|     |     |     | 305 |     |     |     |     | 310 |     |     |     |     | 315 |     |     |      |
| gtg | ttt | tta | tct | gtg | ctt | ccc | tat | gca | cta | atc | aaa | gga | atc | atc | ctc | 1131 |
| Val | Phe | Leu | Ser | Val | Leu | Pro | Tyr | Ala | Leu | Ile | Lys | Gly | Ile | Ile | Leu |      |
|     |     | 320 |     |     |     |     | 325 |     |     |     |     | 330 |     |     |     |      |
| cgg | aaa | ata | ttc | acc | acc | atc | tca | ttc | tgc | att | gtt | ctg | cgc | atg | gcg | 1179 |
| Arg | Lys | Ile | Phe | Thr | Thr | Ile | Ser | Phe | Cys | Ile | Val | Leu | Arg | Met | Ala |      |
|     | 335 |     |     |     |     | 340 |     |     |     |     | 345 |     |     |     |     |      |
| gtc | act | cgg | caa | ttt | ccc | tgg | gct | gta | caa | aca | tgg | tat | gac | tct | ctt | 1227 |
| Val | Thr | Arg | Gln | Phe | Pro | Trp | Ala | Val | Gln | Thr | Trp | Tyr | Asp | Ser | Leu |      |
| 350 |     |     |     |     | 355 |     |     |     |     | 360 |     |     |     |     | 365 |      |
| gga | gca | ata | aac | aaa | ata | cag | gat | ttc | tta | caa | aag | caa | gaa | tat | aag | 1275 |
| Gly | Ala | Ile | Asn | Lys | Ile | Gln | Asp | Phe | Leu | Gln | Lys | Gln | Glu | Tyr | Lys |      |
|     |     |     | 370 |     |     |     |     | 375 |     |     |     |     | 380 |     |     |      |
| aca | ttg | gaa | tat | aac | tta | acg | act | aca | gaa | gta | gtg | atg | gag | aat | gta | 1323 |
| Thr | Leu | Glu | Tyr | Asn | Leu | Thr | Thr | Thr | Glu | Val | Val | Met | Glu | Asn | Val |      |
|     |     | 385 |     |     |     |     | 390 |     |     |     |     | 395 |     |     |     |      |
| aca | gcc | ttc | tgg | gag | gag | gga | ttt | ggg | gaa | tta | ttt | gag | aaa | gca | aaa | 1371 |
| Thr | Ala | Phe | Trp | Glu | Glu | Gly | Phe | Gly | Glu | Leu | Phe | Glu | Lys | Ala | Lys |      |
|     |     |     |     | 400 |     |     |     |     | 405 |     |     |     |     | 410 |     |      |
| caa | aac | aat | aac | aat | aga | aaa | act | tct | aat | ggt | gat | gac | agc | ctc | ttc | 1419 |
| Gln | Asn | Asn | Asn | Asn | Arg | Lys | Thr | Ser | Asn | Gly | Asp | Asp | Ser | Leu | Phe |      |
|     |     |     | 415 |     |     |     |     | 420 |     |     |     |     | 425 |     |     |      |
| ttc | agt | aat | ttc | tca | ctt | ctt | ggt | act | cct | gtc | ctg | aaa | gat | att | aat | 1467 |
| Phe | Ser | Asn | Phe | Ser | Leu | Leu | Gly | Thr | Pro | Val | Leu | Lys | Asp | Ile | Asn |      |
| 430 |     |     |     |     | 435 |     |     |     |     | 440 |     |     |     |     | 445 |      |
| ttc | aag | ata | gaa | aga | gga | cag | ttg | ttg | gcg | gtt | gct | gga | tcc | act | gga | 1515 |

```
Phe Lys Ile Glu Arg Gly Gln Leu Leu Ala Val Ala Gly Ser Thr Gly
                450                 455                 460 gca ggc aag act tca ctt cta atg gtg att atg gga gaa ctg gag cct      1563
Ala Gly Lys Thr Ser Leu Leu Met Val Ile Met Gly Glu Leu Glu Pro
            465                 470                 475 tca gag ggt aaa att aag cac agt gga aga att tca ttc tgt tct cag      1611
Ser Glu Gly Lys Ile Lys His Ser Gly Arg Ile Ser Phe Cys Ser Gln
        480                 485                 490 ttt tcc tgg att atg cct ggc acc att aaa gaa aat atc atc ttt ggt      1659
Phe Ser Trp Ile Met Pro Gly Thr Ile Lys Glu Asn Ile Ile Phe Gly
495                 500                 505 gtt tcc tat gat gaa tat aga tac aga agc gtc atc aaa gca tgc caa      1707
Val Ser Tyr Asp Glu Tyr Arg Tyr Arg Ser Val Ile Lys Ala Cys Gln
510                 515                 520                 525 cta gaa gag gac atc tcc aag ttt gca gag aaa gac aat ata gtt ctt      1755
Leu Glu Glu Asp Ile Ser Lys Phe Ala Glu Lys Asp Asn Ile Val Leu
                530                 535                 540 gga gaa ggt gga atc aca ctg agt gga ggt caa cga gca aga att tct      1803
Gly Glu Gly Gly Ile Thr Leu Ser Gly Gly Gln Arg Ala Arg Ile Ser
            545                 550                 555 tta gca aga gca gta tac aaa gat gct gat ttg tat tta tta gac tct      1851
Leu Ala Arg Ala Val Tyr Lys Asp Ala Asp Leu Tyr Leu Leu Asp Ser
        560                 565                 570 cct ttt gga tac cta gat gtt tta aca gaa aaa gaa ata ttt gaa agc      1899
Pro Phe Gly Tyr Leu Asp Val Leu Thr Glu Lys Glu Ile Phe Glu Ser
575                 580                 585 tgt gtc tgt aaa ctg atg gct aac aaa act agg att ttg gtc act tct      1947
Cys Val Cys Lys Leu Met Ala Asn Lys Thr Arg Ile Leu Val Thr Ser
590                 595                 600                 605 aaa atg gaa cat tta aag aaa gct gac aaa ata tta att ttg cat gaa      1995
Lys Met Glu His Leu Lys Lys Ala Asp Lys Ile Leu Ile Leu His Glu
                610                 615                 620 ggt agc agc tat ttt tat ggg aca ttt tca gaa ctc caa aat cta cag      2043
Gly Ser Ser Tyr Phe Tyr Gly Thr Phe Ser Glu Leu Gln Asn Leu Gln
            625                 630                 635 cca gac ttt agc tca aaa ctc atg gga tgt gat tct ttc gac caa ttt      2091
Pro Asp Phe Ser Ser Lys Leu Met Gly Cys Asp Ser Phe Asp Gln Phe
        640                 645                 650 agt gca gaa aga aga aat tca atc cta act gag acc tta cac cgt ttc      2139
Ser Ala Glu Arg Arg Asn Ser Ile Leu Thr Glu Thr Leu His Arg Phe
655                 660                 665 tca tta gaa gga gat gct cct gtc tcc tgg aca gaa aca aaa aaa caa      2187
Ser Leu Glu Gly Asp Ala Pro Val Ser Trp Thr Glu Thr Lys Lys Gln
670                 675                 680                 685 tct ttt aaa cag act gga gag ttt ggg gaa aaa agg aag aat tct att      2235
Ser Phe Lys Gln Thr Gly Glu Phe Gly Glu Lys Arg Lys Asn Ser Ile
                690                 695                 700 ctc aat cca atc aac tct ata cga aaa ttt tcc att gtg caa aag act      2283
Leu Asn Pro Ile Asn Ser Ile Arg Lys Phe Ser Ile Val Gln Lys Thr
            705                 710                 715 ccc tta caa atg aat ggc atc gaa gag gat tct gat gag cct tta gag      2331
Pro Leu Gln Met Asn Gly Ile Glu Glu Asp Ser Asp Glu Pro Leu Glu
        720                 725                 730 aga agg ctg tcc tta gta cca gat tct gag cag gga gag gcg ata ctg      2379
Arg Arg Leu Ser Leu Val Pro Asp Ser Glu Gln Gly Glu Ala Ile Leu
735                 740                 745 cct cgc atc agc gtg atc agc act ggc ccc acg ctt cag gca cga agg      2427
Pro Arg Ile Ser Val Ile Ser Thr Gly Pro Thr Leu Gln Ala Arg Arg
750                 755                 760                 765
```

-continued

| | |
|---|---|
| agg cag tct gtc ctg aac ctg atg aca cac tca gtt aac caa ggt cag<br>Arg Gln Ser Val Leu Asn Leu Met Thr His Ser Val Asn Gln Gly Gln<br>770             775                 780 | 2475 |
| aac att cac cga aag aca aca gca tcc aca cga aaa gtg tca ctg gcc<br>Asn Ile His Arg Lys Thr Thr Ala Ser Thr Arg Lys Val Ser Leu Ala<br>    785                 790                 795 | 2523 |
| cct cag gca aac ttg act gaa ctg gat ata tat tca aga agg tta tct<br>Pro Gln Ala Asn Leu Thr Glu Leu Asp Ile Tyr Ser Arg Arg Leu Ser<br>        800                 805                 810 | 2571 |
| caa gaa act ggc ttg gaa ata agt gaa gaa att aac gaa gaa gac tta<br>Gln Glu Thr Gly Leu Glu Ile Ser Glu Glu Ile Asn Glu Glu Asp Leu<br>            815                 820                 825 | 2619 |
| aag gag tgc ttt ttt gat gat atg gag agc ata cca gca gtg act aca<br>Lys Glu Cys Phe Phe Asp Asp Met Glu Ser Ile Pro Ala Val Thr Thr<br>830                 835                 840                 845 | 2667 |
| tgg aac aca tac ctt cga tat att act gtc cac aag agc tta att ttt<br>Trp Asn Thr Tyr Leu Arg Tyr Ile Thr Val His Lys Ser Leu Ile Phe<br>    850                 855                 860 | 2715 |
| gtg cta att tgg tgc tta gta att ttt ctg gca gag gtg gct gct tct<br>Val Leu Ile Trp Cys Leu Val Ile Phe Leu Ala Glu Val Ala Ala Ser<br>        865                 870                 875 | 2763 |
| ttg gtt gtg ctg tgg ctc ctt gga aac act cct ctt caa gac aaa ggg<br>Leu Val Val Leu Trp Leu Leu Gly Asn Thr Pro Leu Gln Asp Lys Gly<br>            880                 885                 890 | 2811 |
| aat agt act cat agt aga aat aac agc tat gca gtg att atc acc agc<br>Asn Ser Thr His Ser Arg Asn Asn Ser Tyr Ala Val Ile Ile Thr Ser<br>895                 900                 905 | 2859 |
| acc agt tcg tat tat gtg ttt tac att tac gtg gga gta gcc gac act<br>Thr Ser Ser Tyr Tyr Val Phe Tyr Ile Tyr Val Gly Val Ala Asp Thr<br>910                 915                 920                 925 | 2907 |
| ttg ctt gct atg gga ttc ttc aga ggt cta cca ctg gtg cat act cta<br>Leu Leu Ala Met Gly Phe Phe Arg Gly Leu Pro Leu Val His Thr Leu<br>    930                 935                 940 | 2955 |
| atc aca gtg tcg aaa att tta cac cac aaa atg tta cat tct gtt ctt<br>Ile Thr Val Ser Lys Ile Leu His His Lys Met Leu His Ser Val Leu<br>        945                 950                 955 | 3003 |
| caa gca cct atg tca acc ctc aac acg ttg aaa gca ggt ggg att ctt<br>Gln Ala Pro Met Ser Thr Leu Asn Thr Leu Lys Ala Gly Gly Ile Leu<br>            960                 965                 970 | 3051 |
| aat aga ttc tcc aaa gat ata gca att ttg gat gac ctt ctg cct ctt<br>Asn Arg Phe Ser Lys Asp Ile Ala Ile Leu Asp Asp Leu Leu Pro Leu<br>975                 980                 985 | 3099 |
| acc ata ttt gac ttc atc cag ttg tta tta att  gtg att gga gct ata<br>Thr Ile Phe Asp Phe Ile Gln Leu Leu Leu Ile  Val Ile Gly Ala Ile<br>990                 995                 1000                1005 | 3147 |
| gca gtt gtc gca gtt  tta caa ccc tac atc  ttt gtt gca aca gtg<br>Ala Val Val Ala Val  Leu Gln Pro Tyr Ile  Phe Val Ala Thr Val<br>            1010                1015                1020 | 3192 |
| cca gtg ata gtg gct  ttt att atg ttg aga  gca tat ttc ctc caa<br>Pro Val Ile Val Ala  Phe Ile Met Leu Arg  Ala Tyr Phe Leu Gln<br>            1025                1030                1035 | 3237 |
| acc tca cag caa ctc  aaa caa ctg gaa tct  gaa ggc agg agt cca<br>Thr Ser Gln Gln Leu  Lys Gln Leu Glu Ser  Glu Gly Arg Ser Pro<br>            1040                1045                1050 | 3282 |
| att ttc act cat ctt  gtt aca agc tta aaa  gga cta tgg aca ctt<br>Ile Phe Thr His Leu  Val Thr Ser Leu Lys  Gly Leu Trp Thr Leu<br>            1055                1060                1065 | 3327 |
| cgt gcc ttc gga cgg  cag cct tac ttt gaa  act ctg ttc cac aaa<br>Arg Ala Phe Gly Arg  Gln Pro Tyr Phe Glu  Thr Leu Phe His Lys<br>            1070                1075                1080 | 3372 |

```
gct ctg aat tta cat act gcc aac tgg ttc ttg tac ctg tca aca      3417
Ala Leu Asn Leu His Thr Ala Asn Trp Phe Leu Tyr Leu Ser Thr
            1085                1090                1095 ctg cgc tgg ttc caa atg aga ata gaa atg att ttt gtc atc ttc      3462
Leu Arg Trp Phe Gln Met Arg Ile Glu Met Ile Phe Val Ile Phe
                1100                1105                1110 ttc att gct gtt acc ttc att tcc att tta aca aca gga gaa gga      3507
Phe Ile Ala Val Thr Phe Ile Ser Ile Leu Thr Thr Gly Glu Gly
                    1115                1120                1125 gaa gga aga gtt ggt att atc ctg act tta gcc atg aat atc atg      3552
Glu Gly Arg Val Gly Ile Ile Leu Thr Leu Ala Met Asn Ile Met
                        1130                1135                1140 agt aca ttg cag tgg gct gta aac tcc agc ata gat gtg gat agc      3597
Ser Thr Leu Gln Trp Ala Val Asn Ser Ser Ile Asp Val Asp Ser
                            1145                1150                1155 ttg atg cga tct gtg agc cga gtc ttt aag ttc att gac atg cca      3642
Leu Met Arg Ser Val Ser Arg Val Phe Lys Phe Ile Asp Met Pro
                                1160                1165                1170 aca gaa ggt aaa cct acc aag tca acc aaa cca tac aag aat ggc      3687
Thr Glu Gly Lys Pro Thr Lys Ser Thr Lys Pro Tyr Lys Asn Gly
                                    1175                1180                1185 caa ctc tcg aaa gtt atg att att gag aat tca cac gtg aag aaa      3732
Gln Leu Ser Lys Val Met Ile Ile Glu Asn Ser His Val Lys Lys
                                        1190                1195                1200 gat gac atc tgg ccc tca ggg ggc caa atg act gtc aaa gat ctc      3777
Asp Asp Ile Trp Pro Ser Gly Gly Gln Met Thr Val Lys Asp Leu
                                            1205                1210                1215 aca gca aaa tac aca gaa ggt gga aat gcc ata tta gag aac att      3822
Thr Ala Lys Tyr Thr Glu Gly Gly Asn Ala Ile Leu Glu Asn Ile
                                                1220                1225                1230 tcc ttc tca ata agt cct ggc cag agg gtg ggc ctc ttg gga aga      3867
Ser Phe Ser Ile Ser Pro Gly Gln Arg Val Gly Leu Leu Gly Arg
                                                    1235                1240                1245 act gga tca ggg aag agt act ttg tta tca gct ttt ttg aga cta      3912
Thr Gly Ser Gly Lys Ser Thr Leu Leu Ser Ala Phe Leu Arg Leu
                                                        1250                1255                1260 ctg aac act gaa gga gaa atc cag atc gat ggt gtg tct tgg gat      3957
Leu Asn Thr Glu Gly Glu Ile Gln Ile Asp Gly Val Ser Trp Asp
                                                            1265                1270                1275 tca ata act ttg caa cag tgg agg aaa gcc ttt gga gtg ata cca      4002
Ser Ile Thr Leu Gln Gln Trp Arg Lys Ala Phe Gly Val Ile Pro
                                                                1280                1285                1290 cag aaa gta ttt att ttt tct gga aca ttt aga aaa aac ttg gat      4047
Gln Lys Val Phe Ile Phe Ser Gly Thr Phe Arg Lys Asn Leu Asp
                                                                    1295                1300                1305 ccc tat gaa cag tgg agt gat caa gaa ata tgg aaa gtt gca gat      4092
Pro Tyr Glu Gln Trp Ser Asp Gln Glu Ile Trp Lys Val Ala Asp
                                                                        1310                1315                1320 gag gtt ggg ctc aga tct gtg ata gaa cag ttt cct ggg aag ctt      4137
Glu Val Gly Leu Arg Ser Val Ile Glu Gln Phe Pro Gly Lys Leu
                                                                            1325                1330                1335 gac ttt gtc ctt gtg gat ggg ggc tgt gtc cta agc cat ggc cac      4182
Asp Phe Val Leu Val Asp Gly Gly Cys Val Leu Ser His Gly His
                                                                                1340                1345                1350 aag cag ttg atg tgc ttg gct aga tct gtt ctc agt aag gcg aag      4227
Lys Gln Leu Met Cys Leu Ala Arg Ser Val Leu Ser Lys Ala Lys
                                                                                    1355                1360                1365 atc ttg ctg ctt gat gaa ccc agt gct cat ttg gat cca gta aca      4272
Ile Leu Leu Leu Asp Glu Pro Ser Ala His Leu Asp Pro Val Thr
```

|     |     |     |     |     |     |     |     |     |     |     |     |     |     |      |
|-----|-----|-----|-----|-----|-----|-----|-----|-----|-----|-----|-----|-----|-----|------|
|     |     |     | 1370 |     |     |     | 1375 |     |     |     | 1380 |     |     |      |
| tac | caa | ata | att | aga | aga | act | cta | aaa | caa | gca | ttt | gct | gat | tgc  | 4317 |
| Tyr | Gln | Ile | Ile | Arg | Arg | Thr | Leu | Lys | Gln | Ala | Phe | Ala | Asp | Cys  |
|     |     |     | 1385 |     |     |     | 1390 |     |     |     | 1395 |     |     |      |
| aca | gta | att | ctc | tgt | gaa | cac | agg | ata | gaa | gca | atg | ctg | gaa | tgc  | 4362 |
| Thr | Val | Ile | Leu | Cys | Glu | His | Arg | Ile | Glu | Ala | Met | Leu | Glu | Cys  |
|     |     |     | 1400 |     |     |     | 1405 |     |     |     | 1410 |     |     |      |
| caa | caa | ttt | ttg | gtc | ata | gaa | gag | aac | aaa | gtg | cgg | cag | tac | gat  | 4407 |
| Gln | Gln | Phe | Leu | Val | Ile | Glu | Glu | Asn | Lys | Val | Arg | Gln | Tyr | Asp  |
|     |     |     | 1415 |     |     |     | 1420 |     |     |     | 1425 |     |     |      |
| tcc | atc | cag | aaa | ctg | ctg | aac | gag | agg | agc | ctc | ttc | cgg | caa | gcc  | 4452 |
| Ser | Ile | Gln | Lys | Leu | Leu | Asn | Glu | Arg | Ser | Leu | Phe | Arg | Gln | Ala  |
|     |     |     | 1430 |     |     |     | 1435 |     |     |     | 1440 |     |     |      |
| atc | agc | ccc | tcc | gac | agg | gtg | aag | ctc | ttt | ccc | cac | cgg | aac | tca  | 4497 |
| Ile | Ser | Pro | Ser | Asp | Arg | Val | Lys | Leu | Phe | Pro | His | Arg | Asn | Ser  |
|     |     |     | 1445 |     |     |     | 1450 |     |     |     | 1455 |     |     |      |
| agc | aag | tgc | aag | tct | aag | ccc | cag | att | gct | gct | ctg | aaa | gag | gag  | 4542 |
| Ser | Lys | Cys | Lys | Ser | Lys | Pro | Gln | Ile | Ala | Ala | Leu | Lys | Glu | Glu  |
|     |     |     | 1460 |     |     |     | 1465 |     |     |     | 1470 |     |     |      |
| aca | gaa | gaa | gag | gtg | caa | gat | aca | agg | ctt | tag | agagcagcat |   |   |      | 4585 |
| Thr | Glu | Glu | Glu | Val | Gln | Asp | Thr | Arg | Leu |     |     |     |     |      |
|     |     |     | 1475 |     |     |     | 1480 |     |     |     |     |     |     |      |

```
aaatgttgac atgggacatt tgctcatgga attggagctc gtgggacagt cacctcatgg   4645
aattggagct cgtggaacag ttacctctgc ctcagaaaac aaggatgaat taagtttttt   4705
tttaaaaaag aaacatttgg taaggggaat tgaggacact gatatgggtc ttgataaatg   4765
gcttcctggc aatagtcaaa ttgtgtgaaa ggtacttcaa atccttgaag atttaccact   4825
tgtgttttgc aagccagatt ttcctgaaaa cccttgccat gtgctagtaa ttggaaaggc   4885
agctctaaat gtcaatcagc ctagttgatc agcttattgt ctagtgaaac tcgttaattt   4945
gtagtgttgg agaagaactg aaatcatact tcttagggtt atgattaagt aatgataact   5005
ggaaacttca gcggtttata taagcttgta ttccttttc tctcctctcc ccatgatgtt   5065
tagaaacaca actatattgt ttgctaagca ttccaactat ctcatttcca agcaagtatt   5125
agaataccac aggaaccaca agactgcaca tcaaaatatg ccccattcaa catctagtga   5185
gcagtcagga aagagaactt ccagatcctg gaaatcaggg ttagtattgt ccaggtctac   5245
caaaaatctc aatatttcag ataatcacaa tacatcccct acctgggaaa gggctgttat   5305
aatcttttcac aggggacagg atggttccct tgatgaagaa gttgatatgc cttttcccaa   5365
ctccagaaag tgacaagctc acagaccttt gaactagagt ttagctggaa aagtatgtta   5425
gtgcaaattg tcacaggaca gcccttcttt ccacagaagc tccaggtaga gggtgtgtaa   5485
gtagataggc catgggcact gtgggtagac acacatgaag tccaagcatt tagatgtata   5545
ggttgatggt ggtatgtttt caggctagat gtatgtactt catgctgtct acactaagag   5605
agaatgagag acacactgaa gaagcaccaa tcatgaatta gttttatatg cttctgtttt   5665
ataattttgt gaagcaaaat ttttctcta ggaaatattt attttaataa tgtttcaaac   5725
atatataaca atgctgtatt ttaaaagaat gattatgaat tacatttgta taaaataatt   5785
tttatatttg aaatattgac tttttatggc actagtattt ctatgaaata ttatgttaaa   5845
actgggacag gggagaacct agggtgatat taaccagggg ccatgaatca ccttttggtc   5905
tggagggaag ccttggggct gatgcagttg ttgcccacag ctgtatgatt cccagccagc   5965
acagcctctt agatgcagtt ctgaagaaga tggtaccacc agtctgactg tttccatcaa   6025
gggtacactg ccttctcaac tccaaactga ctcttaagaa gactgcatta tatttattac   6085
```

```
tgtaagaaaa tatcacttgt caataaaatc catacatttg tgtgaaa            6132

<210> SEQ ID NO 17
<211> LENGTH: 29
<212> TYPE: DNA
<213> ORGANISM: Artificial
<220> FEATURE:
<223> OTHER INFORMATION: synthetic DNA

<400> SEQUENCE: 17
cggaattcac ttgataatgg gcaaatatc                                29

<210> SEQ ID NO 18
<211> LENGTH: 29
<212> TYPE: DNA
<213> ORGANISM: Artificial
<220> FEATURE:
<223> OTHER INFORMATION: synthetic DNA

<400> SEQUENCE: 18
ccctcgagct cgccatgtgc aagatacag                                29

<210> SEQ ID NO 19
<211> LENGTH: 11
<212> TYPE: PRT
<213> ORGANISM: Artificial
<220> FEATURE:
<223> OTHER INFORMATION: phosphorylated synthetic peptide
<220> FEATURE:
<221> NAME/KEY: MOD_RES
<222> LOCATION: (6)..(7)
<223> OTHER INFORMATION: PHOSPHORYLATION

<400> SEQUENCE: 19

Cys Met Asp Ser Lys Ser Ser Gly Trp Gly Met
1               5                   10

<210> SEQ ID NO 20
<211> LENGTH: 10
<212> TYPE: PRT
<213> ORGANISM: Artificial
<220> FEATURE:
<223> OTHER INFORMATION: synthetic peptide

<400> SEQUENCE: 20

Met Asp Ser Lys Ser Ser Gly Trp Gly Met
1               5                   10
```